United States Patent
Ziady et al.

(10) Patent No.: US 12,411,144 B2
(45) Date of Patent: *Sep. 9, 2025

(54) COMPOSITIONS AND METHODS FOR TREATMENT OF LUNG FUNCTION

(71) Applicant: Children's Hospital Medical Center, Cincinnati, OH (US)

(72) Inventors: Assem Ziady, Newport, KY (US); Rhonda Szczesniak, Burlington, KY (US); Emrah Gecili, Cincinnati, OH (US); Zackary Cleveland, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 993 days.

This patent is subject to a terminal disclaimer.

(21) Appl. No.: 17/333,058

(22) Filed: May 28, 2021

(65) Prior Publication Data

US 2021/0302439 A1 Sep. 30, 2021

Related U.S. Application Data

(63) Continuation-in-part of application No. 16/922,119, filed on Jul. 7, 2020, now abandoned, which is a
(Continued)

(51) Int. Cl.
*G01N 33/68* (2006.01)

(52) U.S. Cl.
CPC ..... *G01N 33/6893* (2013.01); *G01N 33/6851* (2013.01); *G01N 2333/914* (2013.01);
(Continued)

(58) Field of Classification Search
CPC ......... G01N 33/6893; G01N 33/6851; G01N 2333/914; G01N 2800/382; G01N 2800/50

See application file for complete search history.

(56) References Cited

U.S. PATENT DOCUMENTS

| | | | |
|---|---|---|---|
| 4,208,479 A | 6/1980 | Zuk et al. | |
| 7,741,038 B2 | 6/2010 | Sarwal et al. | |

(Continued)

FOREIGN PATENT DOCUMENTS

| | | |
|---|---|---|
| AU | 2013270447 A1 | 1/2014 |
| WO | 2009/038913 A2 | 3/2009 |

(Continued)

OTHER PUBLICATIONS

Long (Zhongguo Shiyong Neike Zashi 2015 vol. 35, p. 938-940; English translation) (Year: 2015).*

(Continued)

*Primary Examiner* — Changhwa J Cheu
(74) *Attorney, Agent, or Firm* — Frost Brown Todd LLP; Nicole M. Tepe

(57) ABSTRACT

Disclosed herein are methods for detecting protein expression in an individual diagnosed with cystic fibrosis. The methods, in certain aspects, include the steps of obtaining a sample from said individual and detecting expression in said sample of each protein of a protein set. The method may further include the step of determining expression level of one or more proteins of the protein set. The disclosed methods may be used to predict one or more clinical parameters in an individual having cystic fibrosis.

24 Claims, 16 Drawing Sheets

Related U.S. Application Data continuation of application No. 15/927,575, filed on Mar. 21, 2018, now Pat. No. 10,761,099.

(60) Provisional application No. 62/474,739, filed on Mar. 22, 2017.

(52) U.S. Cl.
CPC ... *G01N 2800/382* (2013.01); *G01N 2800/50* (2013.01); *G01N 2800/56* (2013.01)

(56) References Cited

U.S. PATENT DOCUMENTS

| | | | |
|---|---|---|---|
| 8,017,577 | B2 | 9/2011 | Cooper et al. |
| 8,911,786 | B2 | 12/2014 | Desai et al. |
| 9,018,179 | B2 | 4/2015 | Kay et al. |
| 9,993,494 | B2 | 6/2018 | Appleman et al. |
| 10,126,295 | B2 * | 11/2018 | Saavedra ............... G16H 50/30 |
| 10,300,143 | B2 | 5/2019 | Sengupta et al. |
| 10,654,910 | B2 | 5/2020 | Spencer et al. |
| 10,761,099 | B2 | 9/2020 | Ziady et al. |
| 10,894,960 | B2 | 1/2021 | Ziady et al. |
| 2006/0142225 | A1 | 6/2006 | McSwiggen |
| 2006/0148828 | A1 | 7/2006 | Gianella-Borradori et al. |
| 2006/0153808 | A1 | 7/2006 | Cristofanilli et al. |
| 2006/0241028 | A1 * | 10/2006 | Bevec .................... A61K 38/06 530/324 |
| 2006/0292562 | A1 | 12/2006 | Pollard et al. |
| 2008/0133141 | A1 * | 6/2008 | Frost .................. G01N 33/6848 600/300 |
| 2011/0172278 | A1 * | 7/2011 | He ....................... C07D 271/06 548/131 |
| 2013/0143752 | A1 | 6/2013 | Edmiston et al. |
| 2017/0042819 | A1 | 2/2017 | Goomer |
| 2017/0314074 | A1 | 11/2017 | Kossen et al. |
| 2017/0360749 | A1 * | 12/2017 | Harijith ............... A61M 15/009 |
| 2018/0009873 | A1 | 1/2018 | Spencer et al. |
| 2019/0128901 | A1 | 5/2019 | Cozma |
| 2020/0341009 | A1 | 10/2020 | Ziady et al. |
| 2022/0202902 | A1 | 6/2022 | Ziady |
| 2023/0330121 | A1 | 10/2023 | Ziady et al. |
| 2023/0416782 | A1 | 12/2023 | Ziady et al. |
| 2024/0066021 | A1 | 2/2024 | Ziady et al. |
| 2024/0103017 | A1 | 3/2024 | Hardie et al. |

FOREIGN PATENT DOCUMENTS

| | | |
|---|---|---|
| WO | 2009/055671 A1 | 4/2009 |
| WO | 2011/038901 A1 | 4/2011 |
| WO | 2015/157546 A1 | 10/2015 |
| WO | 2018/208849 A1 | 11/2018 |
| WO | 2021/053058 A1 | 3/2021 |
| WO | 2022/031877 A1 | 2/2022 |

OTHER PUBLICATIONS

Ni (Intl. J. COPD 2015 vol. 10: 1465-1475). (Year: 2015).*
Martinez-Garcia (Clinical Pulmonary Medicine 2015 vol. 22: 123-127). (Year: 2015).*
Tepper (Eur Radiol 2016 26.4563-4599) (Year. 2016).*
Schaad (Pediatric Research 1990 27:508-513) (Year 1990).*
Hassan (Immunological investigateion 1994 23: 1-13) (Year: 1994).*
Accurso FJ, et al., "Effect of VX-770 in Persons with Cystic Fibrosis and the G551D-CFTR Mutation." N Engl J Med, Nov. 18, 2010, 363(21):1991-2003, 13 pgs.
Ahmed, H., et al., "Emerging Gene Therapies for Genetic Hearing Loss," J Assoc Res Otolaryngol, Aug. 16, 2017, 22 pgs.
Albert PS, et al., "An Approach For Jointly Modeling Multivariate Longitudinal Measurements And Discrete Time-To-Event Data," Ann Appl Stat, 2010, 4(3): 1517-1532, 16 pgs.
Asar O, et al., "mmm: An R package for analyzing multivariate longitudinal data with multivariate marginal models," Comput Methods Programs Biomed, 2013, 112(3):649-654, 6 pgs.

Brebner JA, et al., "Polyclonal free light chains: a biomarker of inflammatory disease or treatment target?" F1000 Med Rep, 2013, 5:4, 6 pgs.
Bundgaard, H., (ed.), *Design of Prodrugs*, Elsevier, Amsterdam, 1985, pp. 7-9, 21-24, 8 pgs.
Cai, X., et al., "Gene delivery to mitotic and postmitotic photoreceptors via compacted DNA nanoparticles results in improved phenotype in a mouse model of retinitis pigmentosa," FASEB J, Apr. 2010, 24(4):1178-91, 25 pgs.
Chatterjee N, et al., "Constrained Maximum Likelihood Estimation for Model Calibration Using Summary-level Information from External Big Data Sources" J Am Stat Assoc, 2016, 111(513):107-117, 11 pgs.
Chen J, et al., "Dysfunction of Nrf-2 in CF Epithelia Leads to Excess Intracellular $H_2O_2$ and Inflammatory Cytokine Production," PLoS One, 2008, 3(10):e3367, 12 pgs.
Chen X, et al., "Nucleolin-Mediated Cellular Trafficking of DNA Nanoparticle Is Lipid Raft and Microtubule Dependent and Can Be Modulated by Glucocorticoid," Mol Ther, 2011, 19(1):93-102, 10 pgs.
Chipman HA, et al., "BART: Bayesian Additive Regression Trees," Ann Appl Stat, 2014, 23(1):42-59, 33 pgs.
Chirkova T, et al., "CX3CR1 is an important surface molecule for respiratory syncytial virus infection in human airway epithelial cells," J Gen Virol, 2015, 96:2543-2556, 14 pgs.
Chmiel J, et al., "The Effect of Sulforaphane In Broccoli Sprouts On Nrf2 Activation, Glutathione, Markers of Oxidative Stress, and Neutrophil Migration," Pediatr Pulmonol, 2012, 47(S35):250; 2012 Cystic Fibrosis Conference, Poster Session Abstract 82*, 1 pg.
Chromy, B.A., et al., "Proteomic Analysis of Human Serum by Two-Dimensional Differential Gel Electrophoresis after Depletion of High-Abundant Proteins," Journal of Proteome Research, 2004, 3:1120-1127, 8 pgs.
Chui, CK, et al., "Interpolation by Multivariate Splines," Math Comput, 1988, 51(183):203-218, 16 pgs.
Clancy JP, et al., "Personalized Medicine in Cystic Fibrosis: Dawning of a New Era," Am J Respir Crit Care Med, 2012, 186(7):593-597, 5 pgs.
Diggle Pj, et al., "Real-time monitoring of progression towards renal failure in primary care patients," Biostatistics, 2015, 16(3):522-536, 15 pgs.
Ding, X.Q., et al., "Ocular delivery of compacted DNA-nanoparticles does not elicit toxicity in the mouse retina," PLoS One, 2009, 4(10):e7410, 11 pgs.
Drumm ML, et al., "Genetic Variation and Clinical Heterogeneity in Cystic Fibrosis," Annu Rev Pathol, 2012, 7:267-282, 18 pgs.
Duan LL, et at., "Bayesian Ensemble Trees (BET) for Clustering and Prediction in Heterogeneous Data," J Comput Graph Stat, 2016, 25(3):748-761, 14 pgs.
Duan LL, et al., "Joint Hierarchical Gaussian Process Model with Application to Forecast in Medical Monitoring," 2014, eprint arXiv:1408.4660, 23 pgs.
Farjo, R., et al., "Efficient non-viral ocular gene transfer with compacted DNA nanoparticles," PLoS One, 2006, 1:e38, 12 pgs.
Feng, S., et al., "Recombinant adenoviral vector expressing human wild-type p53, GM-CSF, and B7-1 genes suppresses the growth of glioma in vivo," Tumor Biol, 2014, 35:441-4417, 7 pgs.
Fieuws S, et al., "Predicting renal graft failure using multivariate longitudinal profiles," Biostatistics, 2008, 9(3):419-431, 13 pgs.
Fieuws S, et al., "Random-effects models for multivariate repeated measures," Stat Methods Med Res, Oct. 2007, 16(5):387-397, 11 pgs.
Fischer K, et al., "Biomarker Profiling by Nuclear Magnetic Resonance Spectroscopy for the Prediction of All-Cause Mortality: An Observational Study of 17,345 Persons," PLoS Med, Feb. 2014, 11(2):e1001606, 12 pgs.
Fletcher, A.M., et al., "Transgene expression in the striatum following intracerebral injections of DNA nanoparticles encoding for human glial cell line-derived neurotrophic factor," Neuroscience, Oct. 27, 2011, 194:220-6, 7 pgs.

(56) References Cited

OTHER PUBLICATIONS

Green, PJ, et al., "Nonparametric regression and generalized linear models: a roughness penalty approach," $1^{st}$ ed. London, New York: Chapman & Hall, 1994, ix, 182 p. Table of Contents Only, 8 pgs.
Groot Kormelink, T., et al., "Immunoglobulin Free Light Chains Are Increased in Hypersensitivity Pneumonitis and Idiopathic Pulmonary Fibrosis," PLoS one, 2011, 6(9):e25392, 7 pgs.
Harun SN, et al., "A systematic review of studies examining the rate of lung function decline in patients with cystic fibrosis," Paediatr Respir Rev, 2016, 20:55-66, 12 pgs.
Hastie T, et al., *The Elements of Statistical Learning: Data Mining, Inference, and Prediction*, Second Ed., Springer Science + Business Media, LLC, New York, NY, 2009, (Table of Contents Only) 12 pgs.
Huang, J., et al., "CRISPR Editing in Biological and Biomedical Investigation," J Cell Physiol, Aug. 8, 2017, 19 pgs.
Huang, L., et al., "Highly Selective Targeting of Hepatic Stellate Cells for Liver Fibrosis Treatment Using a D-Enantiomeric Peptide Ligand of Fn14 Identified by Mirror-Image mRNA Display," Mol Pharmaceutics, 2017, 14:1742-1753, 12 pgs.
James GM, et al., "Principal component models for sparse functional data," Biometrika, 2000, 87(3):587-602, 16 pgs.
Jiang C-R, et al., "Covariate Adjusted Functional Principal Components Analysis For Longitudinal Data," The Annals of Statistics, 2010, 38(2): 1194-1226, 34 pgs.
Kim PY, et al., "Identification of plasma Complement C3 as a potential biomarker for neuroblastoma using a quantitative proteomic approach," J Proteomics, 2014, 96:1-12, 12 pgs.
Koirala, A., et al., "S/MAR-containing DNA nanoparticles promote persistent RPE gene expression and improvement in RPE65-associated LCA," Hum Mol Genet, Apr. 15, 2013, 22(8):1632-42, 11 pgs.
Kolodziej, M., et al., "Roscotirine has anti-proliferative and pro-apoptotic effects on glioblastoma cell lines: A pilot study," Oncology Reports, 2015, 34:1549-1556, 8 pgs.
Konstan, M.W., et al., "Compacted DNA nanoparticles administered to the nasal mucosa of cystic fibrosis subjects are safe and demonstrate partial to complete cystic fibrosis transmembrane regulator reconstitution," Hum. Gene Ther., Dec. 2004, 15(12):1255-69, 15 pgs.
La Rosa PS, et al., "Hypothesis Testing and Power Calculations for Taxonomic-Based Human Microbiome Data," PLoS One, 2012, 7(12):e52078, 13 pgs.
Laguna TA, et al., "Sputum Desmosine During Hospital Admission for Pulmonary Exacerbation in Cystic Fibrosis," Chest, Dec. 2009, 136(6):1561-1568, 8 pgs.
Lancioni CL, et al., "*Mycobacterium tuberculosis* Lipoproteins Directly Regulate Human Memory CD4+ T Cell Activation via Toll-Like Receptors 1 and 2," Infect Immun, Feb. 2011, 79(2):663-673, 11 pgs.
Li Q, et al., "Rv2468c, a novel *Mycobacterium tuberculosis* protein that costimulates human CD4+ T cells through VLA-5," J Leukoc Biol, Feb. 2012, 91(2):311-20, 10 pgs.
Liou TG, et al., "Year-to-year changes in lung function in individuals with cystic fibrosis," J Cyst Fibros, 2010, 9(4):250-6, 7 pgs.
Naso, M.F., et al., "Adeno-Associated Virus (AAV) as a Vector for Gene Therapy," Bio Drugs, Jul. 1, 2017, 31:317-334, 18 pgs.
Nick JA, et al., "Blood mRNA biomarkers for detection of treatment response in acute pulmonary exacerbations of cystic fibrosis," Thorax, 2013, 68(10):929-937, 9 pgs.
Obuchowski NA, et al., "Sample Size Determination for Diagnostic Accuracy Studies Involving Binormal ROC Curve Indices," Stat Med, 1997, 16(13):1529-1542, 14 pgs.
Peila, C., et al., "Effects of Holder pasteurization on the protein profile of human milk, " Italian journal of Pediatrics, 2016, 42:36, 8 pgs.
Peng, J., et al., "A Geometric Approach to Maximum Likelihood Estimation of the Functional Principal Components From Sparse Longitudinal Data," J Comput Graph Stat, 2009, 18(4):995-1015, Technical Report 2007a, 87 pgs.
Peng, J., Restricted MLE for Functional Principal Components Analysis (R package fpca) 2015. Available from: https://CRAN.R-project.org/package=fpca, 12 pgs.
Ramsay JO, et al., Functional data analysis, Second Ed., Springer Science + Business Media, Inc., New York, NY, 2005, p. 426, (Table of Contents only) 13 pgs.
Ratjen F, et al., "Effect of Azithromycin on Systemic Markers of Inflammation in Patients With Cystic Fibrosis Uninfected With *Pseudomonas aeruginosa*," Chest, 2012, 142(5):1259-1266, 8 pgs.
Rosenfeld M, et al., "Baseline Characteristics and Factors Associated With Nutritional and Pulmonary Status at Enrollment in the Cystic Fibrosis EPIC Observational Cohort," Pediatr Pulmonol, 2010, 45(9):934-944, 11 pgs.
Rosenfeld M, et al., "Decline in Lung Function Does not Predict Future Decline in Lung Function in Cystic Fibrosis Patients," Pediatr Pulmonol, 2015, 50(9):856-862, 7 pgs.
Sagel SD, et al., "Effect of Treatment of Cystic Fibrosis Pulmonary Exacerbations on Systemic Inflammation," Ann Am Thorac Soc, 2015, 12(5):708-717, 10 pgs.
Sagel SD, et al., "Validation of Candidate Serum Protein and Lipid Markers of Disease Severity In CF," Pediatr Pulmonol, 2014, 49(S38):288, 2014 Cystic Fibrosis Conference, Poster Session Abstract 205*, 1 pg.
Sanders DB, et al., "Failure to Recover to Baseline Pulmonary Function after Cystic Fibrosis Pulmonary Exacerbation," Am J Respir Crit Care Med, 2010, 182(5):627-632, 6 pgs.
Schluchter MD, et al., "Classifying Severity of Cystic Fibrosis Lung Disease Using Longitudinal Pulmonary Function Data," Am J Respir Crit Care Med, 2006, 174(7):780-786, 7 pgs.
Sinha C, et al., "PKA and actin play critical roles as downstream effectors in MRP4-mediated regulation of fibroblast migration," Cell Signal, 2015, 27(7):1345-1355, 11 pgs.
Sinha C, et al., "Capturing the Direct Binding of CFTR Correctors to CFTR by Using Click Chemistry," Chembiochem, 2015, 16:2017-2022, 6 pgs.
Slobodianik NH, et al., "Inflammatory biomarker profile in children with cystic fibrosis: preliminary study," Proc Nutr Soc, $3^{rd}$ International Immunonutrition Workshop; Session 4: Dietary strategies to prevent and mitigate inflammatory diseases, 2010, 69(3):354-356, 3 pgs.
Sun, W., et al., "Real-Time Imaging of Gene Delivery and Expression with DNA Nanoparticle Technologies," Chapter 33, In: Foote R., Lee J. (eds) Micro and Nano Technologies in Bioanalysis. Methods in Molecular Biology (Methods and Protocols), Humana Press, Totowa, NJ Methods Mol Biol, 2009, 544:525-546.
Szczesniak RD, et al., "A semiparametric approach to estimate rapid lung function decline in cystic fibrosis," Annals of Epidemiology, 2013, 23(12):771-777, 7 pgs.
Szczesniak RD, et al., "Phenotypes of Rapid Cystic Fibrosis Lung Disease Progression during Adolescence and Young Adulthood," American Journal of Respiratory and Critical Care Medicine, 2017, 196(4): 471-478, 8 pgs.
Szczesniak RD, et al., "Predicting Future Lung Function Decline in Cystic Fibrosis Patients: Statistical Methods and Clinical Connections," Pediatr Pulmonol, Letter to the Editor, 2016, 51(2):217-218, 2 pgs.
Tang Y, et al., "Developing Adaptive Personalized Therapy for Cystic Fibrosis Using Reinforcement Learning," Submitted to Ann Appl Stat, 2012, 28 pgs.
Taylor-Robinson D, et al., "Understanding the natural progression in %$FEV_1$ decline in patients with cystic fibrosis: a longitudinal study," Thorax, 2012, 67(10):860-866, 7 pgs.
Tibshirani RJ., "Regression Shrinkage and Selection via the Lasso," J R Statist Soc B, 1996, 58(1):267-288, 22 pgs.
Tucholska M, et al., "Human Serum Proteins Fractionated by Preparative Partition Chromatography Prior to LC-ESI-MS/MS," J Proteome Res, 2009, 8(3):1143-1155, 13 pgs.
Verbeke G, et al., "The analysis of multivariate longitudinal data: A review," Stat Methods Med Res, 2014, 23(1):42-59, 18 pgs.
Wainwright CE, et al., "Lumacaftor-Ivacaftor in Patients with Cystic Fibrosis Homozygous for Phe508del CFTR," N Engl J Med, 2015, 373(3):220-231, 12 pgs.

(56) References Cited

OTHER PUBLICATIONS

Wang J, et al., "Measuring the impact of apnea and obesity on circadian activity patterns using functional linear modeling of actigraphy data," J Circadian Rhythms, 2011, 9(1):11, 10 pgs.

Wang X, et al., "Hsp90 Cochaperone Aha1 Downregulation Rescues Misfolding of CFTR in Cystic Fibrosis," Cell, 2006, 127(4):803-815, 13 pgs.

Wolff, M.E., (ed.), Burger's Medicinal Chemistry and Drug Discovery, 5th ed., 1995, pp. 172-178, 949-982, 41 pgs.

Xu, Z., et al., "Knocking down necleolin expression in gliomas inhibits tumor growth and induces cell cycle arrest," J Neurooncol, 2012, 108:59-67, 9 pgs.

Yanagisawa K, et al., "Proteomic patterns of tumour subsets in non-small-cell lung cancer," Lancet, 2003, 362(9382):433-439, 7 pgs.

Yao, F., et al., "Functional Data Analysis for Sparse Longitudinal Data," Journal of the American Statistical Association, 2005, 100(470):577-590, 14 pgs.

Yurek, D.M., et al., "Compacted DNA nanoparticle gene transfer of GDNF to the rat striatum enhances the survival of grafted fetal dopamine neurons," Cell Transplant., 2009, 18(10):1183-96, 15 pgs.

Yurek, D.M., et al., "DNA Nanoparticles: Detection of Long-term Transgene Activity in Brain Using Bioluminescence Imaging," Mol. Imaging, Apr. 26, 2011, 10(5):327-339, 12 pgs.

Yurek, D.M., et al., "Long-term transgene expression in the central nervous system using DNA nanoparticles," Mol. Ther., Apr. 2009, 17(4):641-50, 14 pgs.

Zeitzer JM, et al., "Phenotyping Apathy in Individuals With Alzheimer Disease Using Functional Principal Component Analysis," Am J Geriatr Psychiatry, 2013, 21(4):391-397, 12 pgs.

Zemanick ET, et al., "Inflammation and Airway Microbiota During Cystic Fibrosis Pulmonary Exacerbations," PLoS One, 2013, 8(4):e62917, 13 pgs.

Zhang, X., et al., "CRISPR/Cas9 system: a powerful technology for in vivo and ex vivo gene therapy," Sci. China Life Sci, May 2017, 60(5):468-75, 8 pgs.

Ziady, A.G., et al., "Current prospects for gene therapy of cystic fibrosis," Curr Opin Pharmacol, Oct. 2006, 6(5):515-21, 7 pgs.

Ziady, A.G., et al., "Functional evidence of CFTR gene transfer in nasal epithelium of cystic fibrosis mice in Vivo following luminal application of DNA complexes targeted to the serpin-enzyme complex receptor," Mol. Ther., Apr. 2002, 5(4):413-9, 7 pgs.

Ziady AG, et al., "Interaction with CREB binding protein modulates the activities of Nrf2 and NF-κB in cystic fibrosis airway epithelial cells," Am J Physiol Lung Cell Mol Physiol, 2012, 302(11):L1221-L1231, 11 pgs.

Ziady, A.G., et al., "Non-viral gene transfer therapy for cystic fibrosis," Expert Opin Biol Ther, Jun. 2003, 3(3):449-58, 10 pgs.

Ziady AG, et al., "Protein Sequencing with Tandem Mass Spectrometry," Chapter 21, James Weifu Lee, et al., Eds. Micro and Nano Technologies in Bioanalysis, Methods Mol Biol, 2009, 544:325-341, 17 pgs.

Ziady AG, et al., "Proteomic Analyses of BALF Reveal Potential Biomarkers and Suggest Altered Lipid, Cyclic Nucleotide, and Iron Metabolism in Young CF Children Versus Disease Controls," Pediatr Pulmonol, 2013, 48(S36):277-278, 2013 Cystic Fibrosis Conference, Poster Session Abstract 204*, 2 pgs.

Ziady AG, et al., "Proteomic Analyses of Serum From CF Patients With Mild or Severe Disease Reveal the Differential Expression of Proteins That Regulate the Differentiation of Cartilage, Myeloid Leukocytes, and Intestinal Epithelia" Pediatr Pulmonol, 2014, 49(S38):288, 2014 Cystic Fibrosis Conference, Poster Session Abstract 206*, 1 pg.

International Search Report and Written Opinion dated Aug. 10, 2020 for Application No. PCT/US2020/030401, 10 pgs.

U.S. Appl. No. 17/121,835, filed Dec. 15, 2020, by Ziady et al., entitled: "Compositions and Methods for Nucleic Acid Transfer."

Brody, A.S., et al., "High-Resolution Computed Tomography in Young patients with Cystic Fibrosis: Distribution of Abnormalities and Correlation with Pulmonary Function Tests," J Peds, 2004, 145(1):32-38, 7 pgs.

Chassagnon, G., et al., "Long-term computed tomographic changes in cystic fibrosis patients treated with ivacaftor," Eur Respir J, 2016, 48(1):249-252, 4 pgs.

Deboer, E.M., et al., "Proteomic profiling identifies novel circulating markers associated with bronchiectasis in cystic fibrosis," Proteomics Clin Appl, 2017, 11(9-10):1600147, 9 pgs.

Deboer, E.M., et al., "Novel Application of Aptamer Proteomic Analysis in Cystic Fibrosis Bronchoalveolar Lavage Fluid," Proteomics Clin Appl, 2019, 13:1800085, 8 pgs.

Eichinger, M., et al., "Morphologic and functional scoring of cystic fibrosis lung disease using MRI," European Journal of Radiology, 2012, 81(6): 1321-1329, 9 pgs.

Fagerland, M.W., et al., "The McNemar test for binary matched-pairs data: mid-p and asymptotic are better than exact conditional," BMC Med Res Methodol, 2013, 13:91, 8 pgs.

Guo, J., et al., "Longitudinal free-breathing MRI measurement of murine lung physiology in a progressive model of lung fibrosis," J Appl Physio, 2019, 126(4):1138-1149, 12 pgs.

Hanania, N.A., et al., "Acute bronchodilator responsiveness and health outcomes in COPD patients in the UPLIFT trial," Respiratory Research, 2011, 12(1):6, 11 pgs.

Higano, N.S., et al., "Retrospective respiratory self-gating and removal of bulk motion in pulmonary UTE MRI of neonates and adults," Magn Reason Med, 2017, 77(3):1284-1295, 25 pgs.

Higuchi, T., and V. Stella (Eds.), Pro-drugs as Novel Drug Delivery Systems, ACS Symposium Series 14, American Chemical Society, Washington, D.C., 1975, 6 pgs. [Bibliographic data only].

Hoy, S.M., "Elexacaftor/Ivacaftor/Tezacaftor: First Approval," Drugs, 2019, 79(18):2001-2007, 7 pgs.

King, T.E., et al., "A Phase 3 Trial of Pirfenidone in Patients with Idiopathic Pulmonary Fibrosis," N Engl J Med, 2014, 370(22):2083-2092, 10 pgs.

Konstan, M.W., et al., "Assessment of safety and efficacy of long-term treatment with combination lumacaftor and ivacaftor therapy in patients with cystic fibrosis homozygous for the F508del-CFTR mutation (PROGRESS): a phase 3, extension study," Lancet Respir Med, 2017, 5(2):107-118, 12 pgs.

Lederlin, M., et al., "Three-Dimensional Assessment of Lung Tissue Density Using a Clinical Ultrashort Echo Time at 3 Tesla: A Feasibility Study in Healthy Subjects," J Magn Reson Imag, 2014, 40(4):839-847, 9 pgs.

Loew, W., et al., "A Volume Saddle Coil for Hyperpolarized $^{129}$Xe Lung Imaging," Proc Int Soc Magn Reson Med, 2015, 23:1507, 1 pg. [Abstract only].

Miller, G.W., et al., "Hyperpolarized $^3$He lung ventilation imaging with $B_1$-inhomogeneity correction in a single breath-hold scan," MAGMA, 2004, 16(5):218-226, 9 pgs.

Niedbalski, P.J., et al., "Mapping and correcting hyperpolarized magnetization decay with radial keyhole imaging," Magn Reson Med, 2019, 82:367-376, 10 pgs.

Pearce, M.S., et al., "Radiation exposure from CT scans in childhood and subsequent risk of leukaemia and brain tumours: a retrospective cohort study," Lancet, 2012, 380(9840):499-505, 7 pgs.

Pipe, J.G., et al., "A New Design and Rationale for 3D Orthogonally Oversampled κ-Space Trajectories," Magn Reson Med, 2011, 66(5):1303-1311, 9 pgs.

Roach, D.J., et al., "Ultrashort Echo-Time Magnetic Resonance Imaging Is a Sensitive Method for the Evaluation of Early Cystic Fibrosis Lung Disease," Ann Am Thorac Soc, 2016, 13(11): 1923-1931, 9 pgs.

Robison, R.K., et al., "Three-Dimensional Ultrashort Echo-Time Imaging Using a FLORET Trajectory," Magn Reson Med, 2017, 78(3):1038-1049, 12 pgs.

Roche, E.B., (Ed.), Bioreversible Carriers in Drug Design: Theory and Application, American Pharmaceutical Association, 1987, Pergamon Press, New York, 4 pgs. [Table of Contents only].

(56) References Cited

OTHER PUBLICATIONS

Sawicki, G.S., et al., "Sustained Benefit from Ivacaftor Demonstrated by Combining Clinical Trial and Cystic Fibrosis Patient Registry Data," Am J Respir Crit Care Med, 2015, 192(7):836-842, 7 pgs.

Stanojevic, S., et al., "Physiologic endpoints for clinical studies for cystic fibrosis," J Cyst Fibros, 2016, 15(4):416-423, 8 pgs.

Szczesniak, R.D., et al., "Dynamic predictive probabilities to monitor rapid cystic fibrosis disease progression," Statistics in Medicine, 2020, 39(6):740-756, 17 pgs.

Szczesniak, R.D., et al., "Improving Detection of Rapid Cystic Fibrosis Disease Progression—Early Translation of a Predictive Algorithm Into a Point-of-Care Tool" IEEE Journal of Translational Engineering in Health and Medicine, Point-of-Care Technologies, 2019, 7:2800108, 8 pgs.

Szczesniak, R., et al., "Use of $FEV_1$ in Cystic Fibrosis Epidemiologic Studies and Clinical Trials: A Statistical Perspective for the Clinical Researcher," J Cyst Fibros, 2017, 16(3):318-326, 17 pgs.

Tepper, L.A., et al., "The development of bronchiectasis on chest computed tomography in children with cystic fibrosis: can prestages be identified?" Eur Radiol, 2016, 26(12):4563-4569, 7 pgs.

Thomen, R.P., et al., "Hyperpolarized $^{129}$Xe for investigation of mild cystic fibrosis lung disease in pediatric patients," J Cyst Fibros, 2017, 16(2):275-282, 8 pgs.

Vestbo, J., et al., "Natural history of COPD: Focusing on change in $FEV_1$," Respirology, 2016, 21(1):34-43, 10 pgs.

Walkup, L.L., et al., "Feasibility, tolerability and safety of pediatric hyperpolarized $^{129}$Xe magnetic resonance imaging in healthy volunteers and children with cystic fibrosis," Pediatr Radiol, 2016, 46(12):1651-1662, 23 pgs.

Walkup, L.L., et al., "Xenon-129 MRI detects ventilation deficits in pediatric stem-cell transplant patients unable to perform spirometry," Eur Respir J, 2019, 53(5):1-16, 16 pgs.

Wielputz, M.O., et al., "Magnetic Resonance Imaging Detects Changes in Structure and Perfusion, and Response to Therapy in Early Cystic Fibrosis Lung Disease," Am J Respir Crit Care Med, 2014, 189(8):956-965, 10 pgs.

Wilcoxon, F., "Individual Comparisons of Grouped Data by Ranking Methods," Journal of Economic Entomology, 1946, 39(2):269-270, 2 pgs.

Willmering, M.M., et al., "Implementation of the FLORET Ultrashort Echo-Time Sequence for Lung Imaging," Magn Reson Med, 2019, 82(3):1091-1100, 17 pgs.

Willmering, M.M., et al., "Improved pulmonary $^{129}$Xe ventilation imaging via 3D-spiral UTE MRI," Magn Reson Med, 2020, 84(1):312-320, 14 pgs.

Yu, J., et al., "Comparison of Lung $T_2$* During Free-Breathing at 1.5 T and 3.0 T with Ultrashort Echo Time Imaging," Magn Reson Med, 2011, 66(1):248-254, 7 pgs.

Zwart, N.R., et al., "Graphical Programming Interface: A Development Environment for MR1 Methods.," Magn Reson Med, 2015, 74(5):1449-1460, 12 pgs.

Altieri, D.C., "Validating Survivin as a Cancer Therapeutic Target," Nat Rev Cancer, 2003, 3(1):46-54, 9 pgs.

Arai, H., et al., "Nestin expression in brain tumors: its utility for pathological diagnosis and correlation with the prognosis of high-grade gliomas," Brain Tumor Pathol, 2012, 29(3): 160-167, 8 pgs.

Assi, H., et al., "Gene Therapy for Brain Tumors: Basic Developments and Clinical Implementation," Neurosci Lett, 2012, 527(2):71-77, 14 pgs.

Bhang, H.-E.C., et al., "Tumor-Specific Imaging Through Progression Elevated Gene-3 Promoter-Driven Gene Expression," Nat Med, 2011, 17(1):123-129, 16 pgs.

Bossen, C., et al., "Interactions of Tumor Necrosis Factor (TNF) and TNF Receptor Family Members in the Mouse and Human," J Biol Chem, 2006, 281(20):13964-13971, 8 pgs.

Chen, X., et al., "Cell Surface Nucleolin Serves as Receptor for DNA Nanoparticles Composed of Pegylated Polylysine and DNA," Mol Ther, 2008, 16(2):333-342, 10 pgs.

Christensen, C.L., et al., "Targeted cytosine deaminase-uracil phosphoribosyl transferase suicide gene therapy induces small cell lung cancer-specific cytotoxicity and tumor growth delay," Clin Cancer Res, 2010, 16(8):2308-2319, 21 pgs.

Dachs, G.U., et al., "From bench to bedside for gene-directed enzyme prodrug therapy of cancer," Anti-Cancer Drugs, 2005, 16(4):349-359, 11 pgs.

Debinski, W., et al., "Convection-enhanced delivery for the treatment of brain tumors," Expert Rev Neurother, 2009, 9(10):1519-1527, 15 pgs.

Fan, X., et al., "hTERT Gene Amplification and Increased mRNA Expression in Central Nervous System Embryonal Tumors," Am J Pathol, 2003, 162(6):1763-1769, 7 pgs.

Fortin, S.P., et al., "Tumor Necrosis Factor-Like Weak Inducer of Apoptosis (TWEAK) Stimulation of Glioma Cell Survival Is Dependent Upon Akt2 Function," Mol Cancer Res, 2009, 7(11):1871-1881, 24 pgs.

Galzio, R., et al., "Glycosilated Nucleolin as Marker for Human Gliomas," J Cell Biochem, 2012, 113(2):571-579, 9 pgs.

Gurunathan, S., et al., "Regulation of Fibroblast Growth Factor-inducible 14 (Fn14) Expression Levels via Ligand-independent Lysosomal Degradation," J Biol Chem, 2014, 289(19):12976-12988, 13 pgs.

Han, Z., et al., "AAV and Compacted DNA Nanoparticles for the Treatment of Retinal Disorders: Challenges and Future Prospects," Invest Ophthalmol Vis Sci, 2011, 52(6):3051-3059, 9 pgs.

Haung, L., et al., "Highly Selective Targeting of Hepatic Stellate Cells for Liver Fibrosis Treatment Using a D-Enantiomeric Peptide Ligand of Fn14 Identified by Mirror-Image mRNA Display," Mol Pharmaceutics, 2017, 14:1742-1753, 12 pgs.

Hersh, D.S., et al., "The TNF receptor family member Fn14 is highly expressed in recurrent glioblastoma and in GBM patient-derived xenografts with acquired temozolomide resistance," Neuro Oncol, 2018, 20(10):1321-1330, 10 pgs.

Jiang, X., et al., "The Imprinted Gene PEG3 Inhibits Wnt Signaling and Regulates Glioma Growth," J Biol Chem, 2010, 285(11):8472-8480, 9 pgs.

Joo, K.M., et al., "Patient-Specific Orthotopic Glioblastoma Xenograft Models Recapitulate the Histopathology and Biology of Human Glioblastomas In Situ," Cell Rep, 2013, 3(1):260-273, 14 pgs.

Kajiwara, Y., et al., "Expression of Survivin in Astrocytic Tumors: Correlation with Malignant Grade and Prognosis," Cancer, 2003, 97(4):1077-1083, 7 pgs.

Kibbey, M.C., et al., "A 110-kD Nuclear Shuttling Protein, Nucleolin, Binds to the Neurite-Promoting IKVAV Site of Laminin-1," J Neurosci Res, 1995, 42(3):314-322, 9 pgs.

Li, A., et al., "Unsupervised Analysis of Transcriptomic Profiles Reveals Six Glioma Subtypes," Cancer Res, 2009, 69(5):2091-2099, 17 pgs.

Liu, G., et al., "Nanoparticles of Compacted DNA Transfect Postmitotic Cells," J Biol Chem, 2003, 278(35):32578-32586, 9 pgs.

Martens, T., et al., "Inhibition of Glioblastoma Growth in a Highly Invasive Nude Mouse Model Can Be Achieved by Targeting Epidermal Growth Factor Receptor but not Vascular Endothelial Growth Factor Receptor-2," Clin Cancer Res, 2008, 14(17):5447-5458, 12 pgs.

Mastorakos, P., et al., "Highly PEGylated DNA Nanoparticles Provide Uniform and Widespread Gene Transfer in the Brain," Adv Healthc Mater, 2015, 4(7):1023-1033, 24 pgs.

Mead, B.P., et al., "Novel Focused Ultrasound Gene Therapy Approach Noninvasively Restores Dopaminergic Neuron Function in a Rat Parkinson's Disease Model," Nano Lett, 2017, 17(6):3533-3542, 21 pgs.

Nance, E.A., et al., "A Dense Poly(ethylene glycol) Coating Improves Penetration of Large Polymeric Nanoparticles within Brain Tissue," Sci Transl Med, 2012, 4(149):149ra119, 18 pgs.

Ndesendo, V.M., "Convection-Enhanced Delivery of Neurotherapeutics," In: V. Pillay and Y.E. Choonara, (Eds.), *Advances in Neurotherapeutic Delivery Technologies*, vol. 8, UK: OMICS International, 2015, https://doi.org/10.4172/978-1-63278-036-2-037, www.esciencecentral.org/ebooks, 3 pgs. (Bibliographic information only).

(56) References Cited

OTHER PUBLICATIONS

Neeves, K.B., et al., "Dilation and degradation of the brain extracellular matrix enhances penetration of infused polymer nanoparticles," Brain Res, 2007, 1180:121-132, 23 pgs.

Negroni, L., et al., "Treatment of colon cancer cells using the cytosine deaminase/5-fluorocytosine suicide system induces apoptosis, modulation of the proteome, and Hsp90ß phosphorylation," Mol Cancer Ther, 2007, 6(10):2747-2756, 10 pgs.

O'Mahony, A.M., et al., "Non-viral Nanosystems for Gene and Small Interfering RNA Delivery to the Central Nervous System: Formulating the Solution," J Pharm Sci, 2013, 102(10):3469-3484, 16 pgs.

Ostrom, Q.T., et al., "CBTRUS Statistical Report: Primary Brain and Central Nervous System Tumors Diagnosed in the United States in 2006-2010," Neuro-Oncol, 2013, 15(Suppl 2):ii1-ii56, 56 pgs.

Patrizii, M., et al., "Utility of Glioblastoma Patient-Derived Orthotopic Xenografts in Drug Discovery and Personalized Therapy," Front Oncol, 2018, 8:article 23, 9 pgs.

Pelekanou, V., et al., "BAFF, APRIL, TWEAK, BCMA, TACI and Fn14 Proteins Are Related to Human Glioma Tumor Grade: Immunohistochemistry and Public Microarray Data Meta-Analysis," PLoS One, 2013, 8(12):e83250, 11 pgs.

Perez, J.G., et al., "The TWEAK Receptor Fn14 is a Potential Cell Surface Portal for Targeted Delivery of Glioblastoma Therapeutics," Oncogene, 2016, 35(17):2145-2155, 27 pgs.

Phillips, H.S., et al., "Molecular subclasses of high-grade glioma predict prognosis, delineate a pattern of disease progression, and resemble stages in neurogenesis," Cancer Cell, 2006, 9(3):157-173, 17 pgs.

Portsmouth, D., et al., "Suicide genes for cancer therapy," Mol Aspects Med, 2007, 28(1):4-41, 38 pgs.

Redgate, E.S., et al., "Time of Death of CNS Tumor-Bearing Rats Can Be Reliably Predicted by Body Weight-Loss Patterns," Lab Anim Sci, 1991, 41(3):269-273, 5 pgs.

Saucier-Sawyer, J.K., et al., "Distribution of Polymer Nanoparticles by Convection-Enhanced Delivery to Brain Tumors," J Control Release, 2016, 232:103-112, 26 pgs.

Sausville, E.A. et al., "Contributions of Human Tumor Xenografts to Anticancer Drug Development," Cancer Res, 2006, 66(7):3351-3354, discussion 3354, 4 pgs.

Schwartzbaum, J.A., et al., "Epidemiology and molecular pathology of glioma," Nat Clin Pract Neurol, 2006, 2(9):494-503, 10 pgs.

Shirahata, M., et al., "Gene Expression-Based Molecular Diagnostic System for Malignant Gliomas Is Superior to Histological Diagnosis," Clin Cancer Res, 2007, 13(24):7341-7356, 16 pgs.

Shirahata, M., et al., "Using gene expression profiling to identify a prognostic molecular spectrum in gliomas," Cancer Sci, 2009, 100(1):165-172, 8 pgs.

Shirakawa, T., et al., "Cytotoxicity of Adenoviral-Mediated Cytosine Deaminase Plus 5-Fluorocytosine Gene Therapy is Superior to Thymidine Kinase Plus Acyclovir in a Human Renal Cell Carcinoma Model," J Urol, 1999, 162(3 Pt 1):949-954, 6 pgs.

Soundararajan, S., et al., "Plasma Membrane Nucleolin Is a Receptor for the Anticancer Aptamer AS1411 in MV4-11 Leukemia Cells," Mol Pharmacol, 2009, 76(5):984-991, 8 pgs.

Taillandier, L., et al., "Models for neuro-oncological preclinical studies: solid orthotopic and heterotopic grafts of human gliomas into nude mice," J Neurosci Methods, 2003, 125(1-2):147-157, 11 pgs.

Tobias, A., et al., "The art of gene therapy for glioma: a review of the challenging road to the bedside," J Neurol Neurosurg Psychiatry, 2013, 84(2):213-222, 20 pgs.

Tran, N.L., et al., "Increased Fibroblast Growth Factor-Inducible 14 Expression Levels Promote Glioma Cell Invasion via Rac1 and Nuclear Factor-KB and Correlate with Poor Patient Outcome," Cancer Res, 2006, 66(19):9535-9542, 8 pgs.

Tran, N.L., et al., "The Human Fn14 Receptor Gene Is Up-Regulated in Migrating Glioma Cells in Vitro and Overexpressed in Advanced Glial Tumors," Am J Pathol, 2003, 162(4):1313-1321, 9 pgs.

Trinh, Q.T., et al., "Enzyme/Prodrug Gene Therapy: Comparison of Cytosine Deaminase/5-Fluorocytosine Versus Thymidine Kinase/ Ganciclovir Enzyme/Prodrug Systems in a Human Colorectal Carcinoma Cell Line," Cancer Res, 1995, 55(21):4808-4812, 5 pgs.

Vogelbaum, M.A et al., "Convection-enhanced delivery for the treatment of glioblastoma," Neuro-Oncol, 2015, 17(Suppl 2):ii3-ii8, 6 pgs.

Winkles, J.A., "The TWEAK-Fn14 cytokine-receptor axis: discovery, biology and therapeutic targeting," Nat Rev Drug Discov, 2008, 7(5):411-425, 32 pgs.

Workman, P., et al., "Guidelines for the welfare and use of animals in cancer research," Br J Cancer, 2010, 102(11):1555-1577, 23 pgs.

Xu, Z., et al., "Orthotopic Patient-Derived Glioblastoma Xenografts in Mice," Methods Mol Biol, Ch. 14 in Dimitris G. Placantonakis (ed.), *Glioblastoma: Methods and Protocols*, Springer Science+ Business Media, LLC, 2018, 1741:183-190, 8 pgs.

Yabroff, K.R., et al., "Patterns of care and survival for patients with glioblastoma multiforme diagnosed during 2006," Neuro-Oncol, 2012, 14(3):351-359, 9 pgs.

Yurek, D., et al., "Intracerebral injections of DNA nanoparticles encoding for a therapeutic gene provide partial neuroprotection in an animal model of neurodegeneration," Nanomedicine: Nanotechnology, Biology, and Medicine, 2017, 13(7):2209-2217, 9 pgs.

Yurek, D.M., et al., "Age and lesion-induced increases of GDNF transgene expression in brain following intracerebral injections of DNA nanoparticles," Neuroscience, 2015, 284:500-512, 28 pgs.

Zarogoulidis, P., et al., "Suicide Gene Therapy for Cancer—Current Strategies," J Genet Syndr Gene Ther, 2013, 4, 29 pgs.

Zhang, J., et al., "Gene-Directed Enzyme Prodrug Therapy," AAPS J, 2015, 17(1):102-110, 9 pgs.

Zhou, H., et al., "Development of Human Serine Protease-Based Therapeutics Targeting Fn14 and Identification of Fn14 as a New Target Overexpressed in TNBC," Mol Cancer Ther, 2014, 13(11):2688-2705, 34 pgs.

Ziady, A.-G., et al., "Minimal Toxicity of Stabilized Compacted DNA Nanoparticles in the Murine Lung," Mol Ther, 2003, 8(6):948-956, 9 pgs.

Ziady, A.-G., et al., "Transfection of Airway Epithelium by Stable PEGylated Poly-$_L$-lysine DNA Nanoparticles in Vivo," Mol Ther, 2003, 8(6):936-947, 12 pgs.

European Search Report, Extended, and Written Opinion dated Dec. 14, 2021 for Application No. EP 21180569.2, 11 pgs.

Abedin, S., et al., "Predictive Value of Bronchiolitis Obliterans Syndrome Stage 0p in Chronic Graft-versus-Host Disease of the Lung," Biol Blood Marrow Transplant, 2015, 21(6):1127--1131, 15 pgs.

Amanat, F., et al., "A serological assay to detect SARS-CoV-2 seroconversion in humans," Nat. Med, 2020, 26(7):1033-1036, 16 pgs.

Aurora, P., et al.," Quality Control for Spirometry in Preschool Children with and without Lung Disease," Am J Respir Crit Care Med, 2004, 169:1152-1159, 8 pgs.

Aziz, M.D., et al., "Disease Risk and GVHD Biomarkers Can Stratify Patients For Risk of Relapse and Non-Relapse Mortality Post Hematopoietic Cell Transplant," Leukemia, 2020, 34(7):1898-1906, 17 pgs.

Benden, C., et al., "Therapy options for chronic lung allograft dysfunction-bronchioliolitis obliterans syndrome following first-line immunosuppressive strategies: A systematic review," Jounral of Heart and Lung Transplantation, 2017, 36(9):921-933, 13 pgs.

Bergeron, A., et al., "Noninfectious lung complications after allogeneic haematopoietic stem cell transplantation," Eur Respir J, 2018, 51:1702617, 13 pgs.

Brewington, J.J., et al., "Detection of CFTR function and modulation in primary human nasal cell spheroids," J Cyst Fibros, 2018, 17(1):26-33, 17 pgs.

Callow, K.A., et al., "The time course of the immune response to experimental coronavirus infection of man," Epidemiol Infect, 1990, 105:435-446, 12 pgs.

Casadevall, A., et al., "The convalescent sera option for containing COVID-19," J Clin Invest, 2020, 130(4):1545-1548.

Centers for Disease Control and Prevention (CDC) Revised U.S. surveillance case definition for severe acute respiratory syndrome

(56) References Cited

OTHER PUBLICATIONS (SARS) and update on SARS cases-United States and worldwide, Dec. 2003. MMWR Morb. Mortal. Wkly. Rep., 2003, 52, 1202-1206, 6 pgs.

Chang, C.-K., et al., "Multiple Nucleic Acid Binding Sites and Intrinsic Disorder of Severe Acute Respiratory Syndrome Coronavirus Nucleocapsid Protein: Implications for Ribonucleocapsid Protein Packaging," J Virol, 2009, 83(5):2255-2264, 10 pgs.

Cheng, G.-S., et al., "Lung Function Trajectory in Bronchiolitis Obliterans Syndrome after Allogeneic Hematopoietic Cell Transplant," Ann Am Thorac Soc, 2016; 13(11):1932-1939, 8 pgs.

Chi, X., et al., "A neutralizing human antibody binds to the N-terminal domain of the Spike protein of SARS-CoV-2," Science, 2020, 369:650-655, 6 pgs.

Chien, J.W., et al., "Bronchiolitis Obliterans Syndrome After Allogeneic Hematopoietic Stem Cell Transplantation: An Increasingly Recognized Manifestation of Chronic Graft-versus-Host Disease," Biol Blood Marrow Transplant, 2010, 16(1):S106-S114, 9 pgs.

Cohen, H.Y., et al., "Calorie Restriction Promotes Mammalian Cell Survival by Inducing the SIRT1 Deacetylase," Science, 2004, 305(5682):390-392.

Cox, D.R., et al., "Large numbers of explanatory variables, a semi-descriptive analysis," PNAS, 2017, 114(32):8592-8595, 4 pgs.

De Silva, T., et al., "Markers of rejection of a lung allograft: state of the art," Biomark Med, 2022, 16(6):483-498, 16 pgs.

Deeks, J.J., et al. "Antibody tests for identification of current and past infection with SARS-CoV-2 (Review)," Cochrane Database Syst Rev, 2020, 6:CD013652, 306 pgs.

Dijkman, R., et al., "Human Coronavirus NL63 and 229E Seroconversion in Children," J Clin Microbiol, 2008, 46(7):2368-2373, 6 pgs.

Du, L., et al., "The spike protein of SARS-CoV—a target for vaccine and therapeutic development," Nat Rev Microbiol, 2009, 7:226-236, 11 pgs.

Dunn, M., et al., "Pediatric Bone Marrow Transplant Recipients That Develop Bronchiolitis Obliterans Syndrome Exhibit Significant Changes in Complement Activation, Angiotensin Maturation, and Cholesterol Processing Prior to Clinical Diagnosis," Am J Respir Crit Care Med, 2021, 203(9):A3281 (Abstract), 2 pgs.

Eroshenko, N., et al., "Implications of antibody-dependent enhancement of infection for SARS-CoV-2 countermeasures," Nat Biotechnol, 2020, 38:789-791, 3 pgs.

Estenne, M., et al., "Bronchiolitis Obliterans Syndrome 2001: An Update of the Diagnostic Criteria," J Heart Lung Transplant, 2002; 21:297-310, 14 pgs.

Fink, Z.W., et al., "PepSIRF: a flexible and comprehensive tool for the analysis of data from highly-multiplexed DNA-barcoded peptide assays," arXiv, 2020, 5 pgs.

Fleri, W., et al., "The Immune Epitope Database and Analysis Resource in Epitope Discovery and Synthetic Vaccine Design," Front Immunol, 2017, 8:278, 16 pgs.

Friesen, R.H.E., et al., "A common solution to group 2 influenza virus neutralization," PNAS, 2014, 111(1):445-450, 6 pgs.

Geyer, P.E., et al., "Plasma Proteome Profiling to Assess Human Health and Disease," Cell Syst, 2016, 2:185-195, 12 pgs.

Geyer, P.E., et al., "Proteomics reveals the effects of sustained weight loss on the human plasma proteome," Mol Syst Biol, 2016; 12:901, 16 pgs.

Gorse, G.J., et al., "Prevalence of Antibodies to Four Human Coronaviruses is Lower in Nasal Secretions than in Serum," Clin Vaccine Immunol, 2010, 17(12):1875-1880, 6 pgs.

Gostic, K.M., et al., "Potent Protection against H5N1 and H7N9 Influenza via Childhood Hemagglutinin Imprinting," Science, 2016, 354(6313):722-726, 16 pgs.

Grassi, N., et al., "Ultra-deep and quantitative saliva proteome reveals dynamics of the oral microbiome," Genome Med, 2016, 8:44, 13 pgs.

Grifoni, A., et al., "Targets of T Cell Responses to SARS-CoV-2 Coronavirus in Humans with COVID-19 Disease and Unexposed Individuals," Cell, 2020, 181:1489-1501, 29 pgs.

Halstead, S.B., et al., "Antibody-enhanced dengue virus infection in primate leukocytes," Nature, 1977, 265:739-741, 3 pgs.

Hansen, J., et al., "Studies in humanized mice and convalescent humans yield a SARS-CoV-2 antibody cocktail," Science, 2020, 369:1010-1014, 5 pgs.

Hartwell, M.J., et al., "An early-biomarker algorithm predicts lethal graft-versus-host disease and survival," JCI Insight, 2017, 2(3):e89798, 9 pgs.

Heijerman, H.G.M., et al., "Efficacy and safety of the elexacaftor/tezacaftor/ivacaftor combination regimen in people with cystic fibrosis homozygous for the F508del mutation: a double-blind, randomised, phase 3 trial," Lancet, 2019, 394(10212):1940-1948, 21 pgs.

Heltshe, S.L., et al., "Ivacaftor-treated Patients with Cystic Fibrosis Derive Long-Term Benefit Despite No Short-Term Clinical Improvement," Am J Respir Crit Care Med, 2018, 197(11): 1483-1486, 4 pgs.

Hildebrandt, G.C., et al., "Diagnosis and treatment of pulmonary chronic GVHD: report from the consensus confrence on clinical practice in chronic GVHD," Bone Marrow Transplant, 2011, 46(10):1283-1295, 13 pgs.

Hoofnagle, J.H., et al., "Antibody to Hepatitis B Core Antigen. A Sensitive Indicator of Hepatitis B Virus Replication," N Engl J Med, 1974, 290:1336-1340, 5 pgs.

Huttenhain, R., et al., "A Targeted Mass Spectrometry Strategy for Developing Proteomic Biomarkers: A Case Study of Epithelial Ovarian Cancer," Mol Cell Proteomics, 2019, 18:1836-1850, 16 pgs.

Jagasia, M.H., et al., "National Institutes of Health Consensus Development Project on Criteria for Clinical Trials in Chronic Graft-versus-Host Disease: I. The 2014 Diagnosis and Staging Working Group Report," Biol Blood Marrow Transplant, 2015, 21(3):389-401.e1, 27 pgs.

Jia, N., et al., "Emergence of human infection with Jingmen tick virus in China: A retrospective study," EBioMedicine, 2019, 43:317-324, 8 pgs.

Jodele, S., et al., "Complement blockade for TA-TMA: lessons learned from a large pediatric cohort treated with eculizumab," Blood, 2020, 135(13):1049-1057, 9 pgs.

Jodele, S., et al., "Interferon-complement loop in transplant-associated thrombotic microangiopathy," Blood Adv, 2020, 4(6):1166-1177, 12 pgs.

Kall, L., et al., "Semi-supervised learning for peptide identification from shotgun proteomics datasets," Nat Methods, 2007, 4(11):923-925, 3 pgs.

Katzelnick, L.C., et al., "Antibody-dependent enhancement of severe dengue disease in humans," Science, 2017, 358:929-932, 4 pgs.

Keng, C.-T., et al., "Amino Acids 1055 to 1192 in the S2 Region of Severe Acute Respiratory Syndrome Coronavirus S Protein Induce Neutralizing Antibodies: Implications for the Development of Vaccines and Antiviral Agents," J Virol, 2005, 79(6):3289-3296, 8 pgs.

Keogh, R.H., et al., "Dynamic Predication of Survival in Cystic Fibrosis: A Landmarking Analysis Using UK Patient Registry Data," Epidemiology, 2019, 30(1):29-37, 9 pgs.

Khan, S., et al., "Analysis of Serologic Cross-Reactivity Between Common Human Coronaviruses and SARS-CoV-2 Using Coronavirus Antigen Microarray," bioRxiv, 2020, 10 pgs.

Khurana, S., et al., "Vaccine-Induced Anti-HA2 Antibodies Promote Virus Fusion and Enhance Influenza Virus Respiratory Disease," Sci Transl Med, 2013, 5(200):200ra114, 10 pgs.

Konstan, M.W., et al., "Risk Factors For Rate of Decline in Forced Expiratory Volume in One Second in Children and Adolescents with Cystic Fibrosis," J Pediatr, 2007, 151(2): 134-139e1, 7 pgs.

Konstan, M.W., et al., "Risk Factors For Rate of Decline in $FEV_1$ in Adults with Cystic Fibrosis," J Cyst Fibros, 2012, 11(5):405-411, 15 pgs.

Kozlov, I.A., et al., "A Highly Scalable Peptide-Based Assay System for Proteomics," PLoS One, 2012, 7(6):e37441, 10 pgs.

Krammer, F., et al., "Serology assays to manage COVID-19: Measurement of antibodies to SAR-CoV-2 will improve disease management if used correctly," Science, 2020, 368(6495):1060-1061, 2 pgs.

(56) References Cited

OTHER PUBLICATIONS

Krisp, C., et al., "Proteomic phenotyping of metastatic melanoma reveals putative signatures of MEK inhibitor response and prognosis," Br J Cancer, 2018; 119:713-723, 11 pgs.
Ku, N-O., et al., "Mutation of Human Keratin 18 in Association with Cryptogenic Cirrhosis," J Clin Invest, 1997, 99(1):19-23, 5 pgs.
Lai, S.-C., et al., "Characterization of neutralizing monoclonal antibodies recognizing a 15-residues epitope on the spike protein HR2 region of severe acute respiratory syndrome coronavirus (SARS-CoV)," J Biomed Sci, 2005, 12:711-727, 17 pgs.
Larman, H.B., et al. "Application of a synthetic human proteome to autoantigen discovery through PhIP-Seq," Nat Biotechnol, 2011, 29(6):535-541, 19 pgs.
Le, T.T., et al., "The COVID-19 vaccine development landscape," Nat Rev Drug Discov, 2020, 19:305-306, 2 pgs.
Lederer, D.J., et al., "Control of Confounding and Reporting of Results in Casual Inference Studies: Guidance for Authors form Editors of Respiratory, Sleep, and Critical Care Journals," Ann Am Thorac Soc, 2019, 16(1):22-28, 8 pgs.
Li, D., et al., "Flexible semiparametric joint modeling: an application to estimate individual long function decline and risk of pulmonary exacerbations in cystic fibrosis," Emerg Themes Epidemiol, 2017, 14:13, 13 pgs.
Liu, A., et al., "Antibody responses against SARS-CoV-2 in COVID-19 patients," J Med Virol, 2021, 93:144-148, 5 pgs.
Liu, S., et al., "Interaction between heptad repeat 1 and 2 regions in spike protein of SARS-associated coronavirus: implications for virus fusogenic mechanism and identification of fusion inhibitors," Lancet, 2004, 363:938-947, 10 pgs.
Liu, X., et al., "Proteomic Characterization Revels That MMP-3 Correlates With Bronchioliitits Obliterans Syndrome Following Allogeneic Hematopoietic Cell and Lung Transplantation," Am J Transplant, 2016, 16(8):2342-2351, 28 pgs.
Lounder, D.T., et al., "Lower levels of vitamin A are associated with increased gastrointestinal graft-versus-host disease in children," Blood, 2017, 129(20):2801-2807, 7 pgs.
Lu, R., et al., "Genomic characterisation and epidemiology of 2019 novel coronavirus: implications for virus origins and receptor binding," Lancet, 2020, 395:565-574, 10 pgs.
Lubroth, J., et al., "Absence of protein 2C from clarified foot-and-mouth disease virus vaccines provides the basis for distinguishing convalescent from vaccinated animals," Vaccine, 1996, 14(5):419-427, 9 pgs.
Lucchese, G., et al., "Peptidology: short amino acid modules in cell biology and immunology," Amino Acids, 2007, 33:703-707, 5 pgs.
Luebbering, N., et al., "Endothelial injury, F-actin and vitamin D binding protein after hematopoietic stem cell transplant and association with clinical outcomes," Haematologica, 2021, 106(5):1321-1329, 9 pgs.
Lv, H., et al., "Cross-reactive Antibody Response between SARS-CoV-2 and SARS-CoV Infections," Cell Rep, 2020, 31:107725, 10 pgs.
Magi, B et al., "Bronchoalveolar lavage fluid protein composition in patients with sarcoidosis and idiopathic pulmonary fibrosis: A two-dimensional electrophoretic study," Electrophoresis, 2002, 23:3434-3444, 11 pgs.
Major-Monfried, H., et al., "MAGIC biomarkers predict long-term outcomes for steroid-resistant acute GVHD," Blood, 2018, 131(25):2846-2855, 10 pgs.
Middleton, P.G., et al., "Elexacaftor-Tezacaftor-Ivacaftor for Cystic Fibrosis with a Single Phe508del Allele," N Engl J Med, 2019, 381(19):1809-1819, 16 pgs.
Mina, M.J., et al., "Measles virus infection diminishes preexisting antibodies that offer protection from other pathogens," Science, 2019, 366(6465):599-606, 18 pgs.
Monto, A.S., et al., "The Doctrine of Original Antigenic Sin: Separating Good From Evil," J Infect Dis, 2017, 215:1782-1788, 7 pgs.
Muhlebach, M.S, et al., "Biomarkers for Cystic Fibrosis Drug Development," J Cyst Fibros, 2016, 15(6):714-723, 20 pgs.
Ni, L., et al., "Detection of SARS-CoV-2-Specific Humoral and Cellular Immunity in COVID-19 Convalescent Individuals," Immunity, 2020, 52:971-977, 11 pgs.
Nichols, D.P., et al., "The triterpenoid CDDO limits inflammation in preclinical models of cystic fibrosis lung disease," Am J Physiol Lung Cell Mol Physiol, 2009, 297(5):L828-L836, 9 pgs.
Nie, J., et al., "Establishment and validation of a pseudovirus neutralization assay for SARS-CoV-2," Emerg Microbes Infect, 2020, 9:680-686, 7 pgs.
Pillay, T.S., "Gene of the month: the 2019-nCoV/SARS-CoV-2 novel coronavirus spike protein," J Clin Pathol, 2020, 73:366-369, 4 pgs.
Pinto, D., et al., "Cross-neutralization of SARS-CoV-2 by a human monoclonal SARS-CoV antibody," Nature, 2020, 583:290-295, 22 pgs.
Poh, C.M., et al., "Two linear epitopes on the SARS-CoV-2 spike protein that elicit neutralising antibodies in COVID-19 patients," Nat Commun, 2020, 11:2806, 7 pgs.
Price, J.V., et al., "'On silico' peptide microarrays for high-resolution mapping of antibody epitopes and diverse protein-protein interactions," Nat Med, 2012, 18(9):14341440, 16 pgs.
The R Core Team, "R: A Language and Environment for Statistical Computing, R Version 3.5.2" Vienna, Austria, R Foundation for Statistical Computing, 2018, https://www/R-project.org/, 3636 pgs.
Robbiani, D.F., et al., "Convergent Antibody Responses to SARS-CoV-2 in Convalescent Individuals," Nature, 2020, 584(7821):437-442, 35 pgs.
Routledge, E., et al., "Analysis of Murine Coronavirus Surface Glycoprotein Functions by Using Monoclonal Antibodies," J Virol, 1991, 65(1):254-262, 9 pgs.
Rowe, S.M., et al., "Clinical Mechanism of the Cystic Fibrosis Transmembrane Conductance Regulator Potentiator Ivacaftor in G551D-mediated Cystic Fibrosis," Am J Respir Crit Care Med, 2014, 190(2):175-184, 10 pgs.
Rubin, D.B., "Inference and Missing Data," Biometrika, 1976, 63(3):581-592, 12 pgs.
Schluchter, M.D., et al., "Jointly modelling the relationship between survival and pulmonary function in cystic fibrosis patients," Stat Med, 2002, 21:1271-1287, 17 pgs.
Shiryaev, S.A., et al., "New Details of HCV NS3/4A Proteinase Functionality Revealed by a High-Throughput Cleavage Assay," PLoS One, 2012, 7(4):e35759, 12 pgs.
Soares, H.D., et al., "Biomarkers Associated With the Apolipoprotein E Genotype and Alzheimer Disease," Arch Neurol, 2012, 69(10):1310-1317, 16 pgs.
Spivak, M., et al., "Improvements to the Percolator algorithm for peptide identification from shotgun proteomics data sets," J Proteome Res, 2009, 8(7):3737-3745, 22 pgs.
Srinagesh, H.K., et al., "The MAGIC algorithm probability is a validated response biomarker of treatment of acute graft-versus-host disease," Blood Advances, 2019, 3(23):4034-4042, 9 pgs.
Su, W., et al., "An empirical comparison of segmented and stochastic linear mixed effects models to estimate rapid disease progression in longitudinal biomarker studies," Stat Biopharm Res, 2021, 13(3):270-279, 22 pgs.
Tamburro, R.F., et al., "Pulmonary Complications of Pediatric Hematopoietic Cell Transplantation: A National Institutes of Health Workshop Summary," Ann Am Thorac Soc, 2021, 18(3):381-394, 14 pgs.
Tan, C.W., et al., "A SARS-CoV-2 surrogate virus neutralization test based on antibody-mediated blockage of ACE2-spike protein-protein interaction," Nat Biotech, 2020, 38:1073-1078, 17 pgs.
Tissot, A., et al., "Early Identification of Chronic Lung Allograft Dysfunction: The Need of Biomarkers," Frontiers in Immunology, 2019, 10:Article 1681, 13 pgs.
Uhl Ving, H.H., et al., "Bronchiolitis obliterans after allo-SCT: clinical criteria and treatment options," Bone Marrow Transplantation, 2012, 47:1020-1029, 10 pgs.
Van Der Ploeg, E.A., et al., "The potenial of biomarkers of fibrosis in chronic lung allograft dysfunction," Transplantation Reviews, 2021, 35(3):100626, 11 pgs.

(56) References Cited

OTHER PUBLICATIONS

Veraar, C., et al., "Potential novel biomarkers for chronic lung allograft dysfunction and azithromycin responsive allograft dysfunction," Scientific Reports, 2021, 11(1):6799, 13 pgs.

Verhaeghe, C., et al., "Intrinsic pro-angiogenic status of cystic fibrosis airway epithelial cells," BioChemical and Biophysical Research Communications, 2007, 356:745-749, 5 pgs.

Verleden, G.M., et al., "Azithromycin Reduces Airway Neutrophilia and Interleukin-8 in Patients with Brochiolitis Obliterans Syndrome," Am J Respir Crit Care Med, 2006, 174:556-570, 5 pgs.

Verleden, S.E., et al., "Chronic lung allograft dysfunction phenotypes and treatment," Journal of Thoracic Disease, 2017, 9(8):2650-2659, 11 pgs.

Volkova, N., et al., "Disease progression in patients with cystic fibrosis treated with ivacaftor: Data from national US and UK registries," J Cystic Fibros, 2020, 19:68-79, 12 pgs.

Walls, A.C., et al., "Tectonic conformational changes of a coronavirus spike glycoprotein promote membrane fusion," PNAS, 2017, 114(42):11157-11162, 6 pgs.

Waterhouse, A., et al., "SWISS-MODEL: homology modelling of protein structures and complexes," Nucleic Acids Res, 2018, 46:W296-W303, 8 pgs.

Wewer Albrechtsen, N.J., et al., "Plasma Proteome Profiling Reveals Dynamics of Inflammatory and Lipid Homeostasis Markers after Roux-En-Y Gastric Bypass Surgery," Cell Syst, 2018, 7:601-612.e1-e3, 16 pgs.

Whitman, J.D., et al., "Test performance evaluation of SARS-CoV-2 serological assays," Nat Biotechnol, 2020, 38(10):1174-1183, 26 pgs.

Wolff, D., et al., "Biomarkers in chronic graft-versus-host disease—quo vadis?" Bone Marrow Transplant, 2018, 53(7):832-837, 10 pgs.

Woolhouse, M.E.J., et al., "Epidemiological characteristics of human-infective RNA viruses," Sci Data, 2018, 5:180017, 6 pgs.

Xia, S., et al., "A pan-coronavirus fusion inhibitor targeting the HR1 domain of human coronavirus spike," Sci Adv, 2019, 5:eaav4580, 15 pgs.

Xu, G.J., et al., "Comprehensive serological profiling of human populations using a synthetic human virome," Science, 2015, 348(6239):aaa0698, 23 pgs.

Yu, J., et al., "Biomarker Panel for Chronic Graft-Versus-Host Disease," J Clin Oncol, 2016, 34(22): 2583-2590, 10 pgs.

Yuan, M., et al., "A highly conserved cryptic epitope in the receptor-binding domains of SARS-CoV-2 and SARS-CoV," Science, 2020, 368:630-633, 4 pgs.

Zhu, N., et al., "A Novel Coronavirus from Patients with Pneumonia in China, 2019," N Engl J Med, 2020, 382(8):727-733, 7 pgs.

Ziady, A.G., et al., "Redox balance in cystic fibrosis," Int J Biochem Cell Biol, 2014, 0:113-123, 27 pgs.

Zost, S.J., et al., "Potently neutralizing and protective human antibodies against SARS- CoV-2," Nature, 2020, 584(7821):443-449, 34 pgs.

European Search Report, Supplementary, and Written Opinion dated May 15, 2023, for Application No. EP 20798040.0, 9 pgs.

International Search Report and Written Opinion dated Dec. 30, 2021 for Application No. PCT/US2021/044587, 14 pgs.

International Search Report and Written Opinion dated Feb. 9, 2021 for Application No. PCT/US2020/054664, 12 pgs.

International Search Report and Written Opinion dated Mar. 28, 2022 for Application No. PCT/US2021/062624, 16 pgs.

International Search Report and Written Opinion dated Jun. 7, 2022 for Application No. PCT/US2022/012561, 21 pgs.

International Search Report and Written Opinion dated Sep. 25, 2023 for Application No. PCT/US2023/020341, 21 pgs.

International Search Report and Written Opinion dated Sep. 25, 2023 for Application No. PCT/US2023/020337, 22 pgs.

\* cited by examiner

COMPOSITIONS AND METHODS FOR TREATMENT OF LUNG FUNCTION

CROSS-REFERENCE TO RELATED APPLICATIONS

This application is a continuation-in-part of U.S. Ser. No. 16/922,119 filed Jul. 7, 2020, which claims priority to U.S. Ser. No. 15/927,575 filed Mar. 21, 2018, which claims priority to and benefit of U.S. Provisional Application No. 62/474,739, filed Mar. 22, 2017, the contents of each are incorporated in their entirety for all purposes.

GOVERNMENT SUPPORT CLAUSE

This invention was made with government support under HL142210, HL154105, HL116226 and HL125954 awarded by the National Institutes of Health. The government has certain rights in this invention.

BACKGROUND

Cystic fibrosis (CF) is an autosomal recessive disorder that affects approximately 30,000 individuals in the United States. The primary defect results from mutations of the cystic fibrosis transmembrane conductance regulator gene, which codes for the CFTR chloride channel. The protein is expressed predominantly on the apical surface of epithelial cells throughout the body (although low level expression has been detected in other tissues). Over 2,000 disease causing mutations have been identified in the CFTR gene, with the majority of patients (~90%) exhibiting at least one allele with the F508del mutation. Disease causing mutations fall into 5 classifications that result in abnormal CFTR protein that is either truncated, misprocessed/mislocalized, lacking channel gating function, or malformed due to improper gene splicing. With advances in new-born and other screenings, CF is usually diagnosed at birth. Although the determinants of disease are well characterized, forecasting disease progression has been extremely difficult and as of yet unsuccessful.

Care for CF patients has advanced rapidly over the past two decades, with an increase in patient longevity and quality of life that is unprecedented. The reasons for these improvements include a number of factors. First, the Cystic Fibrosis Foundation (CFF) has been tracking outcomes for nearly 50 years through their robust Patient Registry (CFF-PR), which includes patient data from nearly all CF patients in the US (individuals receiving care at accredited US CF centers), allowing assessment of outcomes and treatment responses. Next, there have been dramatic advances in new CF therapeutics (e.g. the development of recombinant human DNase, inhaled antibiotics including dissolved and dry powder tobramycin, aztreonam, hypertonic saline, low dose azithromycin to control inflammation, FDA approval of standardized pancreatic enzyme replacement, and most recently genotype-specific CFTR modulators such as KALYDECO® (4) and ORKAMBI® (5), and more recently TRIKAFTA® (6). In tandem with these new treatments, there has been a focus on the development of CF care guidelines and standardization of care across accredited CF care centers. This has helped to 'raise all boats' in the CF care community, accompanied by center-specific data to drive local quality improvement. Finally, understanding of disease severity predictors has advanced significantly, including the importance of weight in predicting pulmonary stability, the contribution of chronic Pseudomonas and MRSA infection to pulmonary decline and mortality, and the relationship between poorly controlled diabetes and disease progression. Indeed, these advancements have increased the median survival of CF patients to 41 years (CFF-PR—2014), and nearly 50% of CF patients alive today are adults. However, despite this impressive progress in CF care, lung function decline continues even in patients being treated with the best modulators of CFTR currently available. (See, e.g., Nataliya Volkova et al., Disease progression in patients with cystic fibrosis treated with ivacaftor: Data from national US and UK registries. JCF. DOI: 10.1016/j.jcf2019.05.015.)

Accompanying the improvements in CF outcomes are a number of challenges that urgently require attention. There have been dramatic global improvements in the CF disease trajectory, but many patients have not fully benefited from the advancements described above. (FIG. 3.) Indeed, the average age of death of CF patients in a given year has remained remarkably static, with most patients dying of CF lung disease during their third decade of life (CFF-PR 2014 statistics). The burden of care also remains a significant challenge, as most adolescents and young adults need to spend approximately two hours daily dedicated to therapies that maintain health. Adherence to complex care regimens is often untenable, and this has led to the need to 'personalize' care such that patients commit to daily therapies that are most likely to benefit them individually. These commitments increase during periods of instability, and treatment of PE remains highly interruptive to daily care and negatively impacts quality of life. They also are sentinel markers of disease progression, as 25% of CF patients fail to recover lung functions following PEs. The benefits of care improvements have also challenged the capacity to monitor CF lung disease and CF manifestations in other organs. Assessing the relative benefit of new therapies in the context of relatively normal lung function (as measured by routine spirometry) is particularly challenging for CF providers. This requires the development of more sensitive tools to identify subjects most likely to benefit from various interventions and to monitor the impact of new therapies added to care plans. Finally, the conduct of clinical trials to advance CF outcomes and interventions can no longer rely on standard outcome measures such as forced expiratory volume in 1 sec ($FEV_1$), as excessively large and/or long clinical trials are needed to demonstrate improvements in crude measurements such as lung function. Thus, the CF field stands at a crossroads, where the benefits of the past limit the capacity to advance therapies and personalize care when relying upon standard measures of disease status. The disclosed methods, in certain aspect, may be used to address these gaps, seeking to produce vertical advancement in disease monitoring and prediction through the use of advanced biostatistical modeling of lung function, which may be further enhanced via coupling with novel molecular biomarkers and/or imaging. The disclosed methods may be used to identify those patients most likely to benefit from various interventions, and allow clinicians to monitor responses to precise and personal interventions.

The natural history of the disease is well studied; but disease progression is not well understood. Pulmonary decline typically begins in adolescence, but current measures tend to follow rather than predict outcomes. For example, if a marker predicted disease instability and erratic swings in lung function, established or novel interventions to prevent decline could be implemented. Several clinical measures track disease progression, including $FEV_1$, body mass index (BMI) and pulmonary exacerbations (PE). Presently, intervention is driven by lagging indications of lung function decline, which is far less beneficial than intervening in at risk subpopulations before decline is manifest. Therefore, methods that can be used to predict CF disease progression are highly desirable, as they would preemptively identify those at risk of future disease progression, allowing caregivers to tailor treatments and select intervention to prevent pulmonary decline. Personalizing therapy is a critical need in CF, as broad application of all available therapies leads to a high daily treatment burden and poor adherence. These measures are lagging indicators of disease progression that result from molecular changes directly or indirectly related to CFTR dysfunction. Furthermore, current monitoring of lung function data is inadequate, and fails to utilize novel biostatistical tools to identify patients at risk for future decline. The disclosed methods address one or more of aforementioned needs in the art.

BRIEF SUMMARY

Disclosed herein are methods for treating an individual at risk for non-linear lung function decline. The methods, in certain aspects, include the steps of a) determining one or more covariates associated with lung function in said individual, said covariate being selected from one or more of a clinical measure, a biomarker or an imaging marker; b) calculating a risk probability score based on said determining of one or more covariate, said risk probability score being used to characterize an individual as having no predicted lung impairment, mild predicted lung impairment, moderate predicted lung impairment, or severe predicted lung impairment; and c) treating said individual characterized as having mild predicted lung impairment, moderate predicted lung impairment, or severe predicted lung impairment with one or more of increased frequency of disease monitoring, increased frequency of infection monitoring, an anti-inflammatory therapy, or combinations thereof.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION

Definitions

Figure 1:
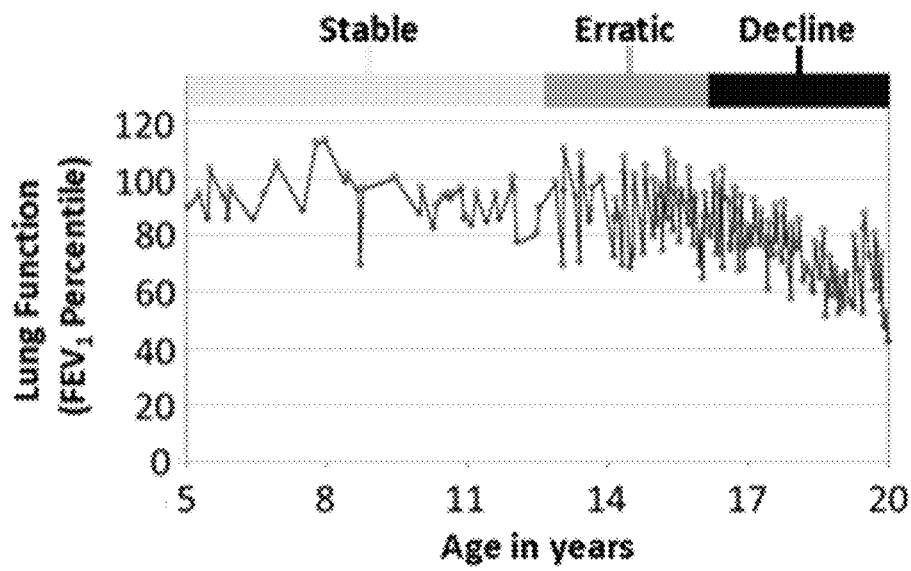
FIG. 1. Lung function in a typical CF patient. Lung function is separated into stages, with a stable period (light grey), an erratic period with large swings in $FEV_1$ (dark grey), and a decline stage (black).
Figure 2:
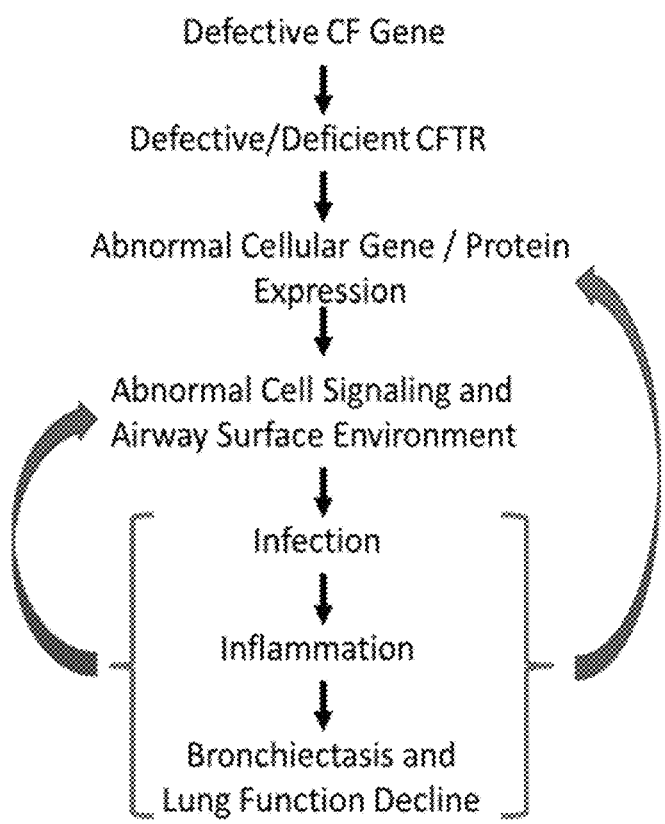
FIG. 2. Disease progression in CF. In depth serum proteomic analysis can capture molecular changes in serum that give rise to downstream organ pathology.

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "effective amount" means the amount of one or more active components that is sufficient to show a desired effect. This includes both therapeutic and prophylactic effects. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

The standard of care for patients with cystic fibrosis (CF) has advanced rapidly but CF patients still suffer routinely from pulmonary exacerbations (PE) and these are under reported. Current treatment methods are reactive to drops in lung function. A prognostic test that may be used to predict lung function decline in CF patients based on the combination of clinical data with molecular and imaging markers may be used to proactively treat CF patients. Variables such as historic lung function measures, biomarkers in blood, and regional lung structural and functional information obtained by imaging may be combined into a functional data algorithm that may be used to forecast the projection of lung function trajectory for a time period, for example, about 6 to about 12 months. Spirometric measures of lung function, namely the forced expiratory volume in one second ($FEV_1$), remain the most commonly used clinical measure of disease progression. It may be noted that $FEV_1$ percentile (standardized to CF) is not equivalent to $FEV_1$ percent predicted (standardized to general population). As used herein, reference to $FEV_1$ refer to $FEV_1$ percentile or $FEV_1$ percent predicted.

However, these measures provide only whole-lung metrics of lung function, making them insensitive to early disease. As a result of this inherent insensitivity and improved clinical care, the majority of pediatric CF patients now have normal $FEV_1$, making it increasingly difficult to detect early lung disease, when intervention would be most beneficial. As clinicians move toward maintaining higher lung function for longer periods of time, it will become increasingly important to develop more sensitive measures of CF lung disease and/or more specific biomarkers. Further, combining these non-invasive testing modalities to predict exacerbations and lung function decline may be advantageous. The limitations of $FEV_1$ and the pressing need for higher sensitivity for forecasting lung disease progression are relevant to a number of disorders, including COPD, severe asthma, and non-CF bronchiectasis. Here, methods employing an algorithm to predict structural remodeling in, and function of, the CF lung are disclosed. Such methods may be used with or without the use of one or more of the disclosed biomarkers, or sets of biomarkers disclosed herein.

In one aspect, Applicant has developed a dynamic prediction model to produce a novel diagnostic algorithm that identifies individuals at risk of lung function decline. In another aspect, Applicant has developed dynamic prediction modeling to identify CF patients who develop rapid pulmonary decline during adolescence. Disclosed herein are methods and assays which may be used in combination with an algorithm for prediction of CF lung disease progression that is superior to current practice. In one aspect, the disclosed methods may employ the use of novel biomarkers of disease severity that may enhance the ability of FD analysis to predict $FEV_1$ decline.

Figure 3:
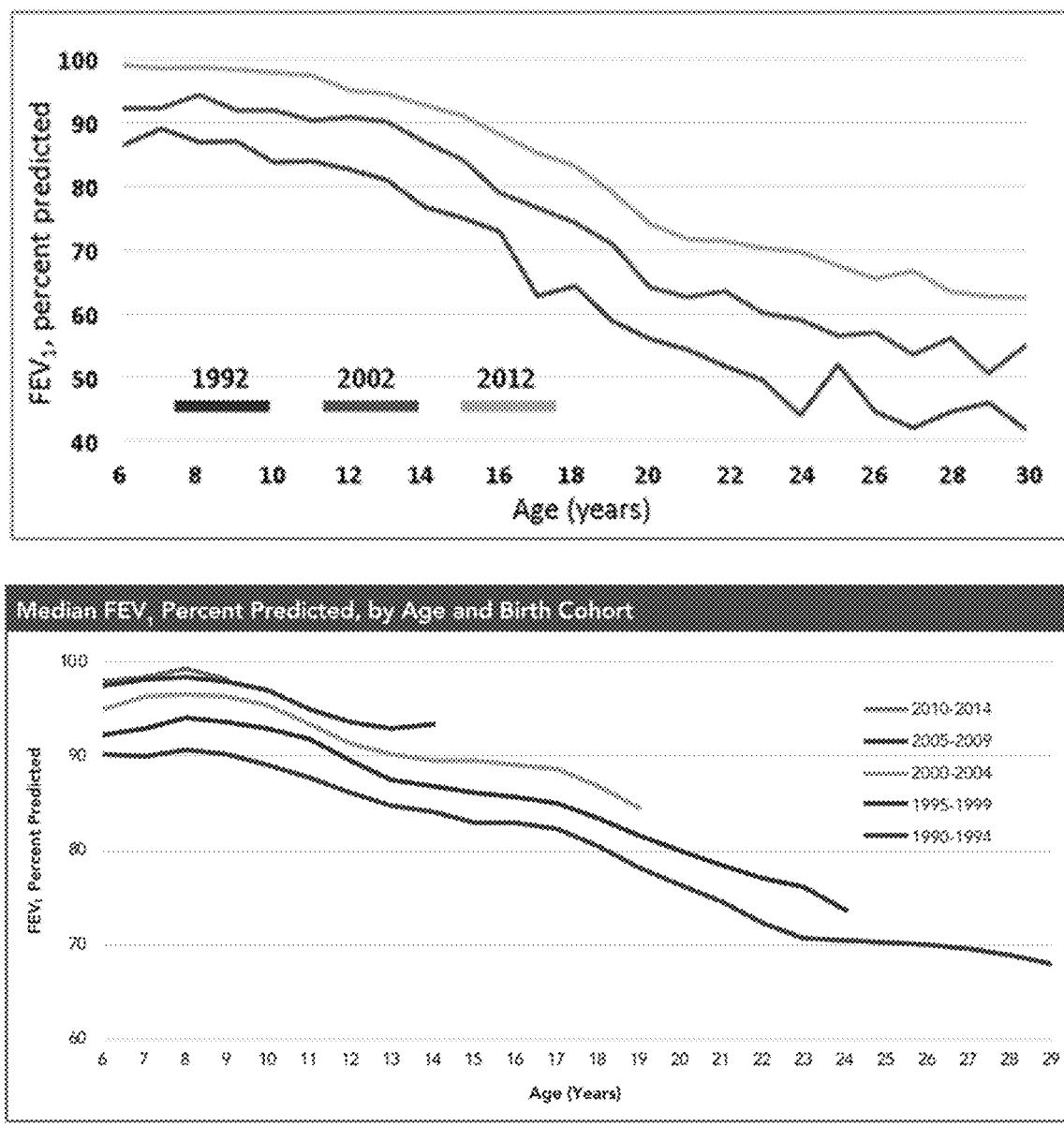
FIG. 3. Lung function decline with age. Comparison from data compiled from 1990-2014. Despite improvement in lunch function at early age, the rate of decline is unaffected by modern therapies. Source: CF Foundation Patient Registry data.

Three important measures are used in monitoring CF disease progression and response to therapy; $FEV_1$, PE frequency, and BMI. A rapid deterioration of lung function persists in CF patients, especially during adolescence. (FIG. 3). Although $FEV_1$, PE, and BMI are trailing indicators of disease progression, they are phenotypic culminations of molecular changes that persist and continue to influence the course of disease. In addition to the deleterious effects of CF disease progression (such as mucus plugging, bacterial infection, and inflammation), these clinical measures reflect a molecular basis of disease that may be detectable in biological specimens such as blood. Serum and/or plasma markers may be used to predict disease progression and may allow better estimation of future disease trajectory, which would inform therapy and facilitate development of patient-specific treatment regimens. Applicant has identified systemic changes reflected in the blood that culminate in measurable pulmonary decline as children enter adolescence, including serum and/or plasma markers that may be used to better estimate future disease trajectory, which may then be used to inform therapy and facilitate development of patient-specific treatment regimens.

In one aspect, described herein are novel methods for the prediction of lung function decline and treatment of individuals having or predicted to have lung function decline, such as individuals diagnosed with cystic fibrosis (CF).

In one aspect, a method of predicting lung function, more particularly, the likelihood of a decline in lung function, in an individual is disclosed. In certain aspects, the methods may include detecting expression of a one or more biomarkers selected from Table 1.

TABLE 1

Protein Isoform Name and Gene Name (Abbreviation)

| Protein isoform name | Gene name |
| --- | --- |
| Immunoglobulin alpha-1 heavy chain constant region | IGHA1 |
| kappa 1 immunoglobulin constant | IGKC |
| Immunoglobulin kappa light chain VLJ region | IGK |
| immunoglobulin lambda | IGL |
| Immunoglobulin lambda constant 2 | IGLC2 |
| Immunoglobulin lambda constant 3 | IGLC3 |
| Tight junction protein 3 | TJP3 |
| Alpha-1-acid glycoprotein 2 precursor | ORM2 |
| Signal-induced proliferation-associated 1-like protein 3 | SIPA1L3 |
| Plakophilin 4 | PKP4 |
| Inter-alpha (globulin) inhibitor H2 | ITIH2 |
| Absent in melanoma 1 protein | AIM1 |
| Actin filament-associated protein 1 isoform X2 | AFAP1 |
| Serine/threonine-protein phosphatase PP1-beta catalytic subunit | PPP1CB |
| Retinol-binding protein 4 | RBP4 |
| Fermitin family homolog 1 | FERMT1 |
| Actin, cytoplasmic 2 | ACTG1 |
| Transthyretin | TTR |
| Melanoma inhibitory activity protein 3 isoform X2 | MIA3 |
| Pleckstrin homology domain-containing family G member 1 isoform X3 | PLEKHG1 |

TABLE 1-continued

Protein Isoform Name and Gene Name (Abbreviation)

| Protein isoform name | Gene name |
|---|---|
| Pleckstrin homology domain-containing family A member 5 isoforms X1-X9 | PLEKHA5 |
| Pleckstrin | PLEK |
| Zinc finger protein 295 | Zbtb21 |
| Protocadherin Fat 2 | FAT2 |
| Cadherin-related family member 2 isoform X1 | CDHR2 |
| Voltage gated calcium channel alpha 1F subunit | CACNA1F |
| Actin filament associated protein | AFAP |
| Heat shock 70 kDa protein 1-like | HSPA1L |
| EF-hand calcium binding protein 2 | EFCBP2 |
| Polyamine modulated factor-1 (PMF1) protein | PMF1 |
| Keratin 16 | KRT16A |
| Keratin 18 | KRT18 |
| DNA replication ATP-dependent helicase/nuclease DNA2 isoform X4 | DNA2 |
| Non-lens beta gamma-crystallin like protein | CRYBG1 |
| Bromodomain and WD repeat-containing protein 1 isoform X1 | BRWD1 |
| Collagen type V alpha 3 chain | COL5A3 |
| Collagen type IV alpha | COL4A |
| Dynein heavy chain 12, axonemal isoform X5 | DNAH12 |
| Serine/arginine repetitive matrix protein 1 | SRRM1 |
| Ras-related protein Rap-1A | RAP1A |
| AT-hook-containing transcription factor isoform 1 | AKNA1 |
| Coiled-coil domain-containing protein 18 isoforms X1-X7 | CCDC18 |
| Coiled-coil domain-containing protein 180 | CCDC180 |
| Patatin-like phospholipase domain-containing protein 2 isoform X1 | PNPLA2 |

In one aspect, predicting lung function in an individual diagnosed with cystic fibrosis is disclosed. In certain aspects, the methods may include detecting expression of a one or more biomarkers selected from Table 2.

TABLE 2

Panel of protein biomarker covariates for algorithm that improve algorithm performance in $FEV_1$ predictions over a period from 3 weeks to 4 months after biomarker collection.

Protein name (gene name)

1. Alstrom syndrome protein 1 isoform 1
2. aminopeptidase O isoform X9 (C9orf3)
3. ankyrin-3 isoform 3
4. ARAP2 protein (ARAP2)
5. Bifunctional glutamate/proline—tRNA ligase (EPRS)
6. C10ORF6
7. CECR2 protein (CECR2)
8. cingulin-like 1 (CGNL1)
9. coiled-coil domain-containing protein 93 isoform X3 (CCDC93)
10. complement component C2 (C2)
11. complement component C6 isoform X7 (C6)
12. complement factor H (CFH)
13. connector enhancer of kinase suppressor of ras 2 isoform X2 (CNKSR2)
14. CTP:phosphocholine cytidylyltransferase
15. DNA annealing helicase and endonuclease ZRANB3 (ZRANB3)
16. EPRSN1
17. fibrinogen alpha chain preproprotein, isoform alpha (FGA)
18. filamin 2 (FLN2)
19. Fras1-related extracellular matrix protein 2 (FREM2)
20. FYVE, RhoGEF and PH domain-containing protein 5 isoform X2 (FGD5)
21. gelsolin isoform X3 (GSN)
22. glutamate receptor-interacting protein 1 isoform X7 (GRIP1)
23. hCG1656772
24. histidine-rich glycoprotein isoform X1 (HRG)
25. interferon regulatory factor-2 binding protein 2B
26. junction-mediating and -regulatory protein isoform X2 (JMY)
27. KIAA0328 protein KIAA0328
28. la-related protein 1 isoform X5 LARP1
29. MAX gene-associated protein isoform X11 (MGA)
30. paraoxanase-3
31. Platelet glycoprotein Ib alpha chain (GP1BA)
32. PMFBP1 protein (PMFBP1)
33. PRO2841
34. protein arginine N-methyltransferase 3 isoform X1 (PRMT3)
35. Protein SCAF11 (SCAF11)
36. ral GTPase-activating protein subunit alpha-1 isoform X12 (RALGAPA1)
37. Receptor-type tyrosine-protein phosphatase C (PTPRC)

TABLE 2-continued

Panel of protein biomarker covariates for algorithm that improve algorithm performance in $FEV_1$ predictions over a period from 3 weeks to 4 months after biomarker collection.
Protein name (gene name)

38. RGS3 isoform C2PA-RGS3 (RGS3)
39. Rho-GTPase activating protein 10 (ARHGAP10)
40. RNA-binding motif protein, Y chromosome, family 1 member B isoform X1 (RBMY1B)
41. protein-methionine sulfoxide oxidase MICAL3 isoform X10 (MICAL3)
42. Protein sidekick-2 (SDK2)
43. sacsin isoform X3 (SACS)
44. SAPS domain family, member 2 (SAPS2)
45. serum aryldialkylphosphatase precursor
46. spermatogenesis-associated protein 31C1 isoform X1 (SPATA31C1)
47. synaptotagmin-like protein 2 isoform X10 (SYTL2)
48. translation initiation factor (IF2)
49. triadin isoform X17 (TRDN)
50. uridine-cytidine kinase-like 1 isoform X7 (UCKL1)
51. utrophin isoform X4 (UTRN)
52. WD repeat-containing protein 64 isoform X2 (WDR64)
53. zinc finger and AT hook domain containing (ZFAT)

In one aspect, predicting lung function in an individual diagnosed with cystic fibrosis is disclosed. In certain aspects, the methods may include detecting expression of a one or more biomarkers selected from Table 3.

TABLE 3

Panel of protein biomarker covariates for algorithm that improve algorithm performance in $FEV_1$ predictions over a period 4 months or more after biomarker collection.
Protein name (gene name)

1. alpha 1 type XXIV collagen precursor
2. alpha-fetoprotein enhancer binding protein
3. cell division cycle 2-like 5 (cholinesterase-related cell division controller) (CDC2L5)
4. chromodomain-helicase-DNA-binding protein 6 isoform X3 (CHD6)
5. chromosome 3 open reading frame 15 (C3orf15)
6. cilia- and flagella-associated protein 91 isoform 3
7. CLIP-associating protein 2 isoform X24 (CLASP2)
8. coiled-coil domain-containing protein 18 isoform X2 (CCDC18)
9. collagen triple helix repeat-containing RP11-45B20.2
10. collagen, type XXIV, alpha 1 (COL24A1)
11. death inducer-obliterator-3 (DIDO3)
12. diacylglycerol kinase iota isoform X4 (DGKI)
13. DNA methyltransferase 1-associated protein 1
14. DNAH10 variant protein
15. E3 ubiquitin-protein ligase MIB2 isoform X5 (MIB2)
16. growth-inhibiting protein 24 (GIG24)
17. hemicentin
18. histone acetyltransferase MORF alpha
19. IF2 protein (IF2)
20. immunoglobulin lambda light chain VLJ region (IGL)
21. kinesin-like protein (KIF2)
22. kinesin-like protein KIF21A isoform X7 (KIF21A)
23. laminin subunit alpha-2 isoform X3 (LAMA2)
24. LIM and calponin homology domains-containing protein 1 isoform X20 (LIMCH1)
25. LIM and calponin homology domains-containing protein 1 isoform X22 (LIMCH1)
26. lysine-specific demethylase 2B isoform X7 (KDM2B)
27. multiple endocrine neoplasia type 1 candidate protein number 18 (HSPF2)
28. MYCBP-associated protein isoform X1 (MYCBPAP)
29. nebulin-related anchoring protein, isoform CRA_b
30. Non-canonical poly(A) RNA polymerase PAPD5 (PAPD5)
31. PAP associated domain containing protein 5 variant
32. partitioning-defective 3-like protein splice variant c (PAR3L)
33. PF6
34. Pleckstrin homology-like domain family B member 2 (PHLDB2)
35. poly (ADP-ribose) glycohydrolase (PARG)
36. probable E3 ubiquitin-protein ligase HERC1 isoform X1 (HERC1)
37. probable E3 ubiquitin-protein ligase HERC1 isoform X11 (HERC1)
38. Protein AMBP (AMBP)
39. RUNDC1 protein (RUNDC1)
40. serine/threonine-protein phosphatase 4 regulatory subunit 3A isoform 1
41. serine-protein kinase ATM isoform X5 (ATM)
42. SHMT2 protein (SHMT2)
43. smoothelin-B3 (SMTN)
44. somatostatin receptor interacting protein splice variant a (SSTRIP)
45. sperm-associated antigen 17 isoform X3 (SPAG17)

TABLE 3-continued

Panel of protein biomarker covariates for algorithm that improve
algorithm performance in $FEV_1$ predictions over a period 4 months or more after
biomarker collection.
Protein name (gene name)

46. T-cell lymphoma invasion and metastasis 1 (TIAM1)
47. terminal nucleotidyltransferase 4B isoform b
48. tetratricopeptide repeat protein 21A isoform X6 (TTC21A)
49. thrombospondin 1 (THBS1)
50. ubiquitin carboxyl-terminal hydrolase 40 isoform X1 (USP40)
51. Voltage-dependent N-type calcium channel subunit alpha-1B (CACNA1B)
52. Zinc finger homeobox protein 4 (ZFHX4)

In one aspect, the method may comprise the step of determining an expression level of one or more, or two or more, or three or more, or four or more, or five or more, or six or more, or seven or more, or 8 or more, or 9 or more, or 10 or more, or 11 or more, or 12 or more, or 13 or more, or 14 or more, or 15 or more or 16 or more, or 17 or more, or 18 or more, or 19 or more, or 20 or more, or 21, or more, or 22 or more, or 23 or more, or 24 or more, or 25 or more, or 26 or more, or 27 or more, or 28 or more, or 29 or more, or 30 or more, or 31 or more, or 32 or more, or 33 or more, or 34 or more, or 35 or more, or 36 or more, or 37 or more, or 38 or more, or 39 or more, or 40 or more, or 41 or more, or 42 or more, or 43 or more, or 44 or more, or 45 or more, or 46 or more, or 47 or more, or 48 or more, or 49 or more, or 50 or more, or each protein (or corresponding expression of each protein) in the protein set, wherein said method is predictive of one or more clinical parameters in said individual. It is intended that detection of a protein or protein expression level may be carried out using any method known in the art or hereafter developed which allows a determination or estimation of the relative expression or amount of a given protein.

In one aspect, the method may comprise the step of comparing said expression level to a control value to obtain a combined score and/or a risk probability score. A principle component or similar analysis that combines all the data from more than one or all of the markers may be used as well to generate a score. The combined score may be used to assess strength of association between the expression level of one or more of the aforementioned proteins, and the clinical parameter of interest. In one aspect, the clinical parameter may be lung function decline. The risk probability score may be used to predict the degree of risk that an individual will have or develop lung function changes or other clinical events that are of interest during the progression of cystic fibrosis.

In one aspect, the one or more clinical parameters may be selected from $FEV_1$, BMI, PE, number of hospitalizations, antibiotic status, infection status, and/or other clinical feature of the disease. These parameters may be selected using statistical methods described herein.

In one aspect, the clinical parameter is lung function decline, wherein an individual classified as being high risk for rapid lung function decline is treated via more aggressive anti-inflammatory therapy and increased monitoring. It is well known that increased disease monitoring is associated with improved pulmonary status. Thus, those identified to be at risk for rapid decline would warrant more frequent clinical encounters to ensure that stability is maintained. In addition, those at risk of decline may have become colonized with new pathogenic bacteria. Identification of subjects at risk of pulmonary decline would trigger aggressive testing for new pathogens and treatment to stem pulmonary decline, for example, by administration of anti-bacterial agents that address the specific pathogenic bacteria in an individual.

In one aspect, the sample may be blood, serum, urine, plasma, PBMCs, BALF, nasal and/or lower airway brushings, sputum, GI biopsies, lung explants, and combinations thereof. The sample may be obtained using routine methods known in the art. Multiple samples may be obtained over a period of time, for example, once every day, once every other day, once a week, once every two weeks, once every three weeks, once monthly, or once every two months, or once every three months, etc.

In one aspect, the detection step is carried out using mass spectrometry. For example, electrospray/matrix-assisted laser desorption ionization mass spectrometry may be used, as described herein.

In one aspect, the methods described herein may be carried out via the use of a computerized device. For example, one or more of the combined score or risk probability score may be calculated using a computer.

In one aspect, the combined score and risk probability score may be used to create a predictive model within a web browser, the computer having a graphical user interface (GUI) in which an end user can interactively explore the predictive model within a web browser. In one aspect, the end user may be, for example, a physician, patient, or patient guardian. The end user may use the interface to interactively explore the predictive model within a web browser. In one aspect, the GUI may be called the Cystic Fibrosis Point of Personalized Detection (CFPOPD). Predictions may be generated on an individual basis, utilizing data from CF cohorts, such as the Cystic Fibrosis Foundation Patient Registry, and the user may select which patient for which the prediction model is graphically illustrated. Inputs include, but are not limited to, clinical and demographic characteristics, such as those from electronic health records, and large-scale data from proteomics.

Figure 13:
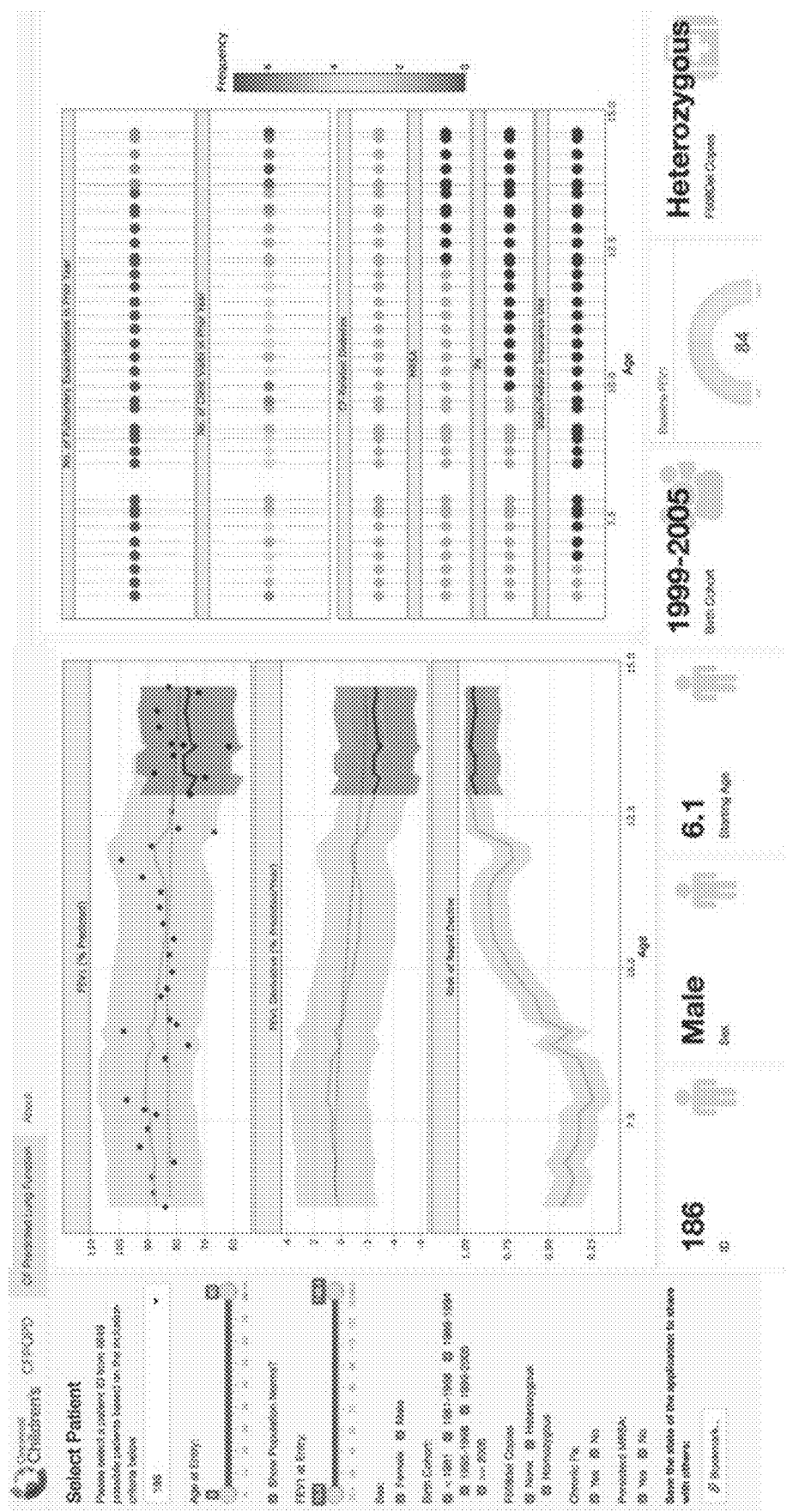
FIG. 13. GUI Prototype. The GUI (graphical user interface) was composed using the R statistical programming language, specifically using the flexdashboard, shiny, and plotly packages. See R Core Team (2017). R: A language and environment for statistical computing. R Foundation for Statistical Computing, Vienna, Austria. URL https://www.R-project.org; Barbara Borges and J J Allaire (2017). flexdashboard: R Markdown Format for Flexible Dashboards. R package version 0.5.1. https://CRAN.R-project.org/package=flexdashboard; Winston Chang, Joe Cheng, J J Allaire, Yihui Xie and Jonathan McPherson (2017). shiny: Web Application Framework for R. R package version 1.0.5. https://CRAN.R-project.org/package=shiny; Carson Sievert, Chris Parmer, Toby Hocking, Scott Chamberlain, Karthik Ram, Marianne Corvellec and Pedro Despouy (2017). plotly: Create Interactive Web Graphics via 'plotly.js'. R package version 4.7.1. https://CRAN.R-project.org/package=plotly.

Measured and predicted lung function may be portrayed using three interactive graphs linked by a common timeline. $FEV_1$, the $FEV_1$ derivative, and the risk of rapid decline may all be displayed with corresponding shaded confidence bands. Additionally, the GUI may include patient-level and ecological descriptive variables as well as proteomic data that can be used to subset the pool of individual patients to select from, and the GUI may be expanded to include additional inputs. This may be used to facilitate, for example, the comparison of individually forecasted rapid lung function decline among individuals that are identical with respect to all model covariates expect for their sex. Both static and temporal covariates are displayed using graphical and text-based panels. An exemplary GUI prototype is currently available for public use at http://cfpopd.amazon-shiny.duckdns.org/and a screenshot is contained in FIG. 13.

In certain aspects, the methods may be used in conjunction with evaluation of a drug or treatment for cystic fibrosis. For example, a potential treatment may be administered to an individual in need thereof, and the disclosed methods may be carried out following administration of such drug or treatment.

In one aspect, a method for predicting evolution of a clinical parameter in an individual diagnosed with cystic fibrosis is disclosed. In this aspect, the method may comprise the steps of calculating a risk probability score from expression levels of a biomarker set comprising one or more biomarkers of Table 1; and classifying said individual into a high risk or low risk group based on the risk probability score; forecasting lung function trajectory based on said risk probability score. In certain aspects, the step may be performed on a computer. In one aspect, the clinical parameter may be lung function decline. In one aspect, the combined score may be based on at least two clinical measurements, or at least three clinical measurements, or at least four clinical measurements. The biomarker expression may be detected using methods known in the art, or using methods as set forth herein.

In one aspect, a method for segregating severe and disease in an individual diagnosed with cystic fibrosis is disclosed. The method may comprise the steps of detecting and quantifying a biomarker set comprising one or more proteins of Table 1, wherein said detecting step is carried out by assaying a biological sample from said individual and a clinical parameter obtained from said individual; and classifying the individual into a high or low risk group based on the combined score. The steps may be performed on a computer. In one aspect, the clinical parameter may be forced expiratory volume ($FEV_1$), and the method may be used to predict the risk of a rapid decline in $FEV_1$ in a said individual.

Calculation of Combined Score and Risk Probability Scores

A marginal score may be used to classify an individual as a high risk or low risk individual for rapid lung function decline and the combined score may be used to perform feature selection wherein proteins are selected that correspond to said individual's risk of rapid lung function decline.

Marginal Score (Risk of Rapid Decline as High or Low). In the first stage, $Y_{ij}$ may be a random variable representing lung function for patient i at time $t_{ij}$; i=1 ... N; j=1 ... $n_i$. For illustration, time refers to age (in years), but may be defined using other measures, including but not limited to: time since first pulmonary function measurement, in years; time since first serum collection, in years. In applying the calculation, it may be assumed $Y_{ij}$ is observed over one or more occasions, creating a random vector for each patient, represented as $Y_i$. In observation, these data may be sparsely or irregularly collected for various reasons, at the discretion of the user. Using Equation 1 (from Yao, Muller and Wang (2005)), the collection of lung function trajectories across patients observed at different time points can be expressed as follows. In one aspect, $X_i(T_{ij})$ may be the longitudinal process of $FEV_1$ for patient i at random time $T_{ij}$, which is measured with error $\varepsilon_{ij}$. This corresponds to the decomposition of longitudinal $FEV_1$ of Equation (1):

$$Y_{ij} = X_i(T_{ij}) + \epsilon_{ij} = \mu(T_{ij}) + \sum_{k=1}^{\infty} \xi_{ik}\phi_k(T_{ij}) + \epsilon_{ij}$$

where $\varepsilon_{ij}$ is residual error with mean zero and some variance $\sigma^2$; $X_i(\cdot)$, which is the function depicting the smooth, continuous longitudinal $FEV_1$ profile for patient i, can be characterized, for example, using a cubic b-spline basis with knot locations as described by Szczesniak and others (2013). Applying the PACE approach (principal components analysis through conditional expectation) as described by Yao, Muller and Wang (2005) to the longitudinal $FEV_1$ data outlined herein can be decomposed into functional principal component scores $\xi_{i1}, \ldots, \xi_{iK}$, where each score is a univariate quantity representing the $k^{th}$ harmonic depicting the $i^{th}$ patient's continuous longitudinal $FEV_1$ profile. These quantities correspond to said marginal scores and have been calculated previously for $FEV_1$ data from the Cystic Fibrosis Foundation Patient Registry, and the resulting scores can be used to classify said individual as high risk or low risk for rapid decline (Szczesniak et al. 2017). Techniques for choosing the number of harmonics, K, include, but are not limited to: cross validation.

Combined Score (Feature Selection According to Expression Level of Protein and Risk of Rapid Decline). In one aspect, the $1^{st}$ protein of the $k^{th}$ patient may be represented as $P_{li}$, and $P_l$ may be the vector combining measurements of this protein across all patients. Similarly, the functional principal component scores (said marginal scores) for the $k^{th}$ component across all patients may be the vector $\xi_k$. $\rho_{k\cdot\rho kl}$ may be the correlation coefficient representing the bivariate association between $\xi_k$ and $P_k$. Methods to estimate $\rho_{kl}$ include, but are not limited to, Spearman's rank correlation coefficient and Pearson's correlation coefficient, such application being readily understood by one of ordinary skill in the art. Said coefficient $\rho_{kl}$, with estimated value denoted as $\hat{\rho}_{kl}$, represents said combined score from this two-stage process for a given protein with the $FEV_1$ trajectory. Implementation of the approach can proceed using R (R Foundation for Statistical Computing, Vienna, Austria).

In one aspect, a risk probability score may be obtained using the following Equation (2):

$$Y_{ij} = X_i(T_{ij}, Z_{ij}) + \epsilon_{ij} = \mu(T_{ij}, Z_{ij}) + \sum_{k=1}^{\infty} \xi_{ik}\phi_k(T_{ij}, Z_{ij}) + \epsilon_{ij},$$

Obtaining said combined score may further include inputting data for one or more clinical parameters of the individual. The marginal and combined scores, further including the step of inputting data on one or more clinical parameters, can be derived from a two-stage process. Stage I. Let variables be defined as in Stage 1. Additionally, let input data from one or more clinical parameters, such as observed body mass index percentile, be represented as Zij. The input will take the form of a vector if inputting data from one clinical parameter, and will take the form of a matrix with dimension N×C if there are c=1, ... , C clinical parameters. One or more covariates may be time-varying. Using technique and assumptions for mean-adjusted functional principal components analysis described by Jang and Wang, Equation (1) is expanded as Equation (2) above, where estimation can proceed as they describe based on Equation (2) above with stated changes to covariance accommodating Zit. Let ξikc be the functional principal component scores, where c denotes that these scores are covariate adjusted. Stage II. As described in Stage II, ρkcl is estimated for bivariate association of resulting covariate-adjusted functional principal component scores, in which bivariate association is estimated between vectors ξkc and Pl. Resulting estimate $\hat{\rho}_{kcl}$ represents combined score for a given protein with the $FEV_1$ trajectory, which further includes inputting data on one or more clinical parameters.

Obtaining a risk probability score may further include the step of inputting data for one or more clinical parameters of an individual.

Modifying notation from Stage I, $Y_i$ may be realizations of a longitudinal patient-specific process other than $FEV_1$, such as body mass index percentile. By Equation (1) and aforementioned approaches, this substitution yields principal component scores $\xi_{i1o}, \ldots, \xi_{iKo}$, where o indicates the given outcome process being analyzed as $Y_i$. Stage II. Modifying notation from Stage II, $\rho_{klo}$ may be the correlation coefficient representing the bivariate association between $\xi_{ko}$ and $P_k$. Using the method described in Stage II, coefficient $\rho_{klo}$, with estimated value denoted as $\hat{\rho}_{klo}$, represents said combined score from this two-stage process for a given protein with the outcome process noted as o.

Additional clinical parameters as inputs. If using additional clinical inputs as described above and letting $Y_i(t)$ be realizations of a longitudinal patient-specific process over time t other than $FEV_1$, such as body mass index percentile, yields covariate-adjusted combined scores for a different clinical endpoint. Resulting estimate $\hat{\rho}_{klco}$ represents combined score for a given protein with the outcome process noted as o, which further includes inputting data on one or more clinical parameters as covariates.

Derivation of Risk Probability Score. Let $Y_{ij}$ represent $FEV_1$ for a given patient and time point. Assume that the longitudinal $FEV_1$ process follows the Gaussian linear mixed model with non-stationary covariance as defined by Diggle, Sousa and Asar (2015). The prediction algorithm to obtain a risk probability score can be defined through the following sequence of equations:

$$Y_{ij}=f_i(t_{ij})+U_i+W_i(t_{ij})+\epsilon_{ij}=g(t_{ij})+P_{ij}^T\beta+U_i+W_i(t_{ij})+\epsilon_{ij}, \quad \text{Equation (3):}$$

where $f_i(t_{ij})$ is the mean response function for the patient's longitudinal lung function process; $U_i$ is a patient-specific random intercept term, allowing patient profiles to deviate randomly from one another; $W_i(t_{ij})$ is a stochastic process characterizing the change in an individual's lung function process that cannot be explained by $f_i(t_{ij})$ alone; $\epsilon_{ij}$ is residual error from the model. In the second part of the equation, $g(t_{ij})$ is a nonparametric function representing a smooth, continuous-time process for lung function, which may be estimated using cubic b-splines; $P_{ij}$ is the covariate information on a single protein or set of proteins, corresponding to a vector or matrix, where T implies taking the transpose; $\beta$ is the vector of parameter coefficients corresponding to associations between lung function and protein expression level(s). Assuming $W_i(t_{ij})$ follows integrated Brownian motion, it follows that the derivative of this quantity in Equation (3) will yield Brownian motion, denoted $B_i(t_{ij})$ for the $i^{th}$ subject and $j^{th}$ time point. Then, the risk probability score is defined as Equation (4):

$$P_r(B_i(t_{ij}))=P_r(B_i(t_{ij})<\delta_i-f'_i|\mathcal{H}_i(t))$$

where $\delta_i$ is certain threshold for the rate of decline, which may be patient specific (hence i subscript) or uniform for all patients; $f'_i(t)$ is the first derivative of the process from the model structure in Equation (3) and $H_i(t)$ is all protein expression covariate history before a given time on the $i^{th}$ patient. Protein expression levels may either be observed cross-sectionally or longitudinally.

Quantifying Uncertainty of Risk Probability Score. Pointwise confidence intervals for the patient-specific risk probability score defined in Equation (5) can be derived as follows. Without loss of generality, assume this derivation is for a 95% pointwise confidence interval. Let $\mu_{B_{ii}}$ and $\Sigma_{n_i}$ denote the mean and variance for $B_i(t_{ij})$ given $H_i(t)$. We assume the mean $\mu_{B_{ii}}$ satisfies:

$$\sqrt{n_i}(\hat{\mu}_B - \mu B_i) \xrightarrow{D} N_{n_i}(0, \Sigma_{n_i}) \quad \text{Equation (5):}$$

where $\mu_{B_i}$ denotes the vector $\mu_{B_{i1}}, \ldots, \mu_{Bin_i}$, $\hat{\mu}_{B_i}$ is the estimate of $\mu_{B_i}$, and $n_i$ is the sample size for $i^{th}$ patient.

For each patient i, let $\hat{\Sigma}_{n_i}$ in denote the estimation of $\Sigma_{n_i}$ from estimating parameters in the model from Equation (3) and taking derivatives of the relevant probability risk score quantities in Equation (4). The bootstrapping process to obtain a 95% confidence interval for risk probability is below.

(1) Sample B—independent samples, $Y_{n_i1}, \ldots, Y_{n_iB}$ from $N_{n_i}(0, \hat{\Sigma}_{n_i}), B=1, \ldots, 100$, and define parameter $\mu^*_{B_i}=\hat{\mu}_{B_i}+n^{-1/2}Y_{n_i b}$ (2) For each sample $Y_{n_i b}$, calculate $Pr^*(B_i(t_{ij}))$ using $\mu^*_{B_i}$ by Step (1) above and calculate mean square error (MSE) for $$Pr^*(B_i(t_{ij})) \text{ as } \widehat{MSE^*_{n_i}} = B^{-1}\sum_{b=1}^{B}[Pr^*(B_i(t_{ij})) - Pr(\widehat{B_i(t_{ij})})]^2.$$

(3) Construct the 95% confidence interval for risk probability by $P_r(\widehat{B_i(t_{ij})})\pm z_{0.975}\sqrt{\widehat{MSE^*_{n_i}}}$.

In one aspect, the risk probability score may be calculated using an algorithm which further includes the step of inputting data from one or more clinical parameters of an individual.

Derivation of Risk Probability Score. Additionally define $Z_{it}$, wherein additional inputting data on clinical parameters, such as observed body mass index percentile, are represented as $Z_{ij}$. The input will take the form of a vector if inputting data from one clinical parameter, and will take the form of a matrix with dimension N×C if there are $c=1, \ldots, C$ clinical parameters, and $Z_{ij}$ may include covariates that are time-varying. To accommodate the additional inputs, Equation (3) can be expanded as:

$$Y_{ij}=f_i(t_{ij})+U_i+W_i(t_{ij})+\epsilon_{ij}=g(t_{ij})+P_{ij}^T\beta_P+Z_{ij}^T\beta_Z+U_i+W_i(t_{ij})+\epsilon_{ij} \quad \text{Equation (6):}$$

where $\beta_Z$ is the parameter vector representing associations between each clinical input variable and the longitudinal lung function process.

It follows that the risk probability score can be modified to include covariate history by expanding Equation (4) as follows:

$$P_r(B_i(t_{ij}))=P_r(B_i(t_{ij})<\delta_i-f'_i(t)|\mathcal{H}_{iP}(t), \mathcal{H}_{iZ}(t)) \quad \text{Equation (7):}$$

wherein covariate history from the clinical, protein expression, and previous outcome inputs are represented as $H_{iP}(t)$ and $H_{iZ}(t)$, respectively. Although it is suppressed in Equation (7), the expression includes previous outcome history prior to the time point $t_{ij}$.

Quantifying Uncertainty of Risk Probability Score. Bootstrapped estimates for covariate-adjusted risk probability scores can be computed as in Equation (5). In one aspect, the risk probability score may be performed for another clinical outcome.

Modifying notation from above, let $Y_{ij}$ be realizations of a longitudinal patient-specific process other than $FEV_1$, such as body mass index percentile. By Equations (3) and (4) and approaches therein, the patient-specific risk probability score can be expressed as:

$$P_r(B_{io}(t_{ij}))=P_r(B_{io}(t_{ij})<\delta_{io}-f'_{io}(t))|\mathcal{H}_{io}(t)\qquad \text{Equation (8):}$$

where elements correspond to the terms defined in Equation (4) but for a different outcome o than $FEV_1$. Boot-strapped estimates for risk probability scores based on outcome o can be computed as in Equation (6).

Equation (8) and approaches herein can be adapted using the procedure set forth above to acquire covariate-adjusted estimates of risk probability for clinical outcome o.

In one aspect, disclosed herein is a method for treating an individual at risk for non-linear lung function decline. The method may comprise a) determining one or more covariates associated with lung function in said individual, said covariate being selected from one or more of a clinical measure, a biomarker or an imaging marker; b) calculating a risk probability score based on said determining of one or more covariate, said risk probability score being used to characterize an individual as having no predicted lung impairment, mild predicted lung impairment, moderate predicted lung impairment, or severe predicted lung impairment; and c) treating said individual characterized as having mild predicted lung impairment, moderate predicted lung impairment, or severe predicted lung impairment with one or more of increased frequency of disease monitoring, increased frequency of infection monitoring, anti-inflammatory therapy, or combinations thereof.

In one aspect, the risk probability score may comprise a risk probability of a clinical outcome selected from a decrease in forced expiratory volume in one second ($FEV_1$), pulmonary exacerbation (PE) frequency, FEV1-indicated exacerbation signal (FIES), ventilation defect percent (VDP), abnormal lung heterogeneity in lung as measured via imaging, lung hyperinflation, and combinations thereof.

In one aspect, the covariate may be a clinical measure selected from forced expiratory volume in one second ($FEV_1$), body mass index percentile (BMI), pulmonary exacerbation (PE) frequency, historic lung function, ventilation defect percent (VDP), partial ventilation data, ventilation heterogeneity data, hyper-intensity data, FEV1-indicated exacerbation signal (FIES), and combinations thereof.

In one aspect, the covariate may be a biomarker described in Table 1, Table 2, Table 3, or Table 4, said determining comprising determining an expression level of a protein described in Table 1, Table 2, Table 3, or Table 4.

In one aspect, the covariate may be an imaging marker, said imaging marker including but not limited to VDP, lung heterogeneity, lung hyperinflation, CT, or the like.

In one aspect, the imaging marker may be a functional lung measurement, a structural lung measurement, or combinations thereof.

In one aspect, the imaging marker may be obtained by an imaging method.

In one aspect, the image technique may be selected from hyperpolarized (HP) 129Xe, Ultra-short Echo-time (UTE) Magnetic resonance imaging (MRI), computed tomography (CT), and combinations thereof.

In one aspect, the imaging marker may be structural remodeling of the lung.

In one aspect, the imaging marker may be bronchiectasis.

In one aspect, the predicted lung impairment may be non-linear decline in one or more parameters selected from Ventilation Defect Percentage (VDP), $FEV_1$, partial ventilation, ventilation heterogeneity, ventilation hyper-intensity or a combination thereof.

In one aspect, the individual may have normal $FEV_1$ at the time of said determining and said calculating.

In one aspect, the risk probability score may predict the probability of lung function decline over a period selected from three weeks to four months, or six months, or twelve months.

In one aspect, rapid (non-linear) lung function decline may be defined as a rate of change in longitudinal $FEV_1$ that falls below 1.5% predicted/year.

In one aspect, non-linear lung function decline may be defined by the FEV1-indicated exacerbation signal (FIES) score.

In one aspect, the one or more covariates may comprise a time-varying covariate.

In one aspect, the time-varying covariate may comprise infections with Pa, MRSA, CF-related diabetes and use of state insurance as a marker of socioeconomic status.

In one aspect, the biomarker may be one or more biomarkers selected from Table 1.

In one aspect, the biomarker may be one or more biomarkers selected from Table 2.

In one aspect, the biomarker may be one or more biomarkers selected from Table 3.

In one aspect, the biomarker may be one or more biomarkers selected from Table 4.

In one aspect, the individual may be diagnosed with cystic fibrosis (CF).

In one aspect, the individual may be diagnosed with cystic fibrosis (CF) and has a normal forced expiratory volume in one second ($FEV_1$) as measured by spirometry.

In one aspect, the individual may be a pediatric patient having cystic fibrosis (CF).

In one aspect, the individual may be a patient under the age of 13 years of age and having cystic fibrosis (CF).

In one aspect, the method may forecast lung function trajectory for a period of about three weeks to about six months, or about six months to about twelve months.

In one aspect, the method may further comprise applying a statistical algorithm to estimate correlation between a covariate value and predicted lung function.

In one aspect, the method may be carried out via a computer system, and wherein said method comprises capturing and displaying information related to said characterization of said individual using a graphical user interface (GUI).

In one aspect, the method may further comprise assessing a variable selected from one or more of sex, body mass index (BMI), pulmonary exacerbation (PE), number of hospitalizations, antibiotic status, infection status, and combinations thereof, in said individual.

In one aspect, the lung function decline may be defined by one or more of absolute change in $FEV_1$, rate of decline, risk of rapid decline, FIES.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Applicant analyzed serum samples from CF patients with severe (n=44) or mild (n=44) lung disease. Serum protein was purified via gel separation and liquid chromatography. Protein isoforms were identified using a cut off of at least 100 mass signatures per protein, coverage ranging from between about 15 and 100%. A combination of gel-based and MS-based label free quantitation was used to quantify the proteins. Pathways including the dataset members were analyzed.

In an exhaustive analysis of 61,942 serum protein isoforms, Applicant discovered a number of novel markers of CF lung disease severity and inflammation and found that combining their measurement (either grouped or individually depending on the marker) with Functional Data (FD) Analysis of $FEV_1$ can predict lung function decline by 6-18 months in advance. Applicant hypothesized that characterization of blood protein expression and modification in longitudinal samples integrated with monitoring of $FEV_1$ changes over time and through FD analysis can provide a sensitive and specific algorithm that predicts risk of CF lung disease progression which can be used to inform therapeutic intervention. Applicant has developed a novel statistical model to predict $FEV_1$ decline that have now been modified to include the novel biomarkers, and which can be adapted to include use of other clinical parameters besides $FEV_1$ to predict disease progression.

In particular, Applicant has identified and validated serum proteome changes in banked samples collected from patients with stable and declining $FEV_1$, developed a dynamic prediction model by integrating analyses of validated proteomic data with Functional Data (FD) analysis of longitudinal $FEV_1$ data to produce a novel diagnostic algorithm that identifies individuals at risk of lung function decline, and has evaluated the capacity of dynamic prediction modeling to identify CF patients who develop rapid pulmonary decline during adolescence in banked patient samples, testing the performance of the markers in banked samples from the EPIC study. Applicant's studies have the potential to fundamentally shift the nature of CF care from an evidence-based model of care decisions to individual patient-based care decisions informed through a predictive molecular and lung function disease platform and/or other clinical parameters. The disclosed algorithms of predictive biomarkers may be used to inform therapy choices and significantly improve CF care.

Proteomic studies may be conducted with LC MS/MS tandem mass spectrometric examination of patient serum. Each sample may be split into 3 fractions which can be analyzed by MS for 15 hours (including 3 technical replicates, 3 quality controls, and 2 wash runs preventing carry over). This allows deep screens to be conducted that capture information on approximately 7,000-10,000 protein isoforms and modification per sample with high confidence and accuracy and allows capture of low-level proteins where differences are more often found when comparing disease severity cohorts. These analyses are far more rigorous than the usual "service center" analysis, generating approximately 7-10 times more data. This increased data collection also increases the time for analysis (~10 fold) but provides rigor for detection of useful biomarkers and decreases false discovery rates, markedly increasing chances of success. For Functional Data (FD) and Functional Principle Component (FPC) analyses of $FEV_1$, Applicant's preliminary analyses build upon FD analysis and longitudinal models that have been applied to the CF Foundation Patient Registry (CFF-PR). Further analyses of the available cohort data at hand, providing strong evidence of associations and feasibility. The modeling disclosed herein blends established biostatistical approaches with modern FD approaches to characterize the nonlinear $FEV_1$ trajectory of individual patients and predicts subsequent decline. The disclosed methods may be used for in-clinic applications for decision aids for pre-clinic planning and at the time of patient encounters. Marker data correlation with $FEV_1$ was measured in multiple simulations and by appropriate statistical tests as described.

As noted above, three measures are generally used in monitoring CF disease progression and response to therapy: $FEV_1$, PE frequency, and BMI. Although these measures (particularly) lung function ($FEV_1$), have demonstrated steady improvement over the past two decades, a rapid deterioration of lung function persists, especially during adolescence (FIG. 3). See also https://cff.org/Research/Researcher-Resources/Patient-Registry/2019-Patient-Registry-Annual-Data_Report.pdf. While there are several potential interpretations for this observation, without intending to be limited by theory, it is believed that systemic changes reflected in the blood culminate in measurable pulmonary decline during this period (10-19 years of age).

Care for CF patients has advanced rapidly over the past two decades, with an unprecedented increase in patient longevity and quality of life. The reasons for these improvements include: a robust CFF-PR that collects data from nearly all CF patients in the US, allowing assessment of outcomes and treatment responses; standardization of care & therapies; and dramatic advances in new CF therapeutics, especially genotype-specific CFTR modulators such as KALYDECO® (4) and, to a lesser extent, ORKAMBI® (5), and more recently TRIKAFTA® (6). These advancements have increased the median survival of CF patients to 41 years (CFF-PR—2014), and >50% of CF patients alive today are adults. In many respects, research and care to improve CF patient outcomes has become the model for other rare diseases.

Applicant modified proteomic approaches (7-17) to examine serum from CF patients with mild or severe lung disease (13). Based on the experience of others in the cancer and cardiovascular fields, where conventional "shotgun" proteomics (which identifies 500-1000 proteins per sample) failed to distinguish disease severity in cohorts exhibiting the same disease, Applicant hypothesized that deeper screens would be necessary for CF studies. A proteomic analysis protocol was developed, involving multidimensional separation of proteins by abundant protein-adsorption columns and gel and column chromatography. This approach generated multiple fractions from each sample that were subjected to 15 hours of mass spectrometric analysis.

The following is a description of an exemplary proteomic analysis of CF patient serum. The approach may be applied to the analysis of any biological sample, for example, plasma, urine, cells, and other tissues. The methodology involves novel modifications of previously described approaches (Ziady A G, Sokolow A, Shank S, Corey D, Myers R, Plafker S, Kelley T J. Interaction with CREB binding protein modulates the activities of Nrf2 and NF-kappaB in cystic fibrosis airway epithelial cells. Am.J.Physiol Lung Cell Mol.Physiol 2012 June 1; 302(11): L1221-L1231. PMCID:PMC3379036; Chen J, Kinter M, Shank S, Cotton C, Kelley T J, Ziady A G. Dysfunction of Nrf-2 in CF epithelia leads to excess intracellular $H_2O_2$ and inflammatory cytokine production. PLoS.One. 2008; 3(10):

e3367; Ziady A G, Kinter M. Protein sequencing with tandem mass spectrometry. Methods Mol.Biol. 2009; 544: 325-41). Biological fluid or tissue lysate can be adsorbed for albumin or other highly expressed proteins using absorption columns. Protein may be precipitated from eluate or lysate with acetone (equilibrated to 90% acetone), dried, and rehydrated at a concentration of 5 mg/ml in 8 M urea, 2% CHAPS, 50 mM DTT in water. Greater than 45 µg of protein for a sample is generally subjected to SDS-PAGE, excised gel fragments containing all the protein from the sample are reduced and alkylated (to achieve more fractionation more gel fragments are cut), and subjected to in-gel tryptic digestion (20 ug/ml), and protein peptides are extracted for LC MS-MS. Extracts were acidified by equilibration in 0.1%-1% acid (e.g. acetic or formic acids), loaded onto a fractionation column (e.g. Thermo Fisher Scientific Acclaim PepMap $C_{18}$ column) at a flowrate of 0.15-0.5 ul/min, and subjected to nanospray tandem mass spectrometry with a mass spectrometer (e.g. Thermo Fisher Scientific LTQ Velos Pro spectrometer). Analysis in conducted in data-dependent mode capturing the 3-12 most abundant parent ions from full MS scans for fragmentation by collision induced dissociation (CID). Each gel fragment is run 3-9 times, and the data files from all runs are pooled for database analyses. In addition to multiple fractionation steps mass tolerance of 0.1-2.0 Da is used for parent ions and 0.01-0.7 Da for fragment ions to enhance the ability to quantitate low level proteins. Identified protein isoforms using 2-100% coverage cut off with >2 mass signatures per protein.

The EPIC Observational study includes >1,000 patients with annual blood samples for >10 years linked to the CFF-PR. 44 mild ($FEV_1$>85th percentile among CF patients) and 44 severe (<45th percentile) patient cohorts were matched based on age, gender, genotype, and P. aeruginosa infection status, then randomized and blinded before proteomic analysis. Applicant identified a total of 61,942 protein isoforms expressed across both cohorts, with 4751 proteins identified in at least half the subjects of each cohort. Data were normalized to a relative abundance (RA) measure (0 to 1) for each sample. For each isoform, RA was summarized (mean RA, number with RA >0, ratio of RA mild/severe) and, to reduce the data, a battery of paired statistical tests was performed on the matched samples: McNemar's, Wilcoxon Signed-Rank, paired Student's t test, and permutation of the difference.

Figure 4:
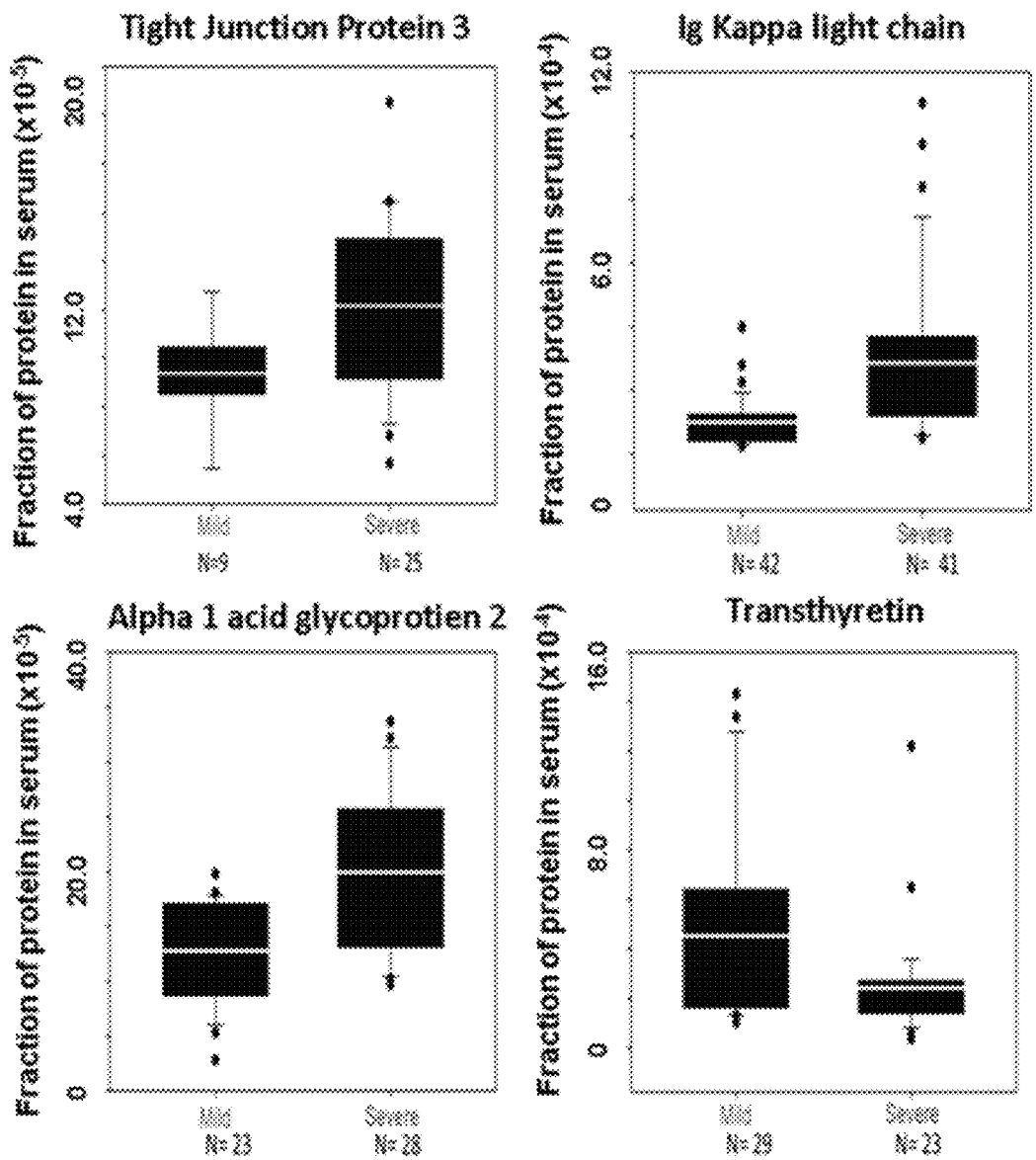
FIG. 4. Box plots of CF disease severity serum biomarkers. Example of differential expression identified serum biomarkers of lung disease severity. Forty-four candidates whose quantities differ by 0.35-5.4-fold between mild and severe disease have been identified.

In addition, a two-fold approach was used to identify protein isoforms as candidates for improved prediction of $FEV_1$. Functional principal components (FPC) scores were correlated with each protein expression level as described, measured using correlation coefficient $\hat{\rho}_{kcl}$. In addition, these isoforms were included as covariates in one-at-a-time modeling of Equation (3). These analyses generated the newly discovered 44 isoforms above which are the first serum biomarkers of CF disease severity identified by nonbiased analysis and are the basis for developing a lung function decline prediction model. Furthermore, the protein isoforms identified are baseline biomarkers of disease that segregate with disease severity when patient are stable. This is far more advantageous than presently available biomarkers such as C-reactive protein, which are only useful during acute exacerbation (20-24). The initial twenty biomarkers identified exhibited areas under the curve (AUC) of 0.69 or higher. These AUC values indicate that the biomarkers are superior to presently available markers of disease (21-24). Many of the biomarkers have either physiological or biological connections to CF (FIG. 4). For example, tight junction protein (TJP) 3 contains a PDZ motif and is a member of a family of proteins that interact with CFTR (25). Increases in serum IgG Kappa light chain levels are associated with chronic inflammation (26). Alpha-1-acid glycoprotein 2 is one of 4 biomarkers used to predict inflammation and mortality beyond CF (27), and transthyretin has been shown to be significantly decreased in CF patients compared to non-CF (28). Excessive inflammatory signaling in CF and an increase in patients with severe disease would be expected and is suggested by nonbiased biomarker identification.

CF lung disease demonstrates a steady decline that typically manifests during adolescence and young adulthood (29); however, rapid decline, characterized by accelerated loss of lung function relative to center-specific and/or population norms, is a ubiquitous event in the lives of patients (FIG. 1). Identifying when patients are at highest risk for rapid lung function decline is a significant gap in CF research, and offers the opportunity to intervene prior to irreversible lung damage. A key contributor to this gap has been the paucity of individualized predictive data on the specific timing and severity of lung function decline, and this is sustained by continued reliance on linear statistical approaches to fit nonlinear lung function decline (30). Moreover, phenotypes of patients at risk for rapid decline have not been well defined due to the analytically complex progression of CF (31).

In contrast to historical approaches, Applicant's biostatistical research on CF lung disease progression has been based on nonlinear longitudinal data analysis methodology and implementation in CF clinical/translational research. Applicant's approach fuses longitudinal data analysis together with FD analysis (32), a branch of statistics that offers tools to characterize nonlinear phenomena. FD analysis sheds light on complex pathophysiological relationships in different disease states, such as sleep disorders (33) and Alzheimer's disease (34).

Figure 5:
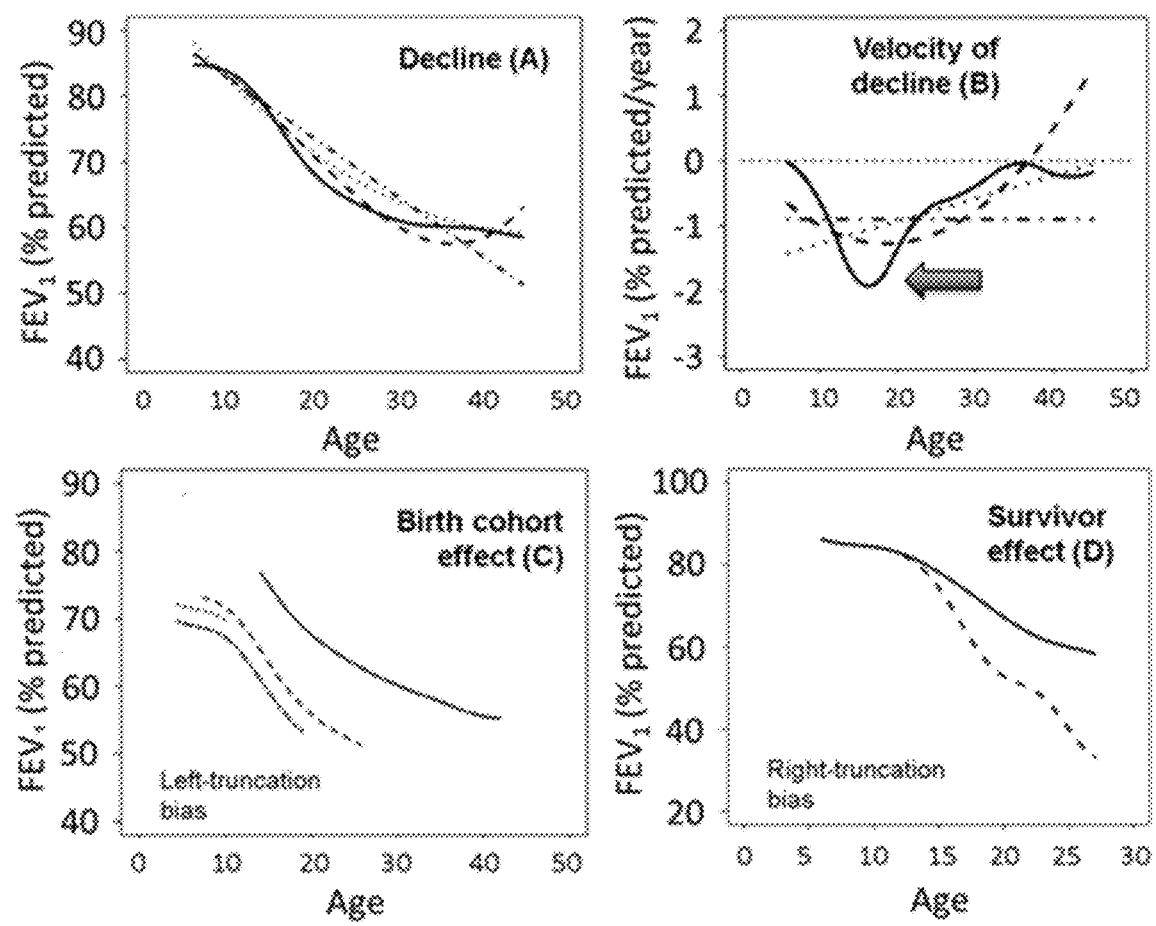
FIG. 5. Functional Data (FD) analysis model is superior to presently available models of lung function decline. CFF PR analyses with point estimates from FD analysis (solid line), cubic (dashed line), quadratic (dotted line) and conventional linear (dot-dash line) mixed models of decline (A) and rate of decline (B); stratified by birth cohorts born before 1981 (solid line), 1981-1988 (dashed line), 1989-1994 (dot-dash line), and after 1994 (dotted line) (C); stratified by survival (solid line) and death (dashed line) for patients less than 19 years of age (D). The FD model in (A) reflected the dynamic status of lung function during young adolescence/early adulthood; traditional models found no changes and even indicated gains in lung function (e.g. cubic). The arrow at the "dip" in (B) shows 1) Patients attained most rapid decline at median age (IQR) 16.3 (13.5, 21.0) years; 2) Degree of maximal $FEV_{10}\%$ loss was variable (mean: 1.98% pred/yr, 95% CI: 1.86, 2.10). Longitudinal $FEV_{10}\%$ measures shared correlation for up to 9 years, highlighting the potential of short-term clinical interventions to impact long-term lung function. Further subgroup analysis revealed that $FEV_{10}\%$ curves vary according to survivorship and birth cohort (C-D), highlighting left- and right-truncation biases, respectively.

Applicant has used the CFF-PR to demonstrate that FD analysis predicts CF lung-function decline with improved accuracy compared to traditional linear approaches (35) and can be used to identify phenotypes of rapid decline. Historically, CF registries (such as the CFF-PR) have carefully maintained lung function data to track disease, but have not utilized data for prognostic care (36). The disclosed dynamic prediction models using FD analysis have leveraged this rich longitudinal data to develop more accurate tools that predict disease course and in turn help prioritize interventions for the individual patient (FIG. 5). The disclosed methods meaningfully contribute to CF precision medicine, an area that has been noticeably understudied (37).

Major advancements in personalized medicine in CF may change the clinical course of the disease (38). Applicant has successfully used FD analysis to characterize nonlinear population-level lung function decline of cystic fibrosis patients in the US. Applicant's CFF-PR study of over 30,000 patients and 500,000 $FEV_1$% measurements utilized longitudinal FD methods to address nonlinearity and serial correlation (35). Applicant estimated degree (velocity) and timing of rapid decline by taking derivatives in Applicant's model and traditional models. The covariance structure included exponential decay and random intercepts. The FD model was superior, compared to traditional models, in terms of estimating the onset and severity of rapid $FEV_1$% decline and model validity (FIG. 5). Applicant's results indicate that nonlinear, heterogeneous lung disease progression prevails, and the ability of FD models to establish CF phenotypes predictive of rapid decline.

Applicant has further identified $FEV_1$ phenotypes corresponding to early, middle and late rapid decline in patients 6-21 years of age. Using the CFF-PR data, modes of variation in $FEV_1$ progression are characterized as functional principal components (39). The majority of variation (first functional principal component: 94%) among patient profiles are characterized by differences in mean longitudinal $FEV_1$ trajectories. Average degree of rapid decline was similar among phenotypes (roughly −3% predicted/year); however, average timing differed, with early, middle and late phenotypes experiencing rapid decline at 12.9, 16.3 and 18.5 years of age, respectively. Individuals with the late phenotype had the highest initial $FEV_1$ but experienced the greatest loss of lung function.

$FEV_1$ variation coupled with nonlinear progression over age produces an uneven, "saw-tooth" shape for each individual's trajectory (see FIG. 1), making it difficult to model the time-course of a patient's underlying lung function and utilize it for earlier detection and intervention. To further improve the predictive accuracy of rapid decline, Applicant utilized FD analysis to develop a dynamic prediction model of CF progression that accounts for the variation in $FEV_1$. To leverage existing data for individual patient prediction, a dynamic prediction model recently proposed by Diggle et al (40) was expanded to accommodate the jagged, nonlinear shape of $FEV_1$ trajectories using CFF-PR data on 27,296 patients >6 years who each had 1 to 89 $FEV_1$ measurements. Covariates in the model were birth cohort, copies of delF508, baseline $FEV_1$, and male gender. Time-varying covariates included infections with Pa, MRSA, CF-related diabetes and use of state insurance as a marker of socioeconomic status. Interactions between each of these covariates with time were examined. To account for irregular follow up and occurrence of PEs, rolling, time-varying covariates were included for the numbers of follow up visits and PEs within the last year. Although these covariates are not commonly used in the literature, their inclusion improved predictive performance of the model based on residual analyses. All covariates were statistically significant (P<0.05) with the exception of state insurance (P=0.07).

Applicant evaluated predictive ability of the proposed stochastic model using a preliminary sample size of 36 subjects with available data on proteomic markers. These subjects contributed a total of 1975 $FEV_i$ longitudinal observations. The subjects were randomly split, with 80% contributing measurements to the training dataset for model building, and 20% providing data for the validation step. Using the training dataset, a model that included terms to model nonlinear progression of $FEV_1$ over age (cubic b-splines), a severity indicator established by the EPIC study (binary variable) was used; also included were terms for the markers and their interaction with age. Severe classification met statistical significance (P<0.05).

Predictive accuracy, measured using Akaike information criterion (AIC), was superior in this model compared to a model that excluded the proteomic marker terms. Validation metrics that were assessed in the test cohort included mean absolute deviation (MAD), root mean-square error (RMSE), mean absolute percentage error (MAPE) and correlation between predicted values and observed values. Based on the $FEV_1$ scale, validation metrics showed relatively small prediction error. MAPE, which measures forecast accuracy as percent difference between actual $FEV_1$ and predicted $FEV_1$, shows that there is relatively small error between projected and actual $FEV_1$ values. Correlation between observed and predicted values is excellent (above 0.80) and is significantly higher than presently available measures (range from 0.54-0.71).

Applicant also assessed the predictive value of proteomic markers using FD and dynamic prediction as described above. A number of the biomarkers were included as covariates and their interaction with age in the Reduced Model. Other covariates included in the model were age-specific components to fit the $FEV_1$ trajectory, as shown in the FD analysis in previous studies, and the Mild/Severe designation from Applicant's original study. The model showed that proteomic markers were significantly associated with mean $FEV_1$ (coefficient: −8.03, SE: 4.07, z=−2.0, P=0.04) and approached significance in their association with $FEV_1$ decline (coefficient for interaction: 1.03, SE: 0.79, z=1.3, P=0.19).

Figure 6:
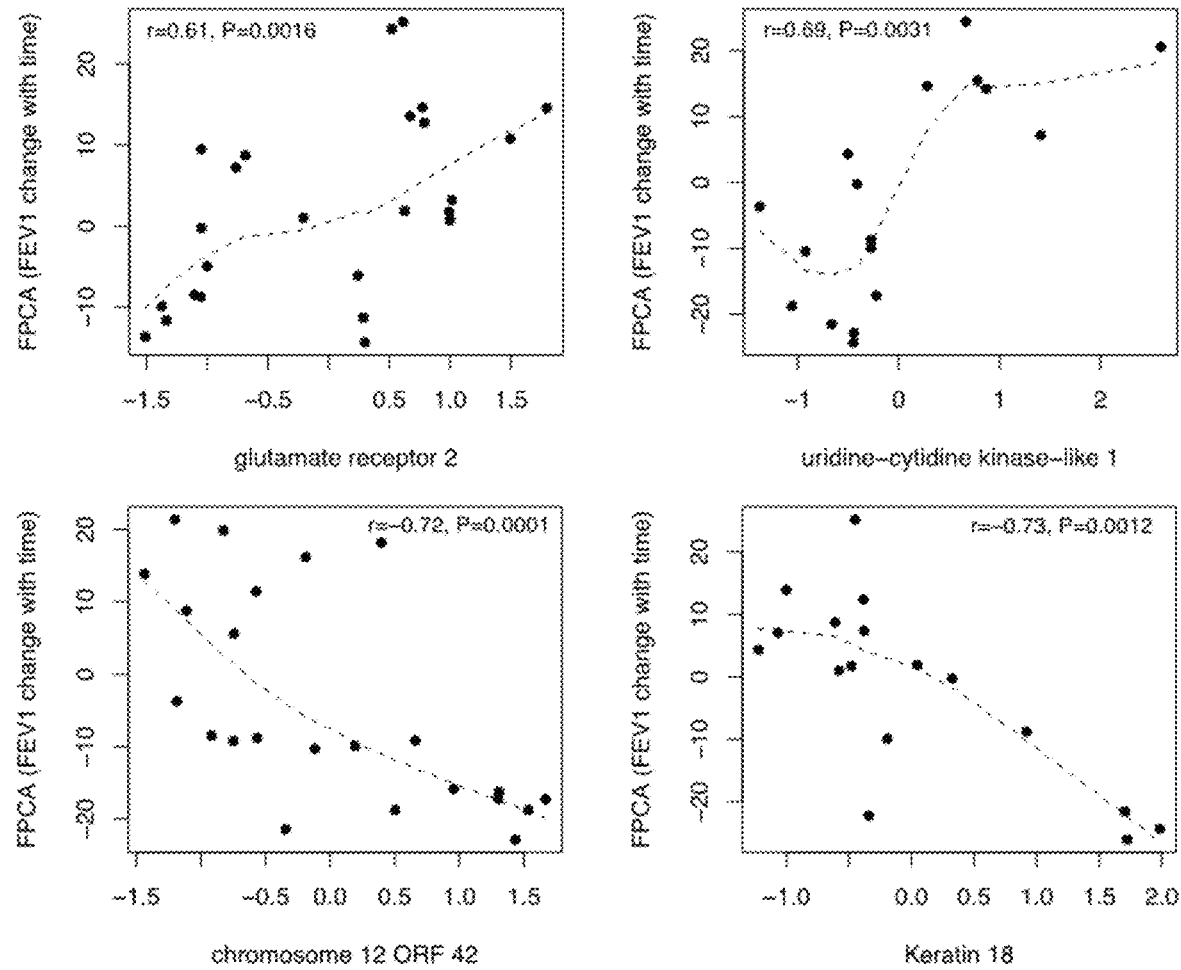
FIG. 6. Biomarker correlation with functional principle component (FPCA) analysis of lung function. Examples shown for 4 of 18 biomarkers discovered in preliminary cross-sectional proteomic analyses that significantly correlate with FPCA analysis of $FEV_1$. The first principle component score (FPC1, y-axis); the thick dashed black line is the fit to the data using a scatterplot smoother; positive association (r) indicates that higher values of these markers may lead to worsening $FEV_1$ trajectory, while negative associates (−4) indicates that higher values of these markers correspond to improvements in the $FEV_1$ trajectory. Although these studies were conducted in discovery mode to capture the maximal number of biomarkers, data on individual markers may be improved under targeted MS and ELISA analyses.

Serum proteome changes in banked samples collected from patients with stable and declining $FEV_1$ can be validated as follows. Preliminary studies generated serum biomarkers that segregate CF disease severity during periods of disease stability. Conduct of longitudinal analyses to validate the predictive power of biomarkers in samples from the EPIC CF cohort may provide the confidence for future modeling. Proteomic discovery studies in 88 cross sectional samples identified 20 biomarker changes that segregated CF patient lung disease severity in adolescence. Data collected from proteomic screens can benefit statistical models of lung function decline. To determine the utility of the molecular markers, top 20 molecular biomarkers were examined for their ability to enhance lung function decline modeling. Initial studies are cross sectional and conducted in discovery mode. Multiple (>10) simulations of functional principle component (FPCA) analyses of $FEV_1$ including data for each of the top 20 markers showed significant correlations between the behavior of novel markers and $FEV_1$ decline (FIG. 6).

The discovery cross sectional data was collected by high throughput discovery mode MS analysis. Data from both targeted MS and ELISA may be integrated with FD analysis, either in combination or separately. Biomarkers discovered in preliminary cross-sectional studies for prediction of future $FEV_1$ decline, may be validated using targeted proteomics and ELISA analyses of banked serum samples from the EPIC Observational study.

Samples. Analysis of samples from EPIC can be used to evaluate the predictive capacity of the biomarkers 1-5 years in advance of cohort segregation by $FEV_1$. These can be compared with additional candidate biomarkers, and secondary analyses can be used to examine relationships to established predictors of disease severity, including PEs, BMI, and microbiology. The choice of the EPIC samples may be based on the availability of longitudinal samples for patients that cover the age range where significant lung-function decline is observed (e.g., early teen years). The longitudinal proteomic profiles can be categorized for subjects already profiled at 'baseline' or time zero. This will determine if the baseline protein markers are able to predict subsequent disease progression. Preliminary data using $FEV_1$ alone shows a fairly even distribution of different phenotypes to examine: stable high (n=16) and stable low (n=13) (total stable, n=29) and rapid lung-function decline among 'mild' lung disease subjects at baseline (n=10) and in those with more severe disease at baseline (n=12) (total 'decliners', n=22). The remaining patients (29 of the original 88) may be used to supplement the 'extreme phenotype' data and provide information on proteomic profiles across the continuum of clinical presentation.

Mass spectrometry. Applicant has developed useful mass spectrometry-based approaches for the identification/quantitation of thousands of proteins in serum samples. Protein is prepared from serum using albumin adsorption columns and gel and column chromatography, followed by tryptic digestion. Following preparation of whole-serum protein, serum-protein peptides are extracted and subjected to data-dependent sequencing and mass spectrometry analysis, as previously described (33-33; 35; 37-41; 42). Briefly, the samples are loaded in a HPLC system autosampler and eluted by reverse-phase chromatography into a mass spectrometer fitted with a nanospray ion source for analysis. The mass analyzer is set up for a data-dependent mode using dynamic exclusion settings: repeat count=1; repeat duration=0.5 minutes; exclusion list size=50; exclusion duration=1.5 minutes; exclusion mass width=1.5 amu. Collision-induced dissociation (CID) is used to fragment peptides, and CID spectra are searched against a human fasta database using Proteome Discoverer™ software. A decoy database is used to control for false discovery. A threshold filter of >2.0 for peptide XCorr score is used for sequence identification. For preliminary studies, this produced a range of coverage for identified proteins of 5.15%-79.91% and an average of 10.03% for all proteins identified. This high stringency filter of data provides more reliable quantitation, and aids the reduction of data in follow-up statistical analyses.

Given the emphasis on early detection of rapid disease progression from the CF community, the availability of extensive demographic, clinical, molecular and environmental measurements from the EPIC data augmenting the CFF-PR, and the emergence of promising methodologic approaches for analysis, the disclosed methods allow for improved dynamic prediction models of rapid decline through integration of validated proteomic markers. Rosenfeld and colleagues (47) have utilized part of the EPIC cohort (n=946 patients who were Pa-negative at enrollment) to study associations between data collected in the year after the first pulmonary function test (PFT) and subsequent rate of $FEV_1$ decline (mean±SD follow up: 6.2±1.3 years). Through multivariable linear modeling of age-related $FEV_1$ progression with generalized estimating equations, they confirmed established risk factors for decline (e.g., female gender) and identified a new risk factor (*S. maltophilia*). Although this was a relatively young cohort (mean±SD age at entry: 7.9±2.0 years) with mild CF disease, they observed a similar "ceiling" effect to what was originally described by Konstan and colleagues and previously found by Applicant.

Figure 7:
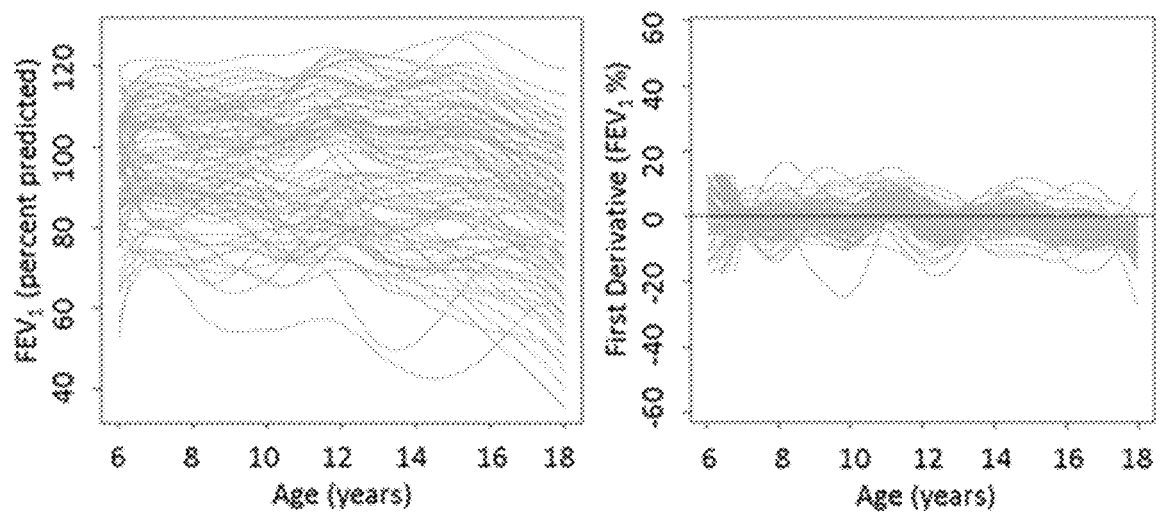
FIG. 7. On the left, smoothed $FEV_1$ observed over age (in years) for the EPIC cohort. On the right, the corresponding rate of change in $FEV_1$ (expressed as % predicted/year) over age.

Modes of variation in $FEV_1$ decline for the 88 EPIC subjects (44 Mild, 44 Severe, described above) with longitudinal PFT and cross-sectional proteomic data were examined using functional principal components, the FD analysis technique to the CFF-PR, in order to characterize rapid decline during adolescence and adulthood. Median (IQR) age at entry was 12.5 (9.8-15.3) years; follow-up ranged from 20 to 216 PFTs per patient. Individual smooth curves from the FD analysis had substantial variation between patients and within an individual patient over time (FIG. 7). The first functional principal component explained 85.3% of the variation in $FEV_1$, suggesting that the individual trajectories were similar to the overall mean curve but shifted according to initial $FEV_1$. The four subsequently ordered functional principal components, which reflect higher-order modes of oscillatory variation, explained 8.1%, 3.7%, 1.8% and 1.0%, respectively.

Rapid decline was observed in different periods of age for the majority of individuals in the cohort. Most rapid decline during the observation period occurred, on average, at 15.5±2.3 years of age, with decline of 3.9+4.2% predicted/year. To understand how rapid decline in this cohort is related to proteomic markers, the association between each FD parameter and marker of interest was estimated using Spearman's r. To adjust for multiplicity in this preliminary analysis, associations with P<0.01 were considered statistically significant. Several associations were found between proteomic markers and the first functional principal component for $FEV_1$ (lower values of this component correspond to milder disease); several markers including glutamate receptor 2 isoform 4, alpha-1-acid glycoprotein 2 precursor, immunoglobulin alpha-1 heavy chain constant region, anti-Entamoeba histolytica immunoglobulin kappa light chain, anti-HBsAg immunoglobulin Fab kappa chain, AT-rich interactive domain-containing protein 4A isoform I, and uridine-cytidine kinase-like 1 isoform 2 were positively associated (range of r: 0.37 to 0.69); additional markers including unconventional myosin-XVIIIa isoform X1, chromosome 12 OPR 42, isoform CRA c, and Keratin 18 were negatively associated (range of r: −0.73 to −0.54). Degree of rapid decline was negatively associated with markers A-kinase anchor protein 3 and Keratin 18 (r: −0.76 and −0.72, respectively). Patients who experienced rapid decline at a younger age tended to have elevated levels of markers alpha-1-acid glycoprotein 2 precursor, anti-Entamoeba histolytica immunoglobulin kappa light chain, and anti-HBsAg immunoglobulin Fab kappa chain, corresponding to negative associations (range of r: −0.55 to −0.43), and lower levels of chromosome 12 open reading frame 42, isoform CRA c (r: 0.55) (see FIG. 6).

The disclosed dynamic prediction model uses patient-specific information from the EPIC cohort while incorporating parameter estimates from Applicant's recent large-scale CFF-PR study to predict the onset of rapid decline. The model takes into account observed lung function for the patient at each time point, the mean $FEV_1$ evolution for each patient, and encompasses covariates with corresponding association parameters. Normal distribution of the data provides patient-specific heterogeneity between $FEV_1$ trajectories. Furthermore, a stochastic process is used to reflect the "saw tooth" variation over time for individual patients (see FIG. 1); integrated Brownian motion is used to depict this process. Normally distributed measurement error from the PFT is accounted for. Finally, data for the level of markers is added to the model. The covariance functions and estimation algorithm have been described previously (40). The model for the CFF-PR is implemented using the lmenssp package (48) in R (R Foundation for Statistical Computing, Vienna, Austria). The covariates that considered from the CFF-PR may be expanded to include additional factors available from the EPIC study. Candidate molecular markers can be directly added as covariates, and the association parameters can be denoted to fit the model on smaller data. If marker data were available from all CFF-PR subjects, this new model could be called the "Full Model". A so-called "Reduced Model" can be fit using detailed data from the EPIC cohort.

Figure 8:
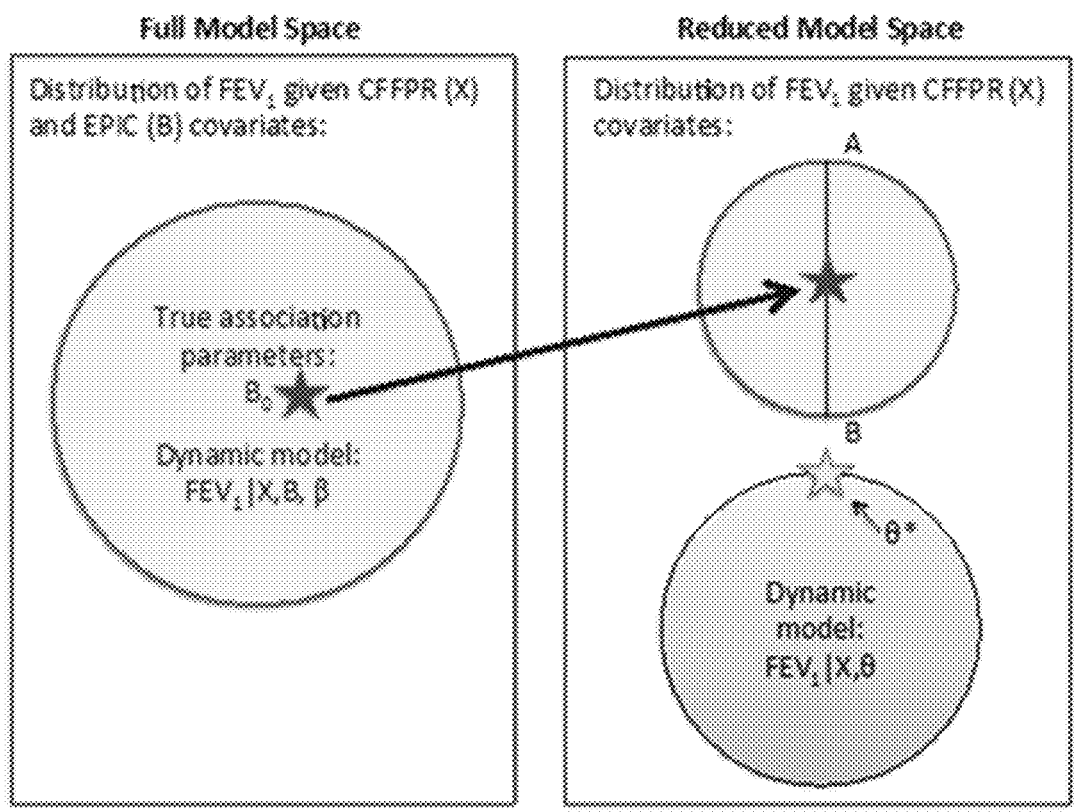
FIG. 8. Schematic of biomarker integrated dynamic modelling of $FEV_1$. On the left, the full model space for all CF patients and possible covariates; the large circle is the space for the full dynamic prediction model, and the star denotes the true associates between each CFFPR/EPIC covariate and rapid (non-linear) decline. On the bottom right, the bottom circle is the space for the external data model that is fit to the CFFPR; the bottom star marks the parameters $\ominus^*$ that would minimize the mathematical distance between the full model with all covariates and the model with only the CFFPR covariates. On the upper right, the circle shows a star being mapped to the same space as the external model, in order to perform model calibration and obtain more efficient, unbiased estimates.
Figure 9:
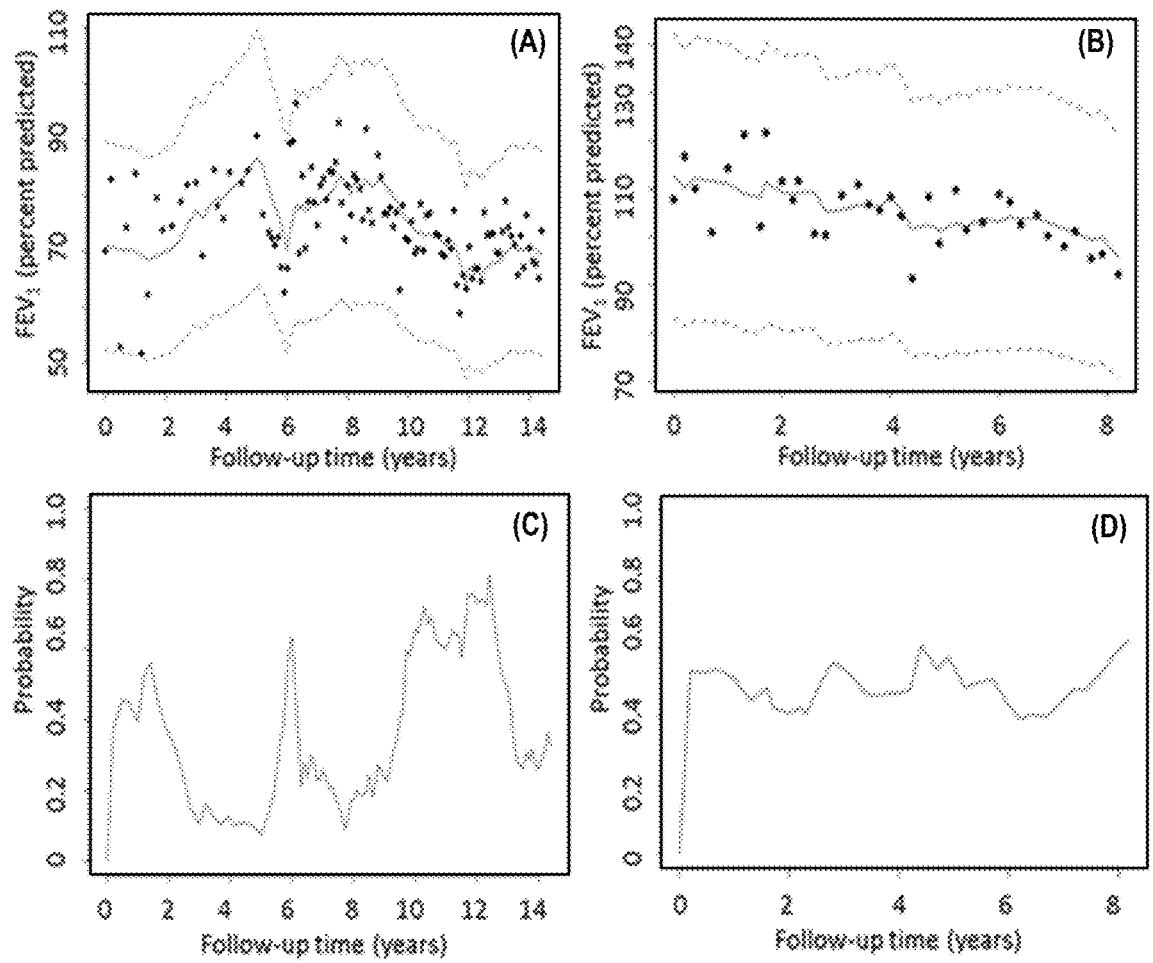
FIG. 9. Dynamic prediction modeling. Dynamic predictions for female (left column) and male (right column) CF patients. In the left column, the female patient had data on 111 encounters in the CFFPR; her age at entry (follow-up time: 0 years on the axis) was 6.1 years. Her decline in $FEV_1$ was highly variable over time (A) with probability of rapid decline on the y-axis in (B); periods of increased risk of rapid (non-linear) decline shown at 16-18 years of age (follow-up time: 10-12 years on the x-axis). By contrast, the male patient (right column) had steadier decline and less availability (C). He had data on 35 encounters in the CFFPR; his age at entry was 14.5 years. He had decreased risk of rapid (non-linear) decline (D), compared to the female patient. Rapid decline was defined as a rate of change in longitudinal $FEV_1$ that fell below 1.5% predicted/year. Threshold was determined as previous reported (53).
Figure 10:
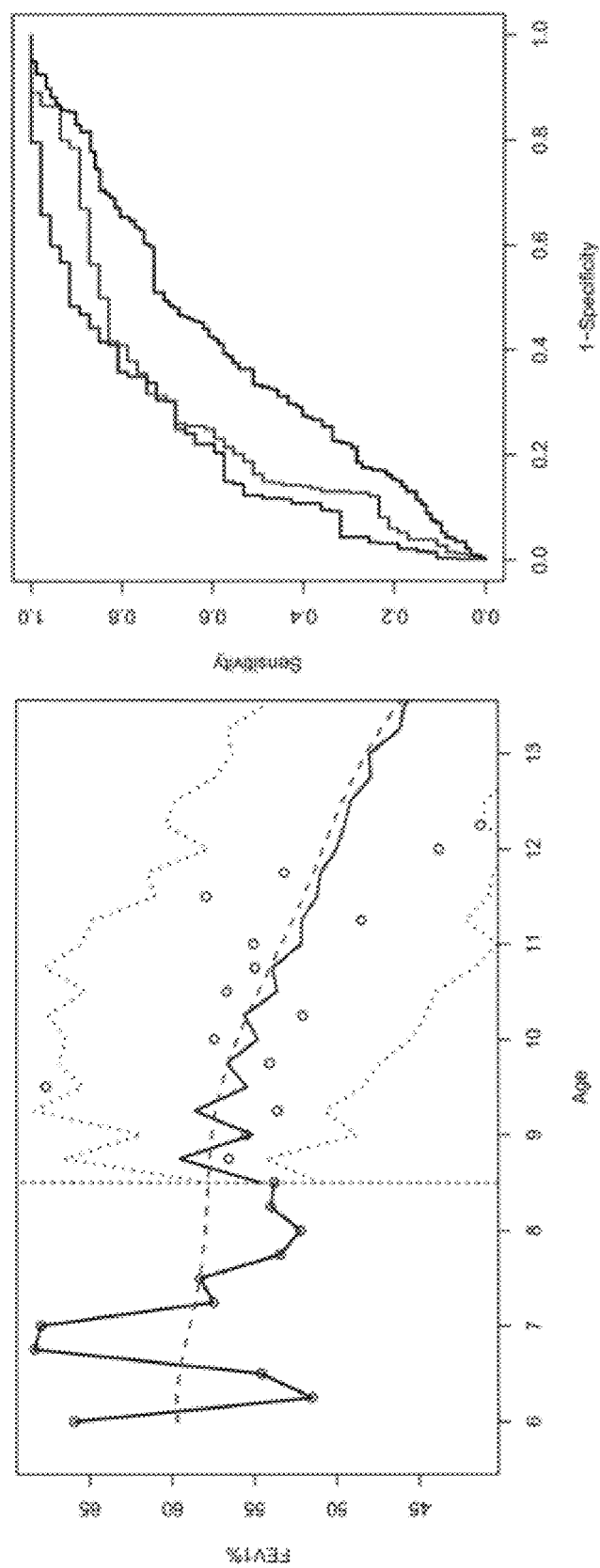
FIG. 10. $FEV_1$ and clinical event forecasting performance. Left panel: the $FEV_1$ forecasting performance for a representative subject from the CFF-PR. Observed $FEV_1$ data (black dots) is fitted with the model (black line) over age; the model was used to predict his subsequent $FEV_1$ data shown after the vertical bar in the plot. To the right of the vertical bar, the solid line and dashed lines are the predicted FEV1 and corresponding 95% confidence bands. The dotted line is the smooth, population-level trajectory for $FEV_1$. Right Panel: the ROC curves for the model fit to PE data. The upper curve is the proposed model, which has the highest AUC (0.74), followed by a model with no subject-level effect and logistic regression (0.68 and 0.61, respectively).

A novel semiparametric "big data" calibration approach (49) may be adapted to examine predictive value of the markers. The approach can be geometrically described (FIG. 8). The algorithm may be programmed using R. Briefly, constrained maximum likelihood estimation may be implemented to fit the Reduced Model described above while accounting for the parameter estimates found from the External Model on the CFF-PR. This estimation, as shown by Chatterjee, produces unbiased estimates with lower standard errors for the Full Model, compared to fitting the Reduced Model alone. The calibrated estimates may be used to determine whether the addition of molecular markers and other EPIC covariates improve prediction of rapid decline. Improved prediction may be assessed by 1) examining the interaction of a given biomarker with age in the Reduced Model; 2) using model diagnostics; 3) fit statistics (e.g., AIC, BIC); 4) the likelihood ratio test to model; an example of the risk function for a patient is in FIG. 9. To validate predictive accuracy, analysis with 20% of the EPIC cohort removed from the modeling may be performed. This subset of the cohort will have covariate data added to the model to check predictive accuracy; metrics here may include mean absolute deviation (MAD) and mean square error (MSE), which have been previously used by Applicant with good success (35).

The predictive value of a subset of proteomic markers is assessed based on the Reduced Model using FD and dynamic prediction as described above. Applicant included the protein similar to dual specificity phosphatase 9, partial as a covariate and its interaction with age in the Reduced Model. Other covariates included in the model were age-specific components to fit the $FEV_1$ trajectory, as shown in the FD analysis in previous studies, and the mild/severe designation from the original study. The proteomic marker was available on 36 EPIC subjects (23 Mild, 13 Severe); these subjects were 6.3 (6.6-7.7) years of age with $FEV_1$ of 95.5 (61-138) % predicted. The median (range) number of PFTs (per subject was 54 (20-93); per-subject follow-up was 11.5 (9.4-12) years. The model showed the proteomic marker was significantly associated with mean $FEV_1$ (coefficient: −8.03, SE: 4.07, z=−2.0, P=0.04) and approached significance in its association with $FEV_1$ decline (coefficient for interaction: 1.03, SE: 0.79, z=1.3, P=0.19). These results suggest that the biomarker has a negative association with overall mean $FEV_1$ but may have a positive effect on rate of $FEV_1$ decline.

Covariate selection may also be performed using Bayesian Ensemble Trees (BET) (50). BET was developed by Applicant as an approach to perform variable selection for modeling $FEV_1$ decline. This approach utilizes the ensemble of classification and regression trees (CART). Each constituent tree is estimated with a subset of similar data, and can be used for covariate selection and imputation of missing data (51). The form of each marker covariate will be modified to examine potential lagged effects on $FEV_1$ decline. For select markers, associations with $FEV_1$ decline can be simultaneously examined using joint models for high-dimensional data (52). To investigate the impact of the collection of markers on rapid decline, PCA may be used to develop composite score(s); the score data may then be included in the model as covariate(s). Alternatively, BET may be used to create step functions representing rapid decline. The step functions can be subsequently smoothed to represent rate of $FEV_1$ decline and construct individual probabilities of rapid decline similar to the dynamic prediction model or risk scores for rapid decline.

Four Bayesian penalized regression approaches for the previously described Gaussian linear mixed effects model with non-stationary covariance to account for the complicated structure of longitudinal lung-function data while simultaneously estimating unknown parameters and selecting protein isoforms to improve the prediction model. These penalized regression models induce variable selection by shrinking the coefficient of irrelevant variables toward zero while simultaneously keeping the relevant variables in the final model. Different types of shrinkage priors are considered and evaluated to induce variable selection in a fully Bayesian framework.

Model setup: The main form of the Bayesian penalized regression model implemented for the non-stationary Gaussian linear mixed effect model can be written as:

$$Y_{ij} = \alpha_0 + \alpha_1 t_{ij} + \Sigma_{k=1} \beta_k X_{ik} + U_i + W_i(t_{ij}) + Z_{ij},$$

where $Y_{ij}$ is lung function measurement for subject i at time point $t_{ij}$, i=1, . . . , N; j=1, . . . , $n_i$; k=1, . . . , p. The $\beta_k$'s are the coefficients of the proteomic biomarkers that we want to shrink towards zero to induce simultaneous variable selection and $X_{ik}$ is the covariate matrix for the proteomic biomarkers. Between-patient heterogeneity is incorporated in the model with a random intercept term $U_i$, where $U_i \sim N(0, \omega^2)$. The term $W_i(t_{ij})$ denotes realizations from the zero-mean, continuous-time integrated Brownian motion process, and $Z_{ij} \sim N(0, \tau^2)$ represents iid measurement error. This model can be written as, $Y_i \sim MVN(\psi_i \alpha + X_i \beta, V_i(\phi))$, where $V_i(\phi) = \omega^2 J_i + \sigma^2 R_i + \tau^2 I_i$, and it is reparametrized as $V_i(\phi) = \tau^2(\phi_1 J_i + \phi_2 R_i + I_i)$ where $J_i$ is $n_i \times n_i$ matrix of ones, $I_i$ is $n_i \times n_i$ identity matrix, and $R_i$ is $n_i \times n_i$ matrix with (j, k)$^{th}$ element is, $$\frac{\min(t_{ij}, t_{ik})^2}{2}\left(\max(t_{ij}, t_{ik}) - \frac{\min(t_{ij}, t_{ik})}{3}\right).$$

To obtain different types of penalized regression models, the following priors are assigned to complete model specification;

Bayesian Least Absolute Shrinkage Selection Operator (lasso): Preferable when the goal is obtaining a sparse set of potential predictive proteomic biomarkers. λ is the penalty parameter which controls the amount of penalty being applied to the coefficients of predictors (proteomic biomarkers) to force them near zero. The following prior distributions are assumed:

$$\beta | \tau^2, a_1^2, \ldots a_p^2 \sim MVN(0, \tau^2 D_L)$$

$$D_L = \mathrm{diag}(a_1^2, \ldots a_p^2)$$

$$a_j^2 | \lambda \sim \frac{\lambda^2}{2} e^{-\lambda^2 a_j^2/2}$$

$$\lambda^2 \sim \mathrm{Gamma}\ (r, \delta).$$

Bayesian Adaptive Lasso: Similar to the Bayesian Lasso described above but assigns different amount of penalty to different coefficients based on their importance.

$$a_j^2 | \lambda \sim \frac{\lambda^2}{2} e^{-\lambda^2 a_j^2/2}$$

$$\lambda_j^2 \sim \mathrm{Gamma}\ (r, \delta).$$

Bayesian Ridge Regression: Bayesian ridge regression is more preferable when the predictors are highly correlated. When there exists multicollinearity between predictors, the ridge regression deals with collinearity and applies continuous shrinkage and improves prediction performance through a bias-variance trade-off.

$$\beta | \tau^2, \lambda \sim MVN(0, \tau^2 D_R)$$

$$D_R = \text{diag}(\lambda^2)$$

Bayesian Elastic-Net: This method merges the features of both the lasso and the ridge and takes into account both sparsity and correlation structure of the data. Hence, the elastic net simultaneously induces variable selection by forcing the coefficients of redundant variables toward zero and selection of groups of correlated covariates and handles with multicollinear predictors.

$$\beta | \tau^2, a_1^2, \ldots a_p^2 \sim MVN(0, \tau^2 D_{EN})$$

$$D_{EN} = \text{diag}\{(a_1^{-2} + \lambda_2)^{-1}, \ldots, (a_p^{-2} + \lambda_2)^{-1}\}$$

$$a_j^2 | \lambda_1 \sim \frac{\lambda_1^2}{2} e^{-\lambda_1^2 a_j^2/2}$$

$$\lambda_1^2 \sim \text{Gamma}(r_1, \delta_1) \text{ and } \lambda_2^2 \sim \text{Gamma}(r_2, \delta_2).$$

Further, assigned are non-informative uniform prior for $\alpha_0$ and $\alpha_1$, flat uniform priors for $\phi_1$ and $\phi_2$, non-informative scale invariant prior $$\frac{1}{\tau^2}$$

for $\tau^2$ under all four models mentioned above.

Given the priors and the data likelihood, the posterior distributions of all unknown parameters are obtained by using Bayes' theorem. Unknown parameters and hyperparameters of each model are estimated by sampling from their conditional posterior distributions through MCMC algorithm. Each MCMC algorithm is creating code in R software.

The need for analysis of samples collected from subject undergoing modulator therapy is critical, as CFTR modulation has become the standard of care, and this will likely influence the behavior of molecular markers.

Example 1. Improvement of Predicting Lung Function Decline

Figure 11:
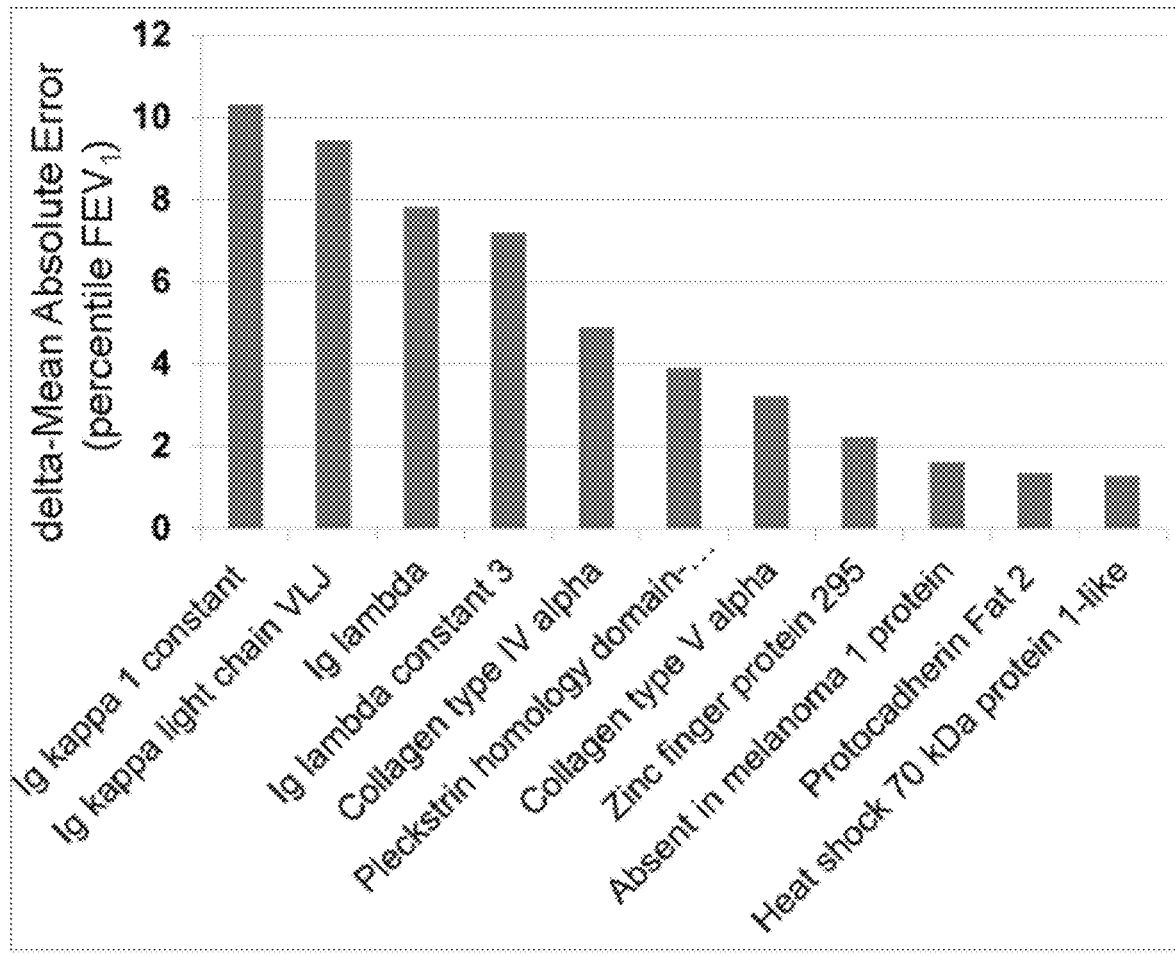
FIG. 11. Marker improvement of $FEV_1$ prediction. Protein markers in serum improve the ability to predict future lung function decline, reducing the error in prediction of absolute $FEV_1$ by up to greater than 10 percentile points.

A number of interventional therapies are used to stave off lung function decline in patients with cystic fibrosis, including antibiotics, anti-inflammatory therapies, hypertonic saline to increase clearance, and others. The largest challenge in CF care is projecting lung function performance and intervening accordingly. Currently, intervention occurs when clear declines in lung function as measured by $FEV_1$ and other lagging indicators are observed. The approach of intervening once lung function has already declined rarely restores lost lung function; therefore, intervening before lung function decline occurs can be beneficial by preventing decline. An example that captures the range of the performance of some of the markers in Table 1 at improving the prediction of lung function is shown in FIG. 11.

Tandem mass spectrometry or ELISA may be used to measure the levels of Ig lambda and Ig kappa chains in collections of blood from a CF patient during their regular hospital visits. The levels of these proteins would be inserted into the algorithm described herein along with the measurements of $FEV_f$ for the patient over a number of hospital visits. The markers can be used individually or in combination. The algorithm will return a score that reflects the risk of lung function decline in the next 18 months. Based on the score returned a physician may choose to be more aggressive with conventional anti-inflammatory therapy to reduce or prevent impeding lung function decline or follow the usual regiment of care if the score does not indicate a high risk of future lung function decline.

Figure 12:
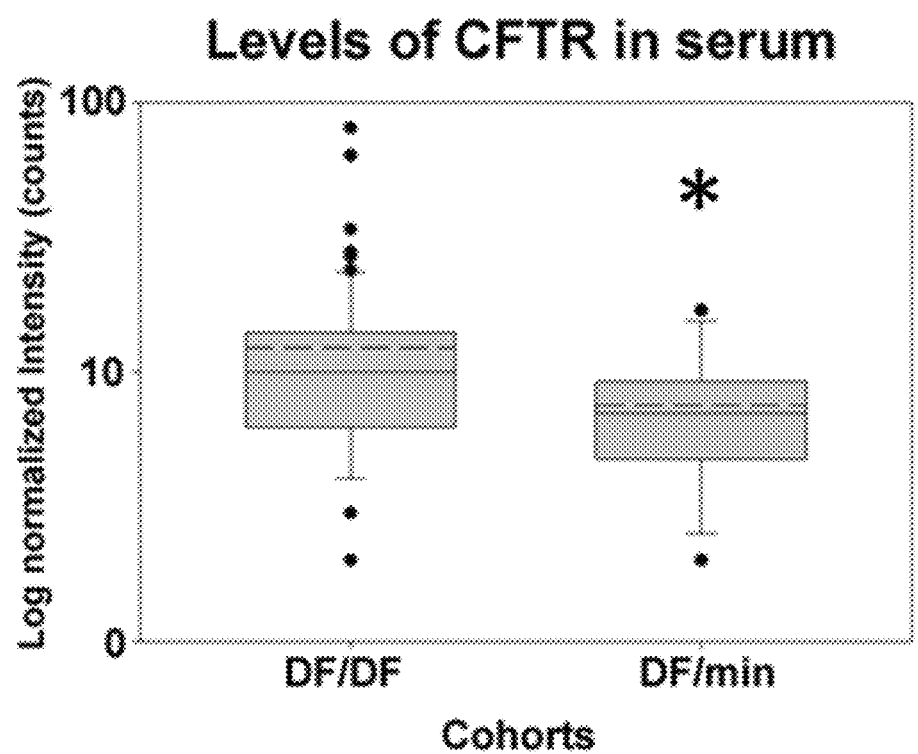
FIG. 12. Quantitation of CFTR by tandem mass spectrometry. Fractionated serum is analyzed for levels of CFTR in homozygote F507del patients versus those with 1 F508del allele with the other allele producing minimal protein. Solid line is median. Dashed line is average. DF/DF average±SEM=12.34±1.44 vs DF/min average±SEV=7.5±1.09. * connotes significant difference, p=0.0092.

Example 2. Measurement of CFTR to Assess the Success of the Delivery of CFTR Gene Therapy A large challenge for gene therapy with the CFTR gene is the lack of effective measures of the delivered CFTR transgene expression. The technology described herein allows us to measure the levels of full length or any portion of CFTR protein. FIG. 12 shows difference measured in the levels of CFTR between patients homozygous for the F508del mutation compared with the levels measured in the serum of patients heterozygous for F508del and various mutations that express minimal levels of protein. The difference observed by the technology claimed here of 1.65-fold reflects the expected higher levels of CFTR expression in the homozygous group. An example of using this technology would be in the context of a CFTR gene therapy trial. In such a trial, measuring the expression of the delivered transgene CFTR would be necessary. The technology described herein may be used to measure level of full length or a portion of CFTR in the serum, plasma, and/or bronchoalveolar lavage to assess the efficiency of gene delivery. An increase in levels of CFTR in serum, for example, would indicate successful delivery of CFTR.

Example 3

Rigorous individual monitoring can reduce treatment costs, improve clinical outcomes, and decrease disease progression rate in CF patients. The disclosed methods may be used to predict or identify individuals most likely to benefit from various interventions allowing for a proactive (vs. the current reactive) approach in managing pulmonary exacerbations for patients with CF.

Spirometry is the primary tool used to assess lung function in diseases, including asthma, chronic obstructive pulmonary disease, and CF. It has been central to defining the natural history of these disorders and in developing algorithms to predict their trajectories. (23) Spirometric measures (e.g., $FEV_1$) are the standard-of-care used to assess disease progression and the most common endpoints in clinical trials for lung disease. (25) However, they are insensitive to the cellular and molecular processes that drive lung disease.

While spirometry, primarily $FEV_1$, is the standard clinical measure of lung function and is used ubiquitously to monitor disease progression and therapy response in CF, measures are abnormally low in virtually all adult CF patients, but young patients usually display normal $FEV_1$. However, structural abnormalities, including bronchiectasis, are observed via computed tomography (CT) in up to ⅓ of CF patients before the $3^{rd}$ year of life. (8). Similarly, bronchoalveolar lavage (BAL) has shown that infection and inflammation can be present years prior to clinical symptoms and spirometric changes. These observations indicate that common clinical metrics (e.g., body mass index and $FEV_f$) are trailing indicators of disease progression and represent the culmination of years of pathological changes at the structural and molecular levels (10, 11). As such, they typically cannot be used to identify young patients at risk for rapid lung function decline or patients for whom interventions could prevent permanent lung disease from becoming established.

More sensitive clinical tools available to assess lung disease are also ill-suited for prospective monitoring in early CF. For example, BAL fluid is obtained via bronchoscopy, which is invasive and often requires sedation-particularly in pediatric subjects. As such, it cannot be used for intensive monitoring. Similarly, exposure to the ionizing radiation of CT is associated with increased risk of cancer in pediatric subjects, because children are more susceptible to radiation and have longer remaining lifespans than adults 12), making CT also ill-suited for frequent prospective monitoring in CF.

The duration of this spirometric "silent period" in CF lung disease is likely to increase in the coming years, further in view of the recently-approved triple-combination CFTR modulator therapy (Trikafta®, a combination of three drugs—elexacaftor/ivacaftor/tezacaftor—that target the defective CFTR protein). When treated with highly effective modulator therapy, CF patients display initially improved lung function and slower rates of decline, as assessed by $FEV_1$ (11). However, structural remodeling—in particular bronchiectasis—continues in these patients (13). Thus, the CF field is at a crossroads, where dramatic past improvements in care now limit the ability to assess early disease severity and predict disease progression. This is particularly true in young patients for whom effective interventions will yield the greatest improvements in outcomes and generate the largest increases in lifespan. As such, it is advantageous to provide sensitive methods to quantify disease progression and therapy response in the context of spirometrically normal lung function, which may further be non-invasive and radiation-free. Without such tools, further improvements in CF care and increases in CF patient longevity may be limited. The present disclosure seeks to address this gap with methods that may be used to monitor and predict lung function decline and structural remodeling in early CF.

The disclosed methods, in one aspect, may be used to fill this void by combining structural and functional lung measurements that may be used to detect, monitor, or predict lung pathophysiologies. Exemplary methods useful for determining a structural or functional lung measurement include, but are not limited to, MRI, CT, or other imaging methods known in the art, which may be combined with FD analysis, and methods for protein biomarker measurement including, not limited to, LC-MS/MS (Liquid Chromatography incorporated with tandem Mass Spectrometry) and ELISA. In one exemplary embodiment, that reflect the mechanisms driving lung function decline and remodeling in CF. Previously, bronchiectasis markers (29-30) examined in a biased fashion, focused only on targeted proteins in blood using epitope-based analyses with aptamers, which are prone to false positives and negatives. These factors contributed to only modest correlations (r ~0.45) and did not further the understanding of CF bronchiectasis from what was known from other lung diseases. In contrast, Applicant has identified markers that correlate with disease severity (mean r ~0.72) during stable disease, improving the ability to forecast lung function decline (FIG. 4).

Figure 14:
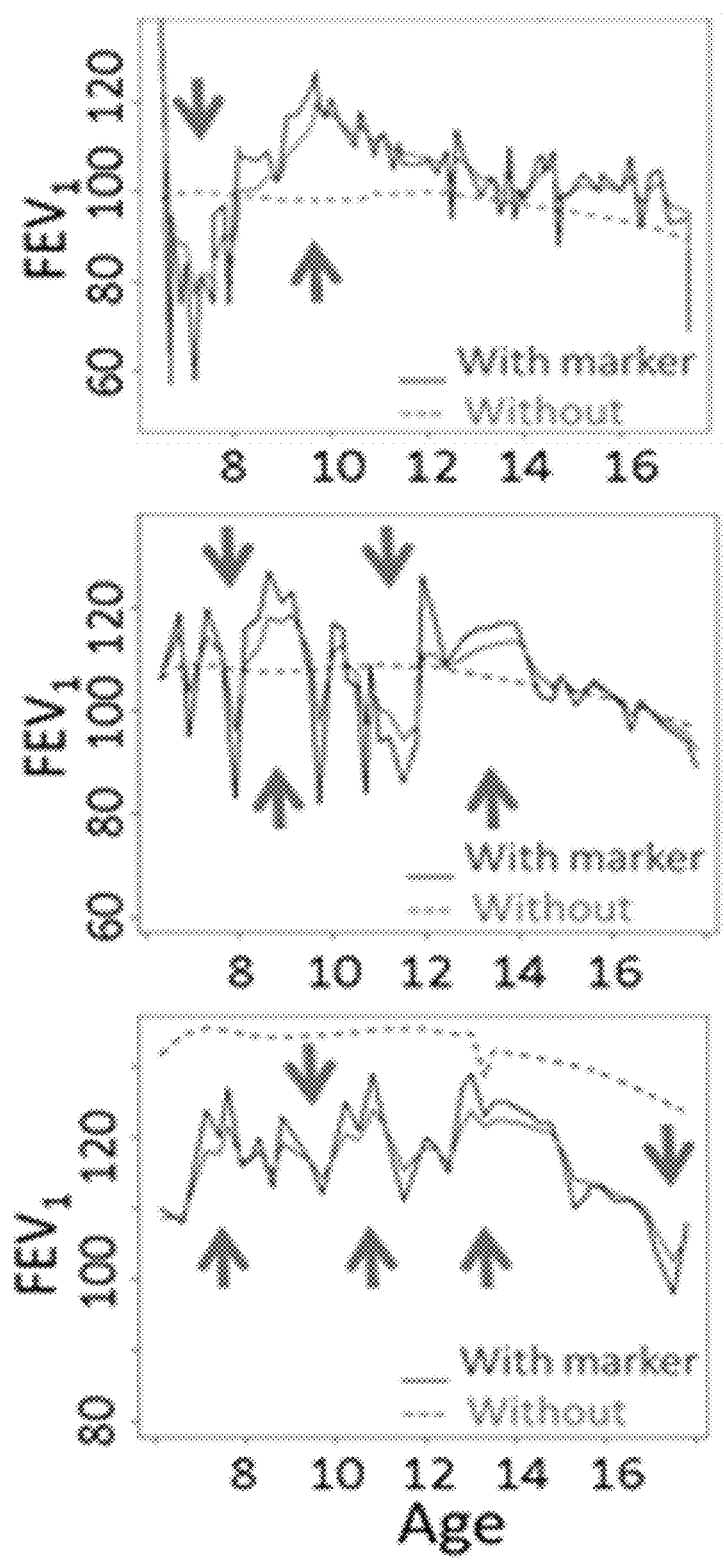
FIG. 14. Lung function prediction with biomarkers. $FEV_1$ trajectory is predicted for three CF patients with proteomic biomarker data from 87 subjects. Clinical data is shown in (black), while the algorithm's prediction is shown without (dashed) or with (solid) or 3 of the top 20 markers (coded to maintain blind during ongoing studies to develop the algorithm for clinical translation). Arrows demonstrate increased accuracy for predicting lung function, especially for upward or downward deflections from the smoothed trajectory. Adding markers to the model significantly improved personalized prediction of lung function trajectories, demonstrating compelling evidence that the disclosed approach can translate into a superior tool for CF.

LC-MS/MS discovery of systemic disease biomarkers and FD analysis: Based on cancer and cardiovascular research, where conventional "shotgun" proteomics identify 500-1000 proteins per sample but failed to distinguish disease severity cohorts, Applicant reasoned that deeper proteomic screening would be necessary for CF studies. Thus, Applicant developed a pipeline using multidimensional protein separation by abundant protein-adsorption columns and gel and column chromatography. This more rigorous approach generated multiple fractions from each sample for subsequent MS analysis (7-17). Cohorts of 44 mild ($FEV_1$>85%) and 44 severe (<$45^{th}$ percentile) CF patient were matched based on age, gender, genotype, and infection status, then randomized and blinded before proteomic analysis. Applicant identified 61,942 protein isoforms expressed in both cohorts, with 19,162 isoforms identified in all subjects. Principal Component Analysis (PCA), logistic regression with Least Absolute Shrinkage and Selection Operator (LASSO) (18), random forests (19), Wilcoxon Rank Sum (44), and McNemar's tests (45) were used to reduce the dataset from ~62,000 isoforms analyzed to 744 isoforms across the battery of five tests. PCA of the top 744 isoforms with respect to $FEV_1$ indicated that these markers segregated mild from severe disease and are good discriminators of lung function in this cross-sectional group. A subset of isoforms were identified by nonbiased proteomic analysis and may be biomarkers of choice for developing a lung function decline prediction model. Building on these approaches, Applicant used FD analysis to characterize lung function at the population level and to accurately predict rapid decline in individual patients. For example, FIG. 14 shows the forecasting performance of the top 3, (voltage gated calcium channel alpha 1F subunit CACNA1F [9606], pleckstrin homology domain-containing family A member 5 isoform X1 PLEKHA5 [9606], and pleckstrin homology domain-containing family A member 5 isoform X9 PLEKHA5 [9606]).

In certain aspects, $FEV_1$ may be used with biostatistical modeling as a point-of-care tool (14). The predictive power may be improved when data from Liquid Chromatography is incorporated with tandem Mass Spectrometry (LC-MS/MS), which can yield proteomic biomarkers sensitive at the molecular level to changes in CF lung disease (FIG. 4, 5). Here, these biostatical and proteomic tools may be combined with one or more biomarkers as disclosed herein, (See Table 4, Panel of protein biomarker covariates for algorithm). Functional information (e.g., as obtained via hyperpolarized (HP)$^{129}$Xe MRI, fluorine MRI, CT, or the like) may be used to determine regional lung dysfunction longitudinally and ultra-short echo-time (UTE), and may further be used to detect structural remodeling over time.

TABLE 4

Panel of protein biomarker covariates
Protein name (gene name)

1. alpha 1 type XXIV collagen precursor
2. alpha-2-macroglobulin
3. alpha-fetoprotein enhancer binding protein
4. Alstrom syndrome protein 1 isoform 1
5. aminopeptidase O isoform X9 (C9orf3)

TABLE 4-continued

Panel of protein biomarker covariates
Protein name (gene name)

6. ankyrin-3 isoform 3
7. anti-HBsAg immunoglobulin Fab kappa chain, partial
8. anti TNF-alpha antibody light-chain Fab fragment, partial
9. ARAP2 protein (ARAP2)
10. Bifunctional glutamate/proline—tRNA ligase (EPRS)
11. C10ORF6
12. CECR2 protein (CECR2)
13. cell division cycle 2-like 5 (cholinesterase-related cell division controller) (CDC2L5)
14. chromodomain-helicase-DNA-binding protein 6 isoform X3 (CHD6)
15. chromosome 3 open reading frame 15 (C3orf15)
16. cilia- and flagella-associated protein 91 isoform 3
17. cingulin-like 1 (CGNL1)
18. CLIP-associating protein 2 isoform X24 (CLASP2)
19. Coiled-coil domain-containing protein 18
20. coiled-coil domain-containing protein 18 isoform X2 (CCDC18)
21. coiled-coil domain-containing protein 93 isoform X3 (CCDC93)
22. collagen triple helix repeat-containing RP11-45B20.2
23. collagen, type XXIV, alpha 1 (COL24A1)
24. complement component C2 (C2)
25. complement component C6 isoform X7 (C6)
26. complement factor H (CFH)
27. Connector enhancer of kinase suppressor of ras
28. connector enhancer of kinase suppressor of ras 2 isoform X2 (CNKSR2)
29. CTP:phosphocholine cytidylyltransferase
30. death inducer-obliterator-3 (DIDO3)
31. diacylglycerol kinase iota isoform X4 (DGKI)
32. DNA annealing helicase and endonuclease ZRANB3 (ZRANB3)
33. DNA methyltransferase 1-associated protein 1
34. DNAH10 variant protein
35. E3 ubiquitin-protein ligase MIB2 isoform X5 (MIB2)
36. EPRSN1
37. fibrinogen alpha chain preproprotein, isoform alpha (FGA)
38. filamin 2 (FLN2)
39. Fras1-related extracellular matrix protein 2 (FREM2)
40. FYVE, RhoGEF and PH domain-containing protein 5 isoform X2 (FGD5)
41. Gelsolin
42. gelsolin isoform X3 (GSN)
43. glutamate receptor-interacting protein 1 isoform X7 (GRIP1)
44. growth-inhibiting protein 24 (GIG24)
45. hCG1656772
46. hemicentin
47. Histidine-rich glycoprotein
48. histidine-rich glycoprotein isoform X1 (HRG)
49. histone acetyltransferase MORF alpha
50. IF2 protein (IF2)
51. immunoglobulin lambda light chain VLJ region (IGL)
52. interferon regulatory factor-2 binding protein 2B
53. junction-mediating and -regulatory protein isoform X2 (JMY)
54. KIAA0328 protein KIAA0328
55. kinesin-like protein (KIF2)
56. kinesin-like protein KIF21A isoform X7 (KIF21A)
57. laminin subunit alpha-2 isoform X3 (LAMA2)
58. la-related protein 1 isoform X5 LARP1
59. LIM and calponin homology domains-containing protein 1 isoform X20 (LIMCH1)
60. LIM and calponin homology domains-containing protein 1 isoform X22 (LIMCH1)
61. lysine-specific demethylase 2B isoform X7 (KDM2B)
62. MAX gene-associated protein isoform X11 (MGA)
63. multiple endocrine neoplasia type 1 candidate protein number 18 (HSPF2)
64. MYCBP-associated protein isoform X1 (MYCBPAP)
65. nebulin-related anchoring protein, isoform CRA_b
66. Non-canonical poly(A) RNA polymerase PAPD5 (PAPD5)
67. PAP associated domain containing protein 5 variant
68. partitioning-defective 3-like protein splice variant c (PAR3L)
69. paraoxanase-3
70. PF6
71. Platelet glycoprotein 1b alpha chain (GP1BA)
72. Pleckstrin homology-like domain family B member 2 (PHLDB2)
73. PMFBP1 protein (PMFBP1)
74. poly (ADP-ribose) glycohydrolase (PARG)
75. PRO2841
76. Pregnancy zone protein
77. probable E3 ubiquitin-protein ligase HERC1 isoform X1 (HERC1)
78. probable E3 ubiquitin-protein ligase HERC1 isoform X11 (HERC1)
79. Protein AMBP (AMBP)
80. protein arginine N-methyltransferase 3 isoform X1 (PRMT3)
81. Protein SCAF11 (SCAF11)
82. ral GTPase-activating protein subunit alpha-1 isoform X12 (RALGAPA1)

TABLE 4-continued

Panel of protein biomarker covariates
Protein name (gene name)

83. Receptor-type tyrosine-protein phosphatase C (PTPRC)
84. RGS3 isoform C2PA-RGS3 (RGS3)
85. Rho-GTPase activating protein 10 (ARHGAP10)
86. RNA-binding motif protein, Y chromosome, family 1 member B isoform X1 (RBMY1B)
87. RUNDC1 protein (RUNDC1)
88. protein-methionine sulfoxide oxidase MICAL3 isoform X10 (MICAL3)
89. Protein phosphatase 1 regulatory subunit (PPP1R12B)
90. Protein sidekick-2 (SDK2)
91. sacsin isoform X3 (SACS)
92. SAPS domain family, member 2 (SAPS2)
93. serine/threonine-protein phosphatase 4 regulatory subunit 3A isoform 1
94. serine-protein kinase ATM isoform X5 (ATM)
95. serum aryldialkylphosphatase precursor
96. SHMT2 protein (SHMT2)
97. smoothelin-B3 (SMTN)
98. somatostatin receptor interacting protein splice variant a (SSTRIP)
99. sperm-associated antigen 17 isoform X3 (SPAG17)
100. spermatogenesis-associated protein 31C1 isoform X1 (SPATA31C1)
101. synaptotagmin-like protein 2 isoform X10 (SYTL2)
102. T-cell lymphoma invasion and metastasis 1 (TIAM1)
103. translation initiation factor (IF2)
104. transthyretin precursor
105. terminal nucleotidyltransferase 4B isoform b
106. tetratricopeptide repeat protein 21A isoform X6 (TTC21A)
107. thrombospondin 1 (THBS1)
108. triadin isoform X17 (TRDN)
109. ubiquitin carboxyl-terminal hydrolase 40 isoform X1 (USP40)
110. uridine-cytidine kinase-like 1 isoform 2
111. uridine-cytidine kinase-like 1 isoform X7 (UCKL1)
112. utrophin isoform X4 (UTRN)
113. Voltage-dependent N-type calcium channel subunit alpha-1B (CACNA1B)
114. WD repeat-containing protein 64 isoform X2 (WDR64)
115. zinc finger and AT hook domain containing (ZFAT)
116. Zinc finger homeobox protein 4 (ZFHX4)

For predictive modeling, the primary outcome-lung function—may be defined by the ventilation defect percent (VDP) or other regional measures (partial ventilation, ventilation heterogeneity, hyper-intensity, etc.). The FD model (46) may be used to analyze longitudinal VDP as a function of time (indexed as age at the time of functional assessment, via MRI scan, CT, or the like, and blood draw) and degree of proteomic expression with adjustment for select clinical/demographic characteristics as covariates, including lung clearance index (LCI). Applicant has built a prediction model using patient-specific information to predict the onset of rapid decline. For VDP, this model can be expressed as Equation 9:

$$VDP_{ij}=\mu_i+W_i(t_{ij})+Z_i; \mu_i(t_{ij})=f(t_{ij})+X_{ik}\theta_k, \quad \text{(Equation 9)}$$

where $VDP_{ij}$ is the ventilation metric for the $i^{th}$ patient at time point $t_{ij}$ (age in years). The function $\mu_i(t_{ij})$ is mean VDP evolution for the $i^{th}$ patient, which includes spline formulation $f(t_{ij})$ to characterize overall VDP progression as FD and encompasses covariates $X_{i1}, \ldots X_{ip}$, with corresponding association parameters $\theta_{i1}, \ldots \theta_{ip}$. The term $U_i$, is assumed to follow a normal distribution with mean 0 and variance)$^2$, and provides patient-specific variability. $W_i(t_{ij})$ is a stochastic process reflecting image variation over time in an individual patient. Integrated Brownian motion is used to depict this process, which has variance $\sigma^2$. $Z_i$ represents normally distributed measurement error with mean 0 and variance $\tau^2$. The covariance functions and estimation algorithm have been described previously (47). Predictive models for other regional lung function metrics can be constructed similarly. The model for the CFF-PR was implemented using the lmenssp package (48) in R (R Foundation for Statistical Computing, Vienna, Austria). Candidate molecular markers $B_{i1}, \ldots, B_{im}$ may be used as covariates (main effect and interaction effect with time), and denote the association parameters as $\gamma_1, \ldots, \gamma_m$ to fit the model on smaller data.

When using structural remodeling as a covariable, which may include data obtained via any imaging method known in the art, including, but not limited to, CT, MRI, or other image analysis technique, prediction modeling and evaluation may be used, except the discreet response variable will be log-transformed and expressed as Equation 10:

$$\log(UTEbronch_{ij})=\mu_i(t_{ij})+U_i+W_i(t_{ij})+Z_i, \quad \text{(Equation 10)}$$

One outcome, for example, the degree of bronchiectasis, can be defined be expert reader scoring or using automated software (e.g., deep learning algorithms), may use scores from FPCA to estimate correlation between proteomic expression and degree of bronchiectasis (49).

Figure 18:
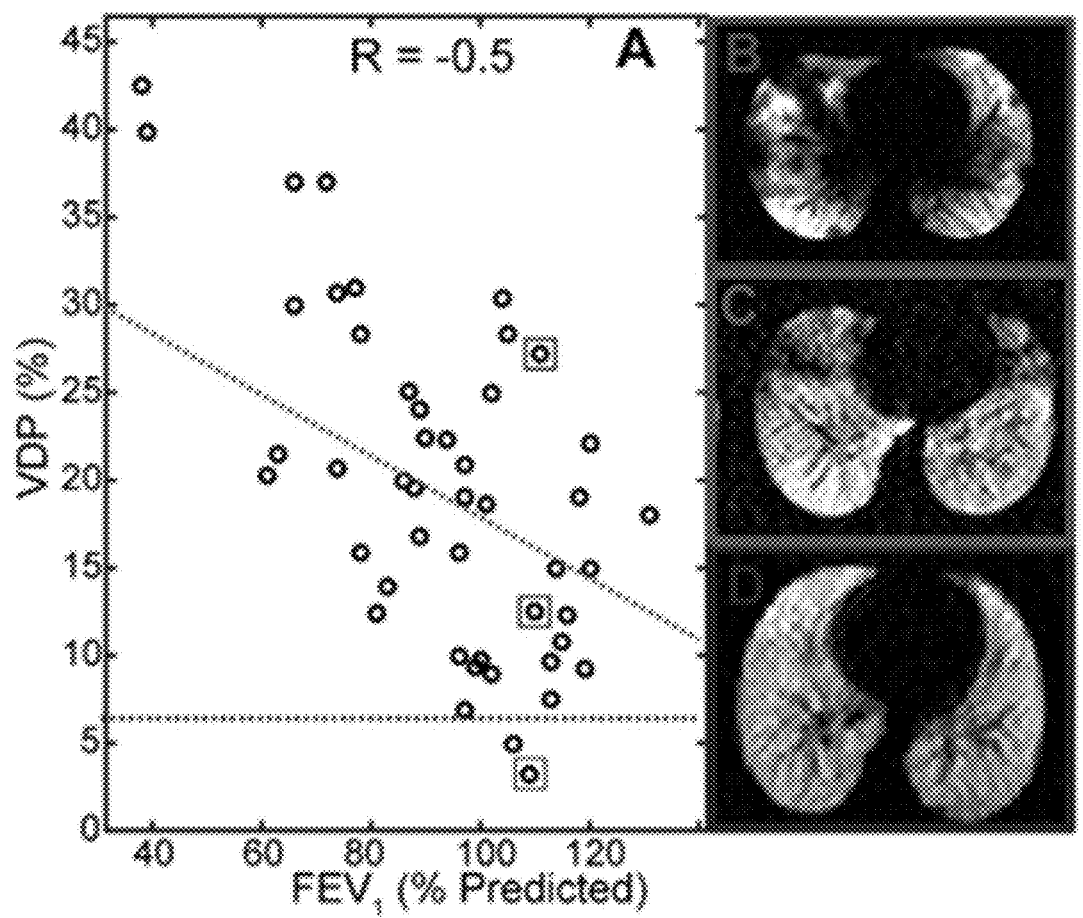
FIG. 18. $^{129}Xe$ MRI of lung dysfunction. A) $^{129}Xe$ VDP vs $FEV_1$ in CF patients. Mean VPD of controls is shown (blue line). While $FEV_1$ and VDP correlate (red line, p=<0.001), scatter is seen in CF patients with normal $FEV_1$. B-D) Ventilation images of CF patients with $FEV_1>100\%$. These patients display different regional ventilation, ranging from normal (D, VDP<4%) to impaired (B, VDP=28%), indicating the higher sensitivity of $^{129}Xe$ MRI.

Sensitivity of MRI/CT to early CF lung disease: The disclosed modeling may be applied to advanced lung imaging data, which can be performed in children too young to perform spirometry (50) and detect pathology prior to spirometric changes (FIG. 18). Any acquisition strategy can be used. For example, in one approach an efficient 3D spiral, FLORET (51-55) sequence to depict ventilation at 3-mm resolution may be used the highest $^{129}$Xe resolution achieved in humans. "Keyhole" reconstruction pipeline may be used to mitigate regional $^{129}$Xe signal decay and improve image accuracy (56). Biomarkers of structural remodeling using a $^1$H FLORET acquisition may be optimized to visualize airway abnormalities. This free-breathing protocol generates images with 1-mm resolution in ~5 minutes (57, 58). Airway-optimized $^1$H FLORET may be used to guide clinical bronchoscopies to obtain bronchoalveolar lavage (BAL) fluid from specific lung pathologies, including bronchiectasis. Using these data and FD analysis, molecular changes may be used to forecast functional and structural disease in individual CF patients. These methods may combine innovations in proteomics, imaging and modeling to 1) enable translational research that continues to advance CF patient care and 2) define the post-CFTR-modulator "new normal" for the natural history of CF. While the markers identified in this work may be specific to CF, combining non-invasive HP $^{129}$Xe and UTE MRI with blood and BAL proteomics may be applicable to a wide range of lung diseases.

Functional Data (FD) and Functional Principal Component (FPC) analyses: The disclosed methods build on FD analysis and longitudinal models using $FEV_i$ data from the CFF-PR. This modeling blends established biostatistical approaches with modern FD analyses to characterize the nonlinear $FEV_1$ trajectory of individual patients and predicts subsequent decline. The predictive models may be used for in-clinic applications for decision aids for treatment planning and at the time of patient encounters. Furthermore, predictive accuracy of lung function decline improves with proteomic markers (FIG. 14). Biomarker data correlation with $FEV_1$ may be measured in multiple simulations and by appropriate statistical tests as described.

Hyperpolarized (HP)$^{129}$Xe MRI: Images from 50 CF patients (24 male, 26 female) were acquired. HP $^{129}$Xe polarization (~20-40%) was measured before MRI with a polarimetry station. Images were acquired with $^{129}$Xe coils to provide comparable performance across the range of subject sizes (15). Single-breath HP$^{129}$Xe images were acquired using a multi-slice gradient-echo sequence, linear phase encoding, and optimized flip angle (16). Impaired ventilation was assessed using the Ventilation Defect Percentage (VPD), defined by employing automated software to identify lung voxels with signal intensities below a threshold that maximized contrast between age-matched, healthy control subjects and CF patients (17).

Figure 15:
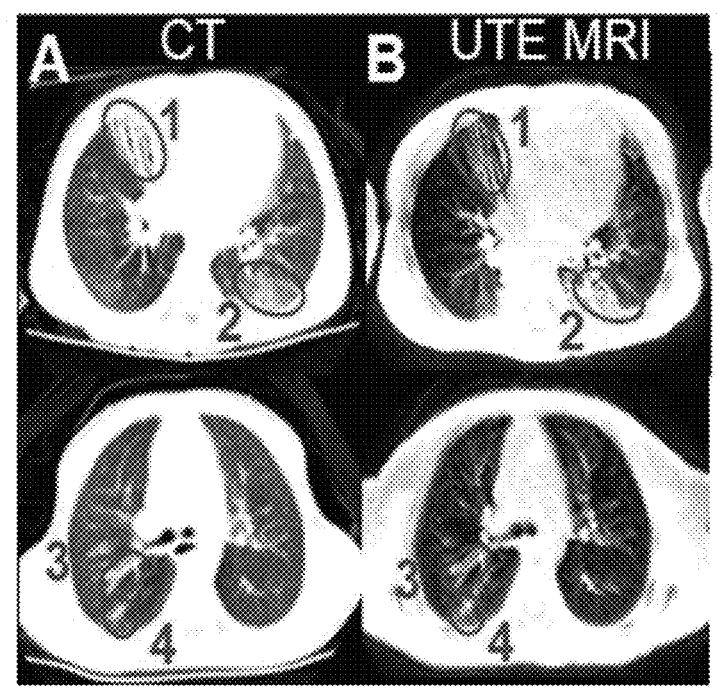
FIG. 15. CF pathologies (rd circles) on CT (A) and ultra-short echo-time (UTE) magnetic resonance imaging (MRI) (B) in 1-yr old patients: (1) bronchiectasis, (2) ground glass opacity, (3) wall thickening, and (4) mucus plugging. (C) "Brody" scoring for both modalities.
Figure 15:
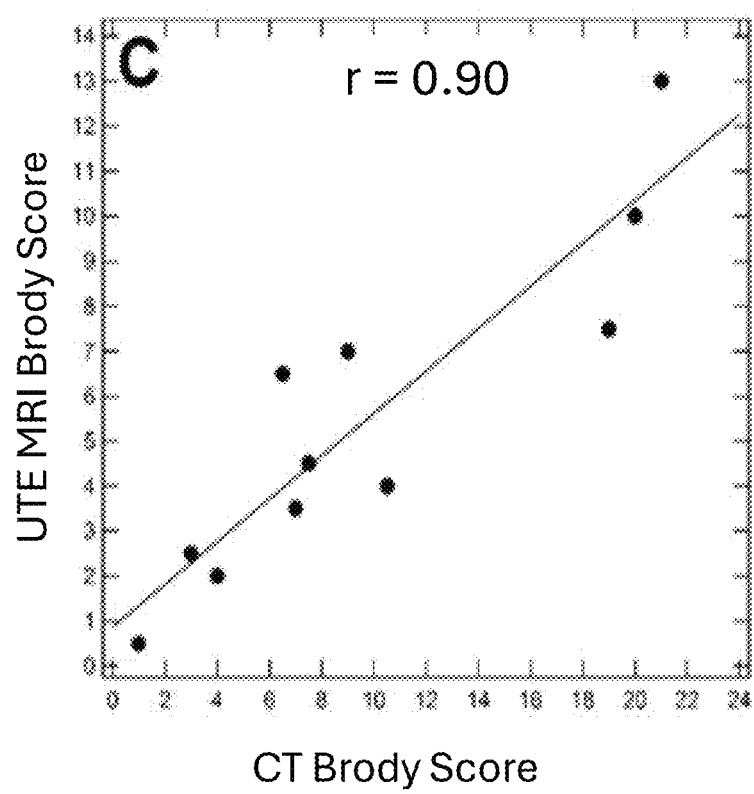

UTE MRI: Historically, lung MRI has been challenging, because magnetic inhomogeneities are created by air-tissue interfaces (i.e., alveoli) and cause the MR signal to decay with a rate constant ($T_2$*) of ~0.8 ms at 3 T (18). Rapid decay was mitigated using an ultra-short echo-time (UTE) sequence to sample the MR signal before significant decay (echo-times of <200 μs), retaining ~80% of parenchymal signal. Data were collected at end expiration, where $T_2$* and motion are minimized (19). Structural pathology (wall thickening, bronchiectasis, etc.) was identified and scored by two board-certified, pediatric radiologists using an MRI-variant of the well-established "Brody" scoring system (20) (FIG. 15).

Correlation of MRI and Proteomics: $^{129}$Xe MRI and same-day blood draws were performed in 9 CF patients with mild lung disease ($FEV_1$>85%). Blood samples were grouped by functional impairment according to ventilation defect percentage (VDP) as no impairment (VPD <2, 2 male, 1 female), mild (5<VDP<15; 1 m, 2 f), and moderate (VDP >20, 2 m, 1 f). UTE MRI and same-day blood draws were performed in 8 CF patients with mild disease. Bronchiectasis was scored with a simplified system by dividing lungs into 6 regions (5 lobes plus lingula) (20, 21). Regions were scored independently by a trained reader (scale: 0-3; 0=not present; 1=present in <⅓ lobe; 2=present in <⅔ lobe; and 3=present in >⅔ lobe), and regional scores were summed to yield whole-lung scores. Samples were grouped by bronchiectasis severity as mild (score<3; 2 m, 2 f) or moderate (4 score <10; 2 m, 2 f). For both UTE and VDP, group identities were blinded for non-biased proteomic analysis.

Correlation of MRI and Proteomics: For functional MRI studies, $^{129}$Xe MRI and same-day blood draws were performed in 9 CF patients with mild lung disease ($FEV_1$>85%). Blood samples were grouped by functional impairment as no impairment (VPD<2, 2 male, 1 female), mild (5<VDP<15; 1 m, 2 f), and moderate (VDP>20, 2 m, 1 f). UTE MRI and same-day blood draws were performed in 8 CF patients with mild disease. For structural studies, bronchiectasis was scored with a simplified system by dividing lungs into 6 regions (5 lobes plus lingula) (21, 22). Regions were scored independently by a trained reader (scale: 0-3; 0=not present; 1=present in <⅓ lobe; 2=present in <⅔ lobe; and 3=present in >⅔ lobe), and regional scores were summed to yield whole-lung scores. Samples were grouped by bronchiectasis severity as mild (score<3; 2 m, 2 f) or moderate (4 score 10; 2 m, 2 f). For both UTE and VDP, group identities were blinded for non-biased proteomic analysis.

Figure 16:
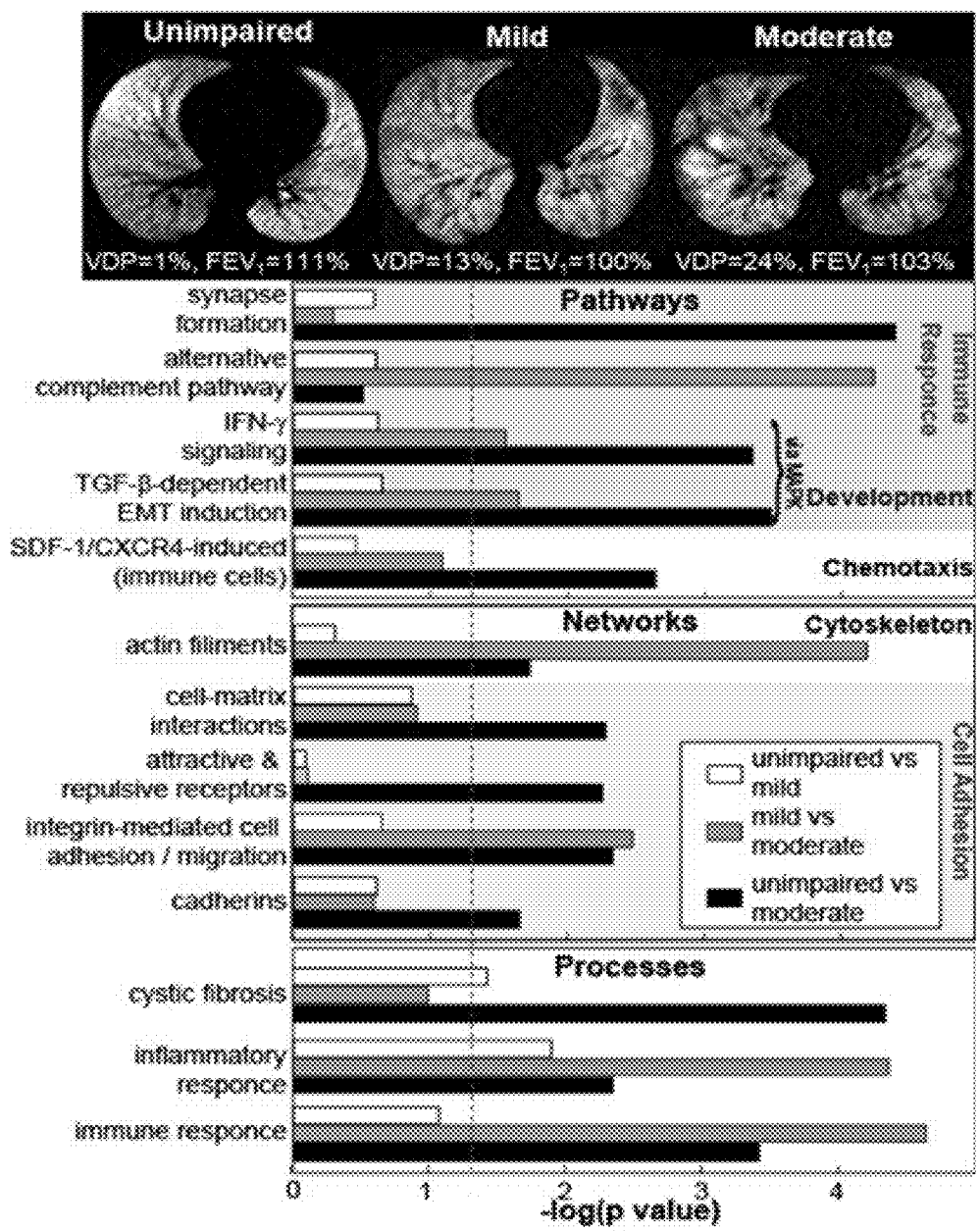
FIG. 16. Ventilation vs. proteomics. Top) CF patients with $FEV_1>100\%$ and no, mild, and moderate ventilation impairment via $^{129}Xe$ MRI. Bottom) Proteomic differences in CF patient plasma collected on the day of MRI. Cohort Comparisons are indicted in the legend (center). Vertical line: p=0.05.
Figure 17:
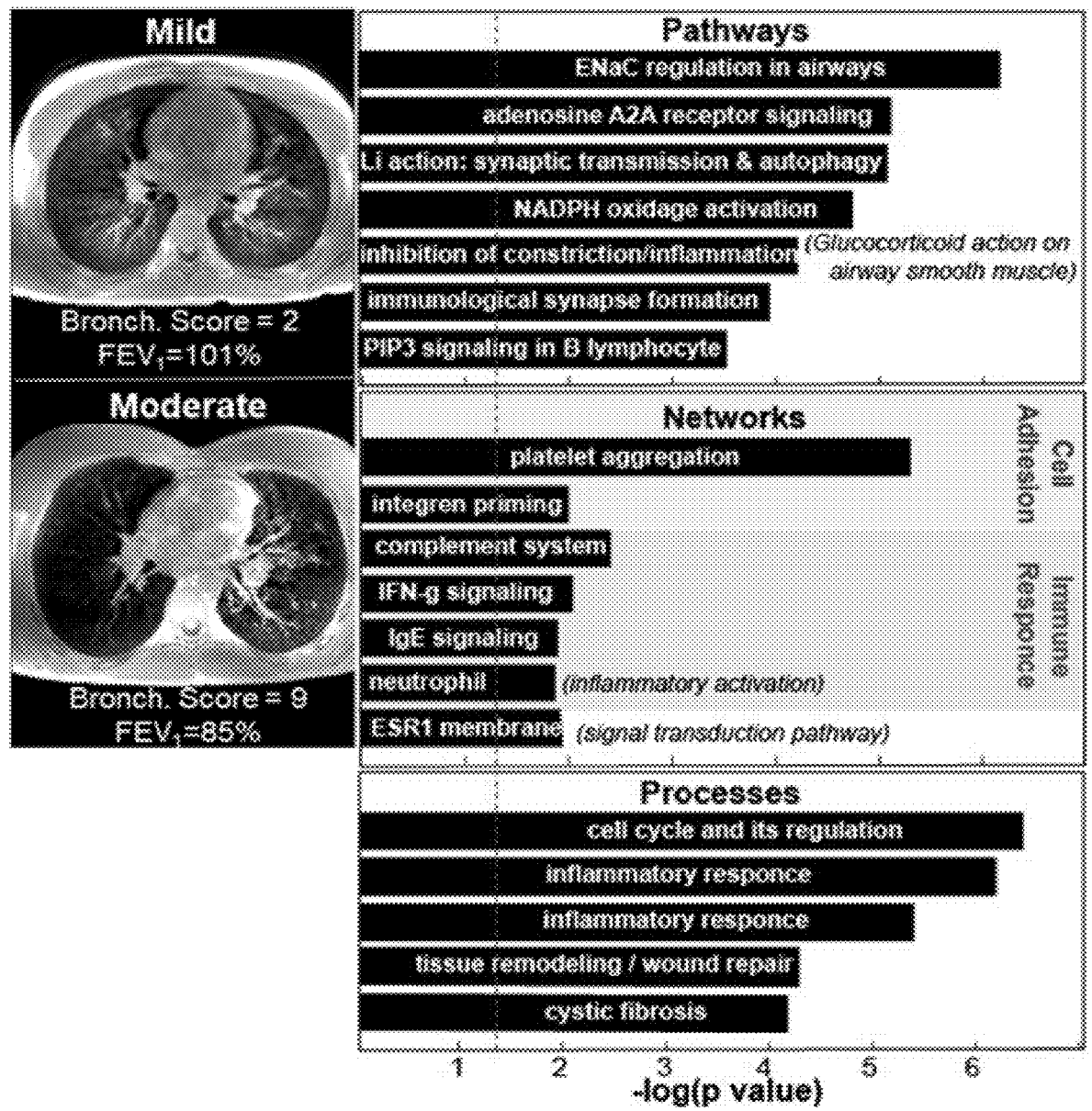
FIG. 17. Structural UTE MRI vs. proteomics. Left) CF patients with mild (top) and moderate (bottom) remodeling via UTE. Right) Proteomic differences between patients with mild and moderate remodeling. Vertical line: p=0.05.

Using pathway, network, and process analyses, Applicant successfully identified the no, mild, or moderate impairment groups before data were unblinded. Analysis of proteomic changes revealed differences in pro-inflammatory signaling, remodeling-associated cytoskeletal rearrangement, and cell adhesion associated with inflammatory cell activation (FIG. 16). Analysis of the groups segregated by structural Ultra-Short Echo Time (UTE) MRI revealed changes in pathways associated with CF disease (e.g. ENAC regulation), inflammatory signaling, remodeling, and cell adhesion (FIG. 17). The no, mild, or moderate impairment groups were successfully identified by Applicant before data were unblinded. Of particular note—all subjects had 85% or higher $FEV_1$ percent predicted. Current pulmonary function tests cannot distinguish impairment in patients with 85% or higher $FEV_1$ percent predicted. Analysis of proteomic changes revealed differences in pro-inflammatory signaling, remodeling-associated cytoskeletal rearrangement, and cell adhesion associated with inflammatory cell activation (FIG. 16). Analysis of the groups segregated by structural Ultra-Short Echo Time (UTE) MRI revealed changes in pathways associated with CF disease (e.g. epithelial sodium channel (ENAC) regulation), inflammatory signaling, remodeling, and cell adhesion (FIG. 17). These blinded studies provide compelling evidence that proteomics detects mild structural and ventilation abnormalities identified by MRI, supporting Applicant's hypothesis that these technologies yield robust and complimentary information to detect early remodeling and lung function impairment. Significantly, this sensitivity to early disease cannot be validated with available lung function testing.

REFERENCES

1. Drumm M L, Ziady A G, Davis P B. Genetic variation and clinical heterogeneity in cystic fibrosis. Annu Rev Pathol. 2012; 7:267-82. doi: 10.1146/annurev-pathol-011811-120900 [doi].
2. Rosenfeld M, VanDevanter D R, Ren C L, Elkin E P, Pasta D J, Konstan M W, Morgan W J, Fibrosis IoCotESoC. Decline in lung function does not predict future decline in lung function in cystic fibrosis patients. Pediatr Pulmonol. 2015; 50(9):856-62. doi: 10.1002/ppul.23227 [doi].
3. Szczesniak R D, McPhail G L, Li D, Amin R S, Clancy J P. Predicting future lung function decline in cystic fibrosis patients: Statistical methods and clinical connections. Pediatr Pulmonol. 2016; 51(2):217-8. doi: 10.1002/ppul.23357 [doi].
4. Accurso F J, Rowe S M, Clancy J P, Boyle M P, Dunitz J M, Durie P R, Sagel S D, Hornick D B, Konstan M W, Donaldson S H, Moss R B, Pilewski J M, Rubenstein R C, Uluer A Z, Aitken M L, Freedman S D, Rose L M, Mayer-Hamblett N, Dong Q, Zha J, Stone A J, Olson E R, Ordonez C L, Campbell P W, Ashlock M A, Ramsey B W. Effect of VX-770 in persons with cystic fibrosis and the G551D-CFTR mutation. N Engl J Med. 2010; 363(21): 1991-2003.
5. Wainwright C E, Elborn J S, Ramsey B W, Marigowda G, Huang X, Cipolli M, Colombo C, Davies J C, De B K, Flume P A, Konstan M W, McColley S A, McCoy K, McKone E F, Munck A, Ratjen F, Rowe S M, Waltz D, Boyle M P, Group T S, Group T S. Lumacaftor-Ivacaftor in Patients with Cystic Fibrosis Homozygous for Phe508del CFTR. N Engl J Med. 2015; 373(3):220-31. doi: 10.1056/NEJMoa1409547 [doi].
6. Hoy S M. Elexacaftor/Ivacaftor/Tezacaftor: First Approval. Drugs. 2019; 79(18):2001-7. Epub 2019/12/01. doi: 10.1007/s40265-019-01233-7. PubMed PMID: 31784874.
7. Sanders D B, Bittner R C, Rosenfeld M, Hoffman L R, Redding G J, Goss C H. Failure to recover to baseline pulmonary function after cystic fibrosis pulmonary exacerbation. Am J Respir Crit Care Med. 2010; 182(5):627-32. doi: 200909-1421OC [pii]; 10.1164/rccm.200909-1421OC [doi].
8. Roach D J, Cremillieux Y, Fleck R J, Brody A S, Serai S D, Szczesniak R D, Kerlakian S, Clancy J P, Woods J C. Ultrashort Echo-Time Magnetic Resonance Imaging Is a Sensitive Method for the Evaluation of Early Cystic Fibrosis Lung Disease. Ann Am Thorac Soc. 2016; 13(11):1923-31. PubMed PMID: WOS: 000419097900012.
9. Tepper L A, Caudri D, Rovira A P, Tiddens H A, de Bruijne M. The development of bronchiectasis on chest computed tomography in children with cystic fibrosis: can pre-stages be identified?Eur Radiol. 2016; 26(12):4563-9. Epub 2016/04/25. doi: 10.1007/s00330-016-4329-z. PubMed PMID: 27108295; PMCID: PMC5101271.
10. Konstan M W, McKone E F, Moss R B, Marigowda G, Tian S, Waltz D, Huang X, Lubarsky B, Rubin J, Millar S J, Pasta D J, Mayer-Hamblett N, Goss C H, Morgan W, Sawicki G S. Assessment of safety and efficacy of long-term treatment with combination lumacaftor and ivacaftor therapy in patients with cystic fibrosis homozygous for the F508del-CFTR mutation (PROGRESS): a phase 3, extension study. Lancet Respir Med. 2017; 5(2):107-18. doi: S2213-2600(16)30427-1 [pii]; 10.1016/S2213-2600 (16)30427-1 [doi].
11. Sawicki G S, McKone E F, Pasta D J, Millar S J, Wagener J S, Johnson C A, Konstan M W. Sustained Benefit from Ivacaftor Demonstrated by Combining Clinical Trial and Cystic Fibrosis Patient Registry Data. Am J Respir Crit Care Med. 2015; 192(7):836-42. doi: 10.1164/rccm.201503-0578OC [doi].
12. Pearce M S, Salotti J A, Little M P, McHugh K, Lee C, Kim K P, Howe N L, Ronckers C M, Rajaraman P, Craft A W, Parker L, de Gonzalez A B. Radiation exposure from CT scans in childhood and subsequent risk of leukaemia and brain tumours: a retrospective cohort study. Lancet. 2012; 380(9840):499-505. doi: 10.1016/S0140-6736(12) 60815-0. PubMed PMID: WOS:000307109000031.
13. Chassagnon G, Hubert D, Fajac I, Burgel P-R, Revel M-P. Long-term computed tomographic changes in cystic fibrosis patients treated with ivacaftor. European Respiratory Journal. 2016; 48(1):249-52. doi: 10.1183/13993003.01918-2015.
14. Szczesniak R D, Brokamp C, Su W, Mcphail G L, Pestian J, Clancy J P. Improving Detection of Rapid Cystic Fibrosis Disease Progression-Early Translation of a Predictive Algorithm Into a Point-of-Care Tool. IEEE Journal of Translational Engineering in Health and Medicine. 2019; 7:1-8. doi: 10.1109/JTEHM.2018.2878534.
15. Loew W T R, Pratt R, Cleveland Z, Dumoulin C, Woods J, Giaquinto R. A Volume saddle coil for hyperpolarized 129Xe lung imaging. Proc Int Soc Magn Reson Med. 2015; 2015:93.
16. Miller G W, Altes T A, Brookeman J R, De Lange E E, Mugler J P, 3rd. Hyperpolarized 3He lung ventilation imaging with B1-inhomogeneity correction in a single breath-hold scan. Magma. 2004; 16(5):218-26. doi: 10.1007/s10334-003-0028-2. PubMed PMID: 15108030.
17. Thomen R P, Walkup L L, Roach D J, Cleveland Z I, Clancy J P, Woods J C. Hyperpolarized 129Xe for investigation of mild cystic fibrosis lung disease in pediatric patients. Journal of Cystic Fibrosis. 2017; 16(2):275-82. doi: http://dx.doi.org/10.1016/j.jcf.2016.07.008.
18. Yu J, Xue Y, Song H K. Comparison of lung $T2^*$ during free-breathing at 1.5 T and 3.0 T with ultrashort echo time imaging. Magnetic resonance in medicine: official journal of the Society of Magnetic Resonance in Medicine/Society of Magnetic Resonance in Medicine. 2011; 66(1): 248-54. doi: 10.1002/mrm.22829. PubMed PMID: 21695727; PMCID: 3122137.
19. Lederlin M, Cremillieux Y. Three-dimensional assessment of lung tissue density using a clinical ultrashort echo time at 3 tesla: A feasibility study in healthy subjects. Journal of Magnetic Resonance Imaging. 2014; 40(4): 839-47. doi: 10.1002/jmri.24429.
20. Brody A S, Klein J S, Molina P L, Quan J, Bean J A, Wilmott R W. High-resolution computed tomography in young patients with cystic fibrosis: Distribution of abnormalities and correlation with pulmonary function tests. Journal of Pediatrics. 2004; 145(1):32-8. PubMed PMID: WOS:000222738500020.
21. Eichinger M, Optazaite D-E, Kopp-Schneider A, Hintze C, Biederer J, Niemann A, Mall M A, Wielpütz MO, Kauczor H-U, Puderbach M. Morphologic and functional scoring of cystic fibrosis lung disease using MRI. European Journal of Radiology. 2012; 81(6):1321-9. doi: https://doi.org/10.1016/j.ejrad.2011.02.045.
22. Wielpütz MO, Puderbach M, Kopp-Schneider A, Stahl M, Fritzsching E, Sommerburg O, Ley S, Sumkauskaite M, Biederer J, Kauczor H-U, Eichinger M, Mall M A. Magnetic Resonance Imaging Detects Changes in Structure and Perfusion, and Response to Therapy in Early Cystic Fibrosis Lung Disease. American Journal of Respiratory and Critical Care Medicine. 2014; 189(8):956-65. doi: 10.1164/rccm.201309-1659OC. PubMed PMID: 24564281.
23. Szczesniak R, Heltshe S L, Stanojevic S, Mayer-Hamblett N. Use of FEV(1) in cystic fibrosis epidemiologic studies and clinical trials: A statistical perspective for the clinical researcher. Journal of cystic fibrosis: official journal of the European Cystic Fibrosis Society. 2017; 16(3): 318-26. Epub 01/20. doi: 10.1016/j.jcf.2017.01.002. PubMed PMID: 28117136.

24. Vestbo J, Lange P. Natural history of COPD: Focusing on change in $FEV_1$. Respirology. 2016; 21(1):34-43. doi: 10.1111/resp.12589.
25. Hanania N A, Sharafkhaneh A, Celli B, Decramer M, Lystig T, Kesten S, Tashkin D. Acute bronchodilator responsiveness and health outcomes in COPD patients in the UPLIFT trial. Respiratory Research. 2011; 12(1):6. doi: 10.1186/1465-9921-12-6.
26. Stanojevic S, Ratjen F. Physiologic endpoints for clinical studies for cystic fibrosis. Journal of Cystic Fibrosis. 2016; 15(4):416-23. doi: https://doi.org/10.1016/j.jcf.2016.05.014.
27. King T E, Bradford W Z, Castro-Bernardini S, Fagan E A, Glaspole I, Glassberg M K, Gorina E, Hopkins P M, Kardatzke D, Lancaster L, Lederer D J, Nathan S D, Pereira C A, Sahn S A, Sussman R, Swigris J J, Noble P W. A Phase 3 Trial of Pirfenidone in Patients with Idiopathic Pulmonary Fibrosis. New England Journal of Medicine. 2014; 370(22):2083-92. doi: 10.1056/NEJMoa1402582. PubMed PMID: 24836312.
28. Walkup L L, Thomen R P, Akinyi T G, Watters E, Ruppert K, Clancy J P, Woods J C, Cleveland Z I. Feasibility, tolerability and safety of pediatric hyperpolarized Xe-129 magnetic resonance imaging in healthy volunteers and children with cystic fibrosis. Pediatric Radiology. 2016; 46(12):1651-62. PubMed PMID: WOS:000387135600003.
29. DeBoer E M, Kroehl M E, Wagner B D, Accurso F J, Harris J K, Lynch D A, Sagel S D, Deterding R R. Proteomic profiling identifies novel circulating markers associated with bronchiectasis in cystic fibrosis. PROTEOMICS—Clinical Applications. 2017; 11(9-10): 1600147. doi: 10.1002/prca.201600147.
30. DeBoer E M, Wagner B D, Popler J, Harris J K, Zemanick E T, Accurso F J, Sagel S D, Deterding R R. Novel Application of Aptamer Proteomic Analysis in Cystic Fibrosis Bronchoalveolar Lavage Fluid. PROTEOMICS—Clinical Applications.0(0):1800085. doi: 10.1002/prca.201800085.
31. Chen J, Kinter M, Shank S, Cotton C, Kelley T J, Ziady A G. Dysfunction of Nrf-2 in CF epithelia leads to excess intracellular $H_2O_2$ and inflammatory cytokine production. PLoS One. 2008; 3(10):e3367.
32. Ziady A G, Kinter M. Protein sequencing with tandem mass spectrometry. Methods Mol Biol. 2009; 544:325-41.
33. Ziady A G, Sokolow A, Shank S, Corey D, Myers R, Plafker S, Kelley T J. Interaction with CREB binding protein modulates the activities of Nrf2 and NF-kappaB in cystic fibrosis airway epithelial cells. Am J Physiol Lung Cell Mol Physiol. 2012; 302(11):L1221-L31. doi: ajplung.00156.2011 [pii]; 10.1152/ajplung.00156.2011 [doi].
34. Chirkova T, Lin S, Oomens A G, Gaston K A, Boyoglu-Barnum S, Meng J, Stobart C C, Cotton C U, Hartert T V, Moore M L, Ziady A G, Anderson L J. CX3CR1 is an Important Surface Molecule for RSV Infection in Human Airway Epithelial Cells. J Gen Virol. 2015. doi: 10.1099/vir.0.000218 [doi].
35. Sinha C, Zhang W, Moon C S, Actis M, Yarlagadda S, Arora K, Woodroofe K, Clancy J P, Lin S, Ziady A G, Frizzell R, Fujii N, Naren A P. Capturing the Direct Binding of CFTR Correctors to CFTR by Using Click Chemistry. Chembiochem. 2015. doi: 10.1002/cbic.201500123 [doi].
36. Sinha C, Ren A, Arora K, Moon C S, Yarlagadda S, Woodrooffe K, Lin S, Schuetz J D, Ziady A G, Naren A P. PKA and actin play critical roles as downstream effectors in MRP4-mediated regulation of fibroblast migration. Cell Signal. 2015; 27(7):1345-55. doi: S0898-6568(15) 00121-7 [pii]; 10.1016/j.cellsig.2015.03.022 [doi].
37. Ziady A G, Heltshe S L, Kelley T J, Muhlebach M S, Accurso F, Pilewski J, Clancy J P, Sagel S D, Joseloff E. Proteomic analyses of serum from CF patients with mild or severe disease reveal the differential expression of proteins that regulate the differentiation of cartilage, myeloid leukocytes, and intestinal epithelia. Pediatr Pulmonol Suppl. 2014; 38:288.
38. Sagel S D, Wagner B, Ziady A G, Kelley T J, Muhlebach M S, Accurso F, Pilewski J, Heltshe S L, Clancy J P, Joseloff E. Validation of Candidate Serum Protein and Lipid Markers of Disease Severity In CF. Pediatr Pulmonol Suppl. 2014; 38:288.
39. Ziady A G, Lin S, Wyatt C, Clancy J P. Proteomic analyses of BALF reveal potential biomarkers and suggest altered lipid, cyclic nucleotide, and iron metabolism in young CF children versus disease controls. Pediatr Pulmonol Suppl. 2013; 36:250.
40. Li Q, Ding X, Thomas J J, Harding C V, Pecora N D, Ziady A G, Shank S, Boom W H, Lancioni C L, Rojas R E. Rv2468c, a novel Mycobacterium tuberculosis protein that costimulates human CD4+ T cells through VLA-5. J Leukoc Biol. 2012; 91(2):311-20. doi: jlb.0711364 [pii]; 10.1189/jlb.0711364 [doi].
41. Chen X, Shank S, Davis P B, Ziady A G. Nucleolin-mediated cellular trafficking of DNA nanoparticle is lipid raft and microtubule dependent and can be modulated by glucocorticoid. Mol Ther. 2011; 19(1):93-102.
42. Tibshirani R J. Regression shrinkage and selection via the lasso. Royal Statist Soc B. 1996; 58:267-88.
43. Hastie T, Tibshirani R J, Friedman J. The Elements of Statistical Learning: Data Mining, Inference, and Prediction2009 2009.
44. Wilcoxon F. Individual comparisons of grouped data by ranking methods. Journal of economic entomology. 1946; 39:269. Epub 1946/04/01. doi: 10.1093/jee/39.2.269. PubMed PMID: 20983181.
45. Fagerland M W, Lydersen S, Laake P. The McNemar test for binary matched-pairs data: mid-p and asymptotic are better than exact conditional. BMC Med Res Methodol. 2013; 13:91-. doi: 10.1186/1471-2288-13-91. PubMed PMID: 23848987.
46. Szczesniak R D, Su W, Brokamp C, Keogh R H, Pestian J P, Seid M, Diggle P J, Clancy J P. Dynamic predictive probabilities to monitor rapid cystic fibrosis disease progression. Statistics in Medicine. 2020; 39(6):740-56. doi: 10.1002/sim.8443.
47. Diggle P J, Sousa I, Asar 0. Real-time monitoring of progression towards renal failure in primary care patients. Biostatistics. 2015; 16(3):522-36. doi: kxu053 [pii]; 10.1093/biostatistics/kxu053 [doi].
48. Asar 0, Ilk 0. mmm: an R package for analyzing multivariate longitudinal data with multivariate marginal models. Comput Methods Programs Biomed. 2013; 112 (3):649-54. doi: S0169-2607(13)00257-5 [pii]; 10.1016/j.cmpb.2013.07.022 [doi].
49. Szczesniak R D, Li D, Su W, Brokamp C, Pestian J, Seid M, Clancy J P. Phenotypes of Rapid Cystic Fibrosis Lung Disease Progression during Adolescence and Young Adulthood. American Journal of Respiratory and Critical Care Medicine. 2017; 196(4):471-8. doi: 10.1164/rccm.201612-25740C. PubMed PMID: 28410569.
50. Walkup L L, Myers K, El-Bietar J, Nelson A, Willmering M M, Grimley M, Davies S M, Towe C, Woods J C. 129Xe MRI detects ventilation deficits in pediatric stem- 51. Robison R K, Anderson A G, Pipe J G. Three-dimensional ultrashort echo-time imaging using a FLORET trajectory. Magnetic Resonance in Medicine. 2017; 78(3): 1038-49. PubMed PMID: WOS:000407855700022.
52. Zwart N R, Pipe J G. Graphical programming interface: A development environment for MRI methods. Magnetic Resonance in Medicine. 2015; 74(5):1449-60. PubMed PMID: WOS:000364215900026.
53. Pipe J G, Zwart N R, Aboussouan E A, Robison R K, Devaraj A, Johnson K O. A New Design and Rationale for 3D Orthogonally Oversampled k-Space Trajectories. Magnetic Resonance in Medicine. 2011; 66(5):1303-11. PubMed PMID: WOS:000296389800011.
54. Willmering M M, Robison R K, Wang H, Pipe J G, Woods J C. Implementation of the FLORET UTE sequence for lung imaging. Magnetic Resonance in Medicine. 2019; 82(3):1091-100. doi: 10.1002/mrm.27800.
55. Willmering M M, Niedbalski P J, Wang H, Walkup L L, Robison R K, Pipe J G, Cleveland Z I, Woods J C. Improved pulmonary 129Xe ventilation imaging via 3D-spiral UTE MRI. Magnetic Resonance in Medicine.n/a (n/a). doi: 10.1002/mrm.28114.
56. Niedbalski P J, Willmering M M, Robertson S H, Freeman M S, Loew W, Giaquinto R O, Ireland C, Pratt R G, Dumoulin C L, Woods J C, Cleveland Z I. Mapping and correcting hyperpolarized magnetization decay with radial keyhole imaging. Magnetic Resonance in Medicine. 2019; DOI: 10.1002/mrm.27721. doi: 10.1002/mrm.27721.
57. Guo J, Hardie W D, Cleveland Z I, Davidson C, Xu X, Madala S K, Woods J C. Longitudinal free-breathing MRI measurement of murine lung physiology in a progressive model of lung fibrosis. Journal of Applied Physiology. 2019; 126(4):1138-49. doi: 10.1152/japplphysiol.00993.2018. PubMed PMID: 30730810.
58. Higano N S, Hahn A D, Tkach J A, Cao X F, Walkup L L, Thomen R P, Merhar S L, Kingma P S, Fain S B, Woods J C. Retrospective Respiratory Self-Gating and Removal of Bulk Motion in Pulmonary UTE MRI of Neonates and Adults. Magnetic Resonance in Medicine. 2017; 77(3):1284-95. doi: 10.1002/mrm.26212. PubMed PMID: WOS:000397407800038.
58. Diggle, P. J., Sousa, I., Asar, 0. (2015). Real-time monitoring of progression towards renal failure in primary care patients. Biostatistics, 16(3): 522-36. DOI: 10.1093/biostatistics/kxu053.
Jiang, C.-R., Wang, J.-L. (2010). Covariate-adjusted functional principal components analysis for longitudinal data. The Annals of Statistics, 38(2): 1194-1226.
59. Szczesniak, R., McPhail, G. L., Duan, L. L., Macaluso, M., Amin, R. S., Clancy, J. P. (2013). A semiparametric approach to estimate rapid lung function decline in cystic fibrosis. Annals of Epidemiology, 23(12): 771-7. DOI: 10.1016/j.annepidem.2013.08.009. PMID: 24103586.
60. Szczesniak, R., Li, D., Su, W., Pestian, J., Seid, M., Clancy, J. P. (2017). Phenotypes of Rapid Cystic Fibrosis Lung Disease Progression during Adolescence and Young Adulthood. American Journal of Respiratory and Critical Care Medicine, 196(4): 471-478. DOI: 10.1164/rccm.201612-25740C. PMID: 28410569
61. Yao, F., Muller, H.-G., Wang, J.-L. (2005). Functional Data Analysis for Sparse Longitudinal Data. Journal of the American Statistical Association, 100(470): DOI: 10.1198/016214504000001745.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A method for treating an individual at risk for non-linear lung function decline, comprising a) determining, in said individual, a covariate comprising one or more biomarker selected from Immunoglobulin alpha-1 heavy chain constant region; kappa 1 immunoglobulin constant; Immunoglobulin kappa light chain VLJ region; immunoglobulin lambda; Immunoglobulin lambda constant 2; Immunoglobulin lambda constant 3; Tight junction protein 3; Alpha-1-acid glycoprotein 2 precursor; Signal-induced proliferation-associated 1-like protein 3; Plakophilin 4; Inter-alpha (globulin) inhibitor H2; Absent in melanoma 1 protein; Actin filament-associated protein 1 isoform X2; Serine/threonine-protein phosphatase PP1-beta catalytic subunit; Retinol-binding protein 4; Fermitin family homolog 1; Actin, cytoplasmic 2; Transthyretin; Melanoma inhibitory activity protein 3 isoform X2; Pleckstrin homology domain-containing family G member 1 isoform X3; Pleckstrin homology domain-containing family A member 5 isoforms X1-X9; Pleckstrin; Zinc finger protein 295; Protocadherin Fat 2; Cadherin-related family member 2 isoform X1; Voltage gated calcium channel alpha 1F subunit; Actin filament associated protein; Heat shock 70 kDa protein 1-like; EF-hand calcium binding protein 2; Polyamine modulated factor-1 (PMF1) protein; Keratin 16; Keratin 18; DNA replication ATP-dependent helicase/nuclease DNA2 isoform X4; Non-lens beta gamma-crystallin like protein; Bromodomain and WD repeat-containing protein 1 isoform X1; Collagen type V alpha 3 chain; Collagen type IV alpha; Dynein heavy chain 12, axonemal isoform X5; Serine/arginine repetitive matrix protein 1; Ras-related protein Rap-1A; AT-hook-containing transcription factor isoform 1; Coiled-coil domain-containing protein 18 isoforms X1-X7; Coiled-coil domain-containing protein 180; Patatin-like phospholipase domain-containing protein 2 isoform X1; Alstrom syndrome protein 1 isoform 1; aminopeptidase O isoform X9 (C9orf3); ankyrin-3 isoform 3; ARAP2 protein (ARAP2); Bifunctional glutamate/proline-tRNA ligase (EPRS); C10ORF6; CECR2 protein (CECR2); cingulin-like 1 (CGNL1); coiled-coil domain-containing protein 93 isoform X3 (CCDC93); complement component C2 (C2); complement component C6 isoform X7 (C6); complement factor H (CFH); connector enhancer of kinase suppressor of ras 2 isoform X2 (CNKSR2); CTP:phosphocholine cytidylyl-transferase; DNA annealing helicase and endonuclease ZRANB3 (ZRANB3); EPRSN1; fibrinogen alpha chain preproprotein, isoform alpha (FGA); filamin 2 (FLN2); Fras1-related extracellular matrix protein 2 (FREM2); FYVE, RhoGEF and PH domain-containing protein 5 isoform X2 (FGD5); gelsolin isoform X3 (GSN); glutamate receptor-interacting protein 1 isoform X7 (GRIP1); hCG1656772; histidine-rich glycoprotein isoform X1 (HRG); interferon regulatory factor-2 binding protein 2B; junction-mediating and -regulatory protein isoform X2 (JMY); KIAA0328 protein KIAA0328; 1a-related protein 1 isoform X5 LARP1; MAX gene-associated protein isoform X11 (MGA); paraoxanase-3; Platelet glycoprotein Ib alpha chain (GP1BA); PMFBP1 protein (PMFBP1); PRO2841; protein arginine N-methyltransferase 3 isoform X1 (PRMT3); Protein SCAF11 (SCAF11); ral GTPase-activating protein subunit alpha-1 isoform X12 (RALGAPA1); Receptor-type tyrosine-protein phosphatase C (PTPRC); RGS3 isoform C2PA-RGS3 (RGS3); Rho-GTPase activating protein 10 (ARHGAP10); RNA-binding motif protein, Y chromosome, family 1 member B isoform X1 (RBMY1B); protein-methionine sulfoxide oxidase MICAL3 isoform X10 (MICAL3); Protein sidekick-2 (SDK2); sacsin isoform X3 (SACS); SAPS domain family, member 2 (SAPS2); serum aryldialkylphosphatase precursor; spermatogenesis-associated protein 31C1 isoform X1 (SPATA31C1); synaptotagmin-like protein 2 isoform X10 (SYTL2); translation initiation factor (IF2); triadin isoform X17 (TRDN); uridine-cytidine kinase-like 1 isoform X7 (UCKL1); utrophin isoform X4 (UTRN); WD repeat-containing protein 64 isoform X2 (WDR64); zinc finger and AT hook domain containing (ZFAT); Alstrom syndrome protein 1 isoform 1; aminopeptidase O isoform X9 (C9orf3); ankyrin-3 isoform 3; ARAP2 protein (ARAP2); Bifunctional glutamate/proline-tRNA ligase (EPRS); C10ORF6; CECR2 protein (CECR2); cingulin-like 1 (CGNL1); coiled-coil domain-containing protein 93 isoform X3 (CCDC93); complement component C2 (C2); complement component C6 isoform X7 (C6); complement factor H (CFH); connector enhancer of kinase suppressor of ras 2 isoform X2 (CNKSR2); CTP:phosphocholine cytidylyl-transferase; DNA annealing helicase and endonuclease ZRANB3 (ZRANB3); EPRSN1; fibrinogen alpha chain preproprotein, isoform alpha (FGA); filamin 2 (FLN2); Fras1-related extracellular matrix protein 2 (FREM2); FYVE, RhoGEF and PH domain-containing protein 5 isoform X2 (FGD5); gelsolin isoform X3 (GSN); glutamate receptor-interacting protein 1 isoform X7 (GRIP1); hCG1656772; histidine-rich glycoprotein isoform X1 (HRG); interferon regulatory factor-2 binding protein 2B; junction-mediating and -regulatory protein isoform X2 (JMY); KIAA0328 protein KIAA0328; 1a-related protein 1 isoform X5 LARP1; MAX gene-associated protein isoform X11 (MGA); paraoxanase-3; Platelet glycoprotein Ib alpha chain (GP1BA); PMFBP1 protein (PMFBP1); PRO2841; protein arginine N-methyltransferase 3 isoform X1 (PRMT3); Protein SCAF11 (SCAF11); ral GTPase-activating protein subunit alpha-1 isoform X12 (RALGAPA1); Receptor-type tyrosine-protein phosphatase C (PTPRC); RGS3 isoform C2PA-RGS3 (RGS3); Rho-GTPase activating protein 10 (ARHGAP10); RNA-binding motif protein, Y chromosome, family 1 member B isoform X1 (RBMY1B); protein-methionine sulfoxide oxidase MICAL3 isoform X10 (MICAL3); Protein sidekick-2 (SDK2); sacsin isoform X3 (SACS); SAPS domain family, member 2 (SAPS2); serum aryldialkylphosphatase precursor; spermatogenesis-associated protein 31C1 isoform X1 (SPATA31C1); synaptotagmin-like protein 2 isoform X10 (SYTL2); translation initiation factor (IF2); triadin isoform X17 (TRDN); uridine-cytidine kinase-like 1 isoform X7 (UCKL1); utrophin isoform X4 (UTRN); WD repeat-containing protein 64 isoform X2 (WDR64); zinc finger and AT hook domain containing (ZFAT);

b) calculating a risk probability score based on said determining of one or more covariate, said risk probability score being used to characterize the individual as having no predicted lung impairment, mild predicted lung impairment, moderate predicted lung impairment, or severe predicted lung impairment wherein said risk probability score comprises a risk probability of said non-linear lung function decline in one or more parameters selected from a decrease in forced expiratory volume in one second (FEV1), pulmonary exacerbation (PE) frequency, FEV1-indicated exacerbation signal (FIES), ventilation defect percent (VDP), abnormal lung heterogeneity in lung as measured via imaging, lung hyperinflation, and combinations thereof; and c) treating said individual characterized as having mild predicted lung impairment, moderate predicted lung impairment, or severe predicted lung impairment with anti-inflammatory therapy.

2. The method of claim 1, said determining comprising determining an expression level of a protein of said biomarker.

3. The method of claim 1, further comprising determining an imaging marker covariate.

4. The method of claim 1, said imaging marker being a functional lung measurement, a structural lung measurement, or combinations thereof.

5. The method of claim 3, said imaging marker being obtained by an imaging method.

6. The method of claim 4, said imaging marker being detected using an image technique selected from hyperpolarized (HP) 129Xe, Ultra-short Echo-time (UTE) Magnetic resonance imaging (MRI), computed tomography (CT), and combinations thereof.

7. The method of claim 3, said imaging marker being structural remodeling.

8. The method of claim 3, said imaging marker being bronchiectasis.

9. The method of claim 1, said predicted lung impairment being a non-linear decline in one or more parameters selected from Ventilation Defect Percentage (VDP), FEV1, partial ventilation, ventilation heterogeneity, ventilation hyper-intensity or a combination thereof.

10. The method of claim 1, said risk probability score predicting the probability of lung function decline over a period selected from three weeks to four months, or six months, or twelve months.

11. The method of claim 1, wherein non-linear lung function decline is defined as a rate of change in longitudinal FEV1 that falls below 1.5% predicted/year.

12. The method of claim 1, wherein non-linear lung function decline is defined by the FEV1-indicated exacerbation signal (FIES) score.

13. The method of claim 1, further comprising detecting a one-or more covariates comprising a time-varying covariate.

14. The method of claim 13, said time-varying covariate selected from one or more of an infection with P. aeruginosa, an infection with Methicillin-resistant Staphylococcus aureus (MRSA), and Cystic-Fibrosis-related diabetes.

15. The method of claim 1, wherein said biomarker is one or more biomarkers selected from selected from Immunoglobulin alpha-1 heavy chain constant region; kappa 1 immunoglobulin constant; Immunoglobulin kappa light chain VLJ region; immunoglobulin lambda; Immunoglobulin lambda constant 2; Immunoglobulin lambda constant 3; Tight junction protein 3; Alpha-1-acid glycoprotein 2 precursor; Signal-induced proliferation-associated 1-like protein 3; Plakophilin 4; Inter-alpha (globulin) inhibitor H2; Absent in melanoma 1 protein; Actin filament-associated protein 1 isoform X2; Serine/threonine-protein phosphatase PP1-beta catalytic subunit; Retinol-binding protein 4; Fermitin family homolog 1; Actin, cytoplasmic 2; Transthyretin; Melanoma inhibitory activity protein 3 isoform X2; Pleckstrin homology domain-containing family G member 1 isoform X3; Pleckstrin homology domain-containing family A member 5 isoforms X1-X9; Pleckstrin; Zinc finger protein 295; Protocadherin Fat 2; Cadherin-related family member 2 isoform X1; Voltage gated calcium channel alpha 1F subunit; Actin filament associated protein; Heat shock 70 kDa protein 1-like; E F-hand calcium binding protein 2; Polyamine modulated factor-1 (PMF1) protein; Keratin 16 (KKRT16A); Keratin 18 (KRT18); DNA replication ATP-dependent helicase/nuclease DNA2 isoform X4; Non-lens beta gamma-crystallin like protein; Bromodomain and WD repeat-containing protein 1 isoform X1; Collagen type V alpha 3 chain; Collagen type IV alpha; Dynein heavy chain 12, axonemal isoform X5; Serine/arginine repetitive matrix protein 1; Ras-related protein Rap-1A; AT-hook-containing transcription factor isoform 1; Coiled-coil domain-containing protein 18 isoforms X1-X7; Coiled-coil domain-containing protein 180; and Patatin-like phospholipase domain-containing protein 2 isoform X1.

16. The method of claim 1, wherein said individual is diagnosed with cystic fibrosis (CF).

17. The method of claim 1 wherein said individual has a normal forced expiratory volume in one second (FEV1) as measured by spirometry.

18. The method of claim 1, wherein said individual is a pediatric patient.

19. The method of claim 1, wherein said individual is a patient under the age of 13 years of age.

20. The method of claim 1, wherein said method forecasts lung function trajectory for a period of about three weeks to about six months, or about six months to about twelve months.

21. The method of claim 1, further comprising applying a statistical algorithm to estimate correlation between said covariate value and predicted lung function.

22. The method of claim 1, wherein said method is carried out via a computer system, and wherein said method comprises capturing and displaying information related to said characterization of said individual using a graphical user interface (GUI).

23. The method of claim 1, further comprising assessing a variable selected from one or more of sex, body mass index (BMI), pulmonary exacerbation (PE), number of hospitalizations, antibiotic status, infection status, and combinations thereof, in said individual.

24. The method of claim 1, wherein said lung function decline is defined by one or more of absolute change in FEV1, rate of decline, risk of non-linear decline, and FIES.

* * * * *